(12) United States Patent
Abruzzese et al.

(10) Patent No.: US 7,579,326 B2
(45) Date of Patent: Aug. 25, 2009

(54) GENE SWITCH SYSTEMS EMPLOYING REGULATORS WITH DECREASED DIMERIZATION

(75) Inventors: Ronald V Abruzzese, The Woodlands, TX (US); Vidya Mehta, Houston, TX (US); Jeffrey L Nordstrom, College Station, TX (US); Jason Fewell, The Woodlands, TX (US); Bert O'Malley, Houston, TX (US); Sophia Tsai, Houston, TX (US)

(73) Assignees: Genetronics, Inc., San Diego, CA (US); Baylor College of Medicine, Houston, TX (US)

( * ) Notice: Subject to any disclaimer, the term of this patent is extended or adjusted under 35 U.S.C. 154(b) by 158 days.

(21) Appl. No.: 10/400,053

(22) Filed: Mar. 25, 2003

(65) Prior Publication Data

US 2003/0220286 A1 Nov. 27, 2003

Related U.S. Application Data

(63) Continuation of application No. PCT/US01/30305, filed on Sep. 25, 2001.

(60) Provisional application No. 60/278,281, filed on Mar. 23, 2001, provisional application No. 60/260,781, filed on Jan. 10, 2001, provisional application No. 60/235,030, filed on Sep. 25, 2000.

(51) Int. Cl.
*A01N 43/04* (2006.01)
*A61K 31/70* (2006.01)
*A01N 63/00* (2006.01)
*A01N 65/00* (2006.01)
*C12N 15/00* (2006.01)
*C07H 19/00* (2006.01)
*C07H 21/00* (2006.01)
*C07H 21/04* (2006.01)

(52) U.S. Cl. .................... 514/44; 424/93.1; 435/320.1; 536/23.1; 536/23.4; 536/24.5; 536/24.1

(58) Field of Classification Search .................. None
See application file for complete search history.

(56) References Cited

U.S. PATENT DOCUMENTS

| | | |
|---|---|---|
| 4,703,008 A | 10/1987 | Lin |
| 4,835,260 A | 5/1989 | Shoemaker |
| 4,954,437 A | 9/1990 | Beck et al. |
| 5,298,422 A | 3/1994 | Schwartz et al. |
| 5,364,791 A | 11/1994 | Vegeto et al. |
| 5,439,440 A | 8/1995 | Hofmann |
| 5,457,089 A | 10/1995 | Fibi et al. |
| 5,580,853 A | 12/1996 | Sytkowski |
| 5,614,184 A | 3/1997 | Sytkowski et al. |
| 5,688,679 A | 11/1997 | Powell |
| 5,704,908 A | 1/1998 | Hofmann et al. |
| 5,846,528 A | 12/1998 | Podsakoff et al. |
| 5,874,534 A | 2/1999 | Vegeto et al. |
| 5,888,772 A | 3/1999 | Okasinski et al. |
| 5,935,934 A | 8/1999 | Vegeto et al. |
| 6,093,699 A | 7/2000 | Sehon et al. |
| 6,153,407 A | 11/2000 | Sytkowski et al. |

FOREIGN PATENT DOCUMENTS

| | | |
|---|---|---|
| EP | 0232034 | 8/1987 |
| WO | WO 85/02610 | 6/1985 |
| WO | WO 90/07517 | 7/1990 |
| WO | WO 90/14356 | 11/1990 |
| WO | WO 93/23431 | 11/1993 |
| WO | WO 96/40911 | 12/1996 |
| WO | WO 97/44447 | 11/1997 |
| WO | WO 98/18925 | 5/1998 |
| WO | WO 99/06562 | 2/1999 |
| WO | WO 99/11801 | 3/1999 |
| WO | WO 99/32145 | 7/1999 |
| WO | WO 00/09713 | 2/2000 |
| WO | WO00/30618 | 5/2000 |
| WO | WO 00/31286 | 6/2000 |
| WO | WO 01/66149 | 9/2001 |

OTHER PUBLICATIONS

Nordstrom (2003) Steroids, 68: 1085-94.*
Rudinger (1976) Peptide Hormones, University Park Press, Baltimore, MD. pp. 1-7.*
Bowie, (1990) Science 247: 1306-10.*
Whelan et al., "Generation of Estrogen Receptor Mutants with Altered Ligand Specificity for Use in Establishing a Regulatable Gene Expression System," J. Steroid Biochem. Molec. Biol. vol. 58, No. 1, pp. 3-12, 1996.
Braselmann, et al., "A Selective Transcriptional Induction System for Mammalian Cells Based on Ga14-Estrogen Receptor Fusion Proteins," Proc. Nat Acad. Sci. USA vol. 90, pp. 1657-1661, Mar. 1993.
Sollerbrant, K., Akusjarvi, G, Linder, S., Svensson, C. The DNA binding domains of the yeast Gal4 and human c-jun transcription factors interact through the zinc-finger and bZIP motifs. Nucleic Acids Research 23 (1995) 588-594.

(Continued)

*Primary Examiner*—Robert M Kelly
(74) *Attorney, Agent, or Firm*—Wong Cabello Lutsch Rutherford & Brucculeri, LLP

(57) ABSTRACT

Disclosed is a novel inducible expression system characterized by undetectable biological effect in the absence of an inducer, but which exhibits efficient inducibility in the presence of an inducer.

50 Claims, 22 Drawing Sheets

OTHER PUBLICATIONS

Arici A., Marchburn, P., MacDonald, P., Dombrowski, R. Progesterone metabolism in human endometrial stromal and gland cells in culture. Steroids 64 (1999) 530-534.

Abruzzese, RV et al, Ligand-Dependent Regulation of Plasmid-Based transgene Expression in Vivo, Human Gene Therapy, Jun. 10, 1999, 1499-1507, vol. 10, Mary Ann Liebert, Inc.

Abruzzese, RV et al, Ligand-Dependent Regulation of Vascular Endothelial Growth Factor and Erythropoietin Expression by a Plasmid-Based Autoinducible GeneSwitch System, Molecular Therapy, Sep. 2000, 276-287, vol. 2.

Aurisicchio, L et al, Liver-Specific Alpha 2 Interferon Gene Expression results in Protection from Induced Hepatitis, Journal of Virology, May 2000, 4816-4823, vol. 74 No. 10.

Baleja, JD et al, Solution structure of the DNA-binding domain of Cd2-GAL4 from S. cerevisiae, Nature, Apr. 2, 1992, 450-453, vol. 356.

Bohl, D and Jean-Michel Heard, Delivering Erythropoietin through Genetically Engineered Cells, Journal of Am Soc Nephrol, 2000, S159-S162, vol. 11.

Burnstein, KL et al, Intragenic Sequences of the Human Glucocorticoid Receptor Complementary DNA Mediate Hormone-Inducible Receptor Messenger RNA Down-Regulation through Multiple Mechanisms, Molecular Endocrinology, 1994, 1764-1773, vol. 8.

Byravan , S et al, Two Point Mutations in the Hormone-Binding Domain of the Mouse Glucocorticoid Receptor That Dramatically Reduce Its Function, Molecular Endocrinology, 1991, 752-758, vol. 5.

Chen, D and Michael R. Stallcup, The Hormone-binding Role of 2 Cysteines Near the C Terminus of The Mouse Glucocorticoid Receptor, Journal of Biological Chemistry, Mar. 18, 1994, 7914-7918, vol. 269 No. 11.

Dahlman-Wright, K et al, Delineation of a small region within the major transactivation domain of the human glucocorticoid receptor that mediates transactivation of gene expression, Proc. Natl. Acad. Sci., Mar. 1994, 1619-1623, vol. 91.

Dai Y et al , Cellular and humoral immune responses to adenoviral vectors containing factor IX gene: Tolerization of factor IX and Vector antigens allows for long-term expression, PNAS 92 (1995) 1401.

Ferkol , T et al, Regulation of the phosphoenolpyruvate carboxykinase/human factor IX gene introduced onto the livers of adult rats by receptor-mediated gene transfer, J. FASEB, 1993, 1081-1091, vol. 7.

Fields, PA. et al, Role of Vector in Activation of T Cell Subsets in Immune Responses against the Secreted Transgene Product Factor IX, Molecuar Therapy, Mar. 2000, 225-235, vol. 1 No. 3.

Glue, P et al, A Dose-Ranging Study of Pegylated Interferon Alfa-2b and Ribavirin in Chronic Hepatitis C, Hepatology, 2000, 647-653, vol. 32.

Glue, P et al, Pegylated interferon-alpha2b: Pharmacokinetics, pharmacodynamics, safety, and preliminary efficacy data, Clin Pharmacol Ther, 2000, 556-567, vol. 68.

Herzog, R W et al, Long-term correction of canine hemophilia B by gene transfer of blood coagulation factor IX mediated by adeno-associated viral vector, Nature Medicine, Jan. 1999, 56-63, vol. 5 No. 1.

Hwang, JJ et al, Characteristics of the transcription activation function and the DNA binding domain of transcriptional enhancer factor-1, J. Embo, Jun. 1993, 2337-2348, vol. 12 No. 6.

Jacobs, K et al, Isolation and characterization of genomic and cDNA clones of human erythropoietin, Nature, Feb. 1985, 806-812, vol. 313.

Jenster, G et al, Steroid erceptor induction of gene transcription: A two-step model, Proc. Natl. Acad. Sci., Jul. 1997, 7879-7884, vol. 94.

Kessler, PD et al, Gene delivery to skeletal muscle results in sustained expression and systemic delivery of a therapeutic protein, Proc. Natl. Acad. Sci., Nov. 1996, 14082-14087, vol. 93.

Kloosterboer, HJ et al, Pharmacological Properties of a New Selective Antiprogestagen: Org 33628, Ann NY Acad Sci, 1995, 192-201, vol. 761.

Lemieux, P et al, A combination of poloxamers increases gene expression of plasmid DNA in skeletal muscle, Gene Therapy, 2000, 986-991, vol. 7.

Lin, F-K et al, Cloning and expression of the human erythropoietin gene, Proc. Natl. Acad. Sci., Nov. 1985, 7580-7584, vol. 82.

MacColl, GS et al, Using skeletal muscle as an artificial endocrine tissue, Journal of Endocrinology, 1999, 1-9, vol. 162.

Macias, MP et al, Cellular or Viral Protein Binding to a Cytomegalovirus Promoter Transcription Initiation Site: Effects on Transcription, Journal of Virology, Jun. 1996, 3628-3635, vol. 70 No. 6.

Mahato, RI et al, Biodistribution and Gene Expression of Lipid/Plasmid Complexes after Systemic Administration, Human Gene Therapy, Sep. 20, 1998, 2083-2099, vol. 9.

Mehta, V et al, Long-term, Drug-Dependent Regulation of Erythropoietin and Hematocrit in Mice Following Delivery of Plasmids to Skeletal Muscle, Experimental Hematology, Jul. 2000, 63, vol. 28 No. 7 supp.1.

Michou, AL et al, Adenovirus-mediated gene transfer: influence of transgene, mouse strain and tyoe of immune response on persistence of transgene expression, Gene Therapy, 1977, 472-482, vol. 4.

Milhon, J et al, Identification of Amino Acids in the t2-Region of the Mouse Glucocorticoid Receptor That Contribute to Hormone Binding and Transcriptional Activation, Molecular Endocrinology, 1997, 1795-1805, vol. 11.

Moruchi, H et al, Hydrophobic cluster analysis predicts an amino-terminal domain of varicella-zoster virus open reading frame 10 required for transcriptional activation, Proc. Natl. Acad. Sci., Sep. 1995, 9333-9337, vol. 92.

Muller, M et al, Multiple Domains of the Glucocorticoid Receptor Involved in Synergism with the CACCC Box Factor(s), Molecular Endocrinology, 1991, 1498-1503, vol. 5.

Oligino, T et al, Drug inducible transgene expression in brain using a herpes simplex virus vector, Gene Therapy, 1998, 491-495, vol. 5.

Pan, T and Joseph E. Coleman, GAL4 transcriptional factor is not a "zinc finger" but forms a Zn(II)2 Cys6 binuclear cluster, Proc. Natl. Acad. Sci., Mar. 1990, 2077-2081, vol. 87.

Pham, T et al, Ligand-Dependent and -Independent Function of the Transactivation Regions of the Human Estrogen Receptor in Yeast, Molecular Therapy, 1992, 1043-1050, vol. 6.

Porter, S Human Immune Response to Recombinant Human Proteins, Journal of Pharmaceutical Sciences, Jan. 2001, 1-11, vol. 90 No. 1.

Reece, RJ and M Ptashne, Determinants of binding-site specificity among yeast C6 zinc cluster proteins, Science, Aug. 13, 1993, 909-911, vol. 261 No. 5123.

Rendahl, KG et al, Regulation of gene expression in vivo following transduction by two seperate rAAV vectors, Nature Biotechnology, Aug. 1998, 757-761, vol. 16.

Rizzuto, G et al, Efficient and regulated erythropoietin production by nakes DNA injection and muscle electroporation, Proc. Natl. Acad. Sci., May 1999, 6417-6422, vol. 96.

Rizzuto, G et al, Gene Electrotransfer Results in a High-Level Transduction of Rat Skeletal Muscle and Corrects Anemia of Renal Failure, Human Gene Therapy, Sep. 1, 2000, 1891-1900, vol. 11, Mary Ann Liebert, Inc.

Rudich, SM et al, Dose response to a single intramuscular injection of recombinant adeno-associated virus-erythropoietin in monkeys, Journal of Surg Res, May 15, 2000, 102-108, vol. 90 No. 2.

Schenker, S et al, Activity and Tolerance of a Continuous Subcutaneous Infusion of Interferon-alpha2b in Patients with Chronic Hepatitis C, Journal of Interferon and Cytokine Res., 1997, 665-670, vol. 17.

Schoonen, WG. et al, Human Progesterone Receptor A and B Isoforms in CHO Cells. II. Comparison of Binding, Transactivation and ED50 Values of Several Synthetic (Anti)progestagens in Vitro in CHO and MCF-7 Cells and in Vivo in Rabbits and Rats, J. Steroid Biochem. Molec. Biol., 1998, 157-170, vol. 64 No. 3-4, Elsevier Science Ltd.

Serguera, C et al, Control of Erythropoietin Secretion aby Doxycycline or Mifepristone in Mice Bearing Polymer-Encapsulated Engineered Cells, Human Gene Therapy, Feb. 10, 1999, 375-383, vol. 10, Mary Ann Liebert, Inc.

Smith, D et al, A phase I study of rDNA alpha-2b interferon as a 6-week continuous intravenous infusion, Cancer Chemotherapy and Pharmacology, 1987, 327-331, vol. 20.

Snyder, RO et al, Persistent and therapeutic concentrations of human factor IX in mice after heptic gene transfer of recombinant AAV vectors, Nature Genetics, Jul. 1997, 270-276, vol. 16.

Song, W et al, Cytotoxic T Lymphocyte Responses to Proteins Encoded by Heterologous Transgenes Transferred In Vivo by Adenoviral Vectors, Human Gene Therapy, Jul. 1, 1997, 1207-1217, vol. 8, Mary Ann Liebert, Inc.

Strasser-Wozak, E. et al, Splice Site Mutation in the Glucocorticoid Receptor Gene Causes Resistance to Glucocorticoid-induced Apoptosis in a Human Acute Leukemic Cell Line1, Cancer Research, Jan. 15, 1995, 348-353, vol. 55.

Svensson, EC et al, Long-Term Erythropoietin Expression in Rodents and Non-Human Primates Following Intramuscular Injection of a Replication-Defective Adenoviral Vector, Human Gene Therapy, Oct. 10, 1997, 1797-1806, vol. 8, Mary Ann Liebert, Inc.

Tripathy, SK et al, Immune responses to transgene-encoded proteins limit the stability of gene expression after injection of replication-defective adenovirus vectors, Nature Medicine, May 1996, 545-550.

Urra, JM et al, Rapid Method for Detection of Anti-Recombinant Human Erythropoietin Antibodies as a New Form of Erythropoietin Resistance, Clinical Chemistry, 1997, 848-849, vol. 43.

Wagner, KF et al, Chronic inborn erythropoietin leads to cardiac dysfunction and premature death in mice overexpressing erythropoietin, Blood, 536-542, vol. 97 No. 2, Jan. 2001.

Wang, Y et al. A regulatory system for use in gene transfer, Proc. Natl. Acad. Sci., Aug. 1994, 8180-8184, vol. 91. Medical Sciences.

Wang, Y et al, Positive and negative regulation of gene expression in eukaryotic cells with an inducible transcriptional regulator, Gene Therapy, 1997, 432-441, vol. 4, Stockton Press.

Webster, N et al, The Hormone-Binding Domains of the Estrogen and Glucocorticoid Receptors Contain an Inducible Transcription Activation Function, Cell, Jul. 15, 1988, 199-207, vol. 54.

Wen, D et al, Erythropoietin Structure-Function Relationships: High Degree of Sequence Homology Among Mammals, Blood, Sep. 1, 1993, 1507-1516, vol. 82 No. 5.

Ye, X et al, Regulated Delivery of Therapeutic Proteins After in Vivo Somatic Cell Gene Transfer, Science, Jan. 1, 1999, 88-91, vol. 283.

Zhou, S et al, Adeno-associated virus-mediated delivery of erythropoietin leads to sustained elevation of hematocrit in nonhuman primates, Gene Therapy, 1998, 665-670, vol. 5.

Zou, LL et al, Potential application of gene switch vector in gene therapy for traumatic brain injury, Society for Neuroscience Abstracts, 1999, 1092, vol. 25 No. 1-2.

Schneider, BL et al, A Self Modulating Myoblast Cell Line for Erythropoietin Delivery, Gene Therapy 8 (2001) 58-66.

Sullivan DE et al, Liver-Directed Gene Transfer in Non-Human Primates, Human Gene Therapy 8 (1997) 1195.

Samakoglu S et al, B minor-globin messenger RNA accumulation in reticulocytes governs improved erythopoiesis in B thalassemic mice after erythropoietin complementary DNA electrotransfer in muscles, Blood 97 (2000) 2213.

\* cited by examiner

```
       5'SS                              BP                      3'SS
         |                                |                        |
---CAGGTAAGT-----n=>47----TACTAAC--TTCTTTTTTTCTCTTCACAGG    SEQ. ID. NO: 5

MAGGTRAGT                         YNYTRAY     YYYYYYYYYYYYYYYYYNYAGG    SEQ. ID. NO: 6

```
                              5'ss
             PacI              |           BbsI
NNNNNNNNNNNTTAATTAACAGGTAAGTGTCTTCCTCCTGTTTCCTTCCCCCTGCT

PstI                      NheI
ATTCTGCTCAACCTTCCTATCAGAAACTGCAGTATCTGTATTTTTGCTAGCAGTT

BP                    3'ss
      |           EarI      |      NcoI
ATACTAACGGTTCTTTTTTTCTCTTCACAGGCCACCATGGNNNNNNNNNNN    SEQ.ID.NO:7
```

Fig. 4

*GeneSwitch coding sequence* pGS1210/1382 - GeneSwitch coding sequence version 3.1 (SEQ.ID.NO:12)
pGS1539/1598 - GeneSwitch coding sequence version 4.0 (GAL4 domain underlined) (SEQ.ID. NO:13)

```
                1                                                50
{1210cds}  ATGGACTCCC AGCAGCCAGA TCTGAAGCTA CTGTCTTCTA TCGAACAAGC
{1539cds}  ATGGACTCCC AGCAGCCAGA TCTGAAGCTA CTGTCTTCTA TCGAACAAGC 51                                              100
{1210cds}  ATGCGATATT TGCCGACTTA AAAAGCTCAA GTGCTCCAAA GAAAAACCGA
{1539cds}  ATGCGATATT TGCCGACTTA AAAAGCTCAA GTGCTCCAAA GAAAAACCGA 101                                             150
{1210cds}  AGTGCGCCAA GTGTCTGAAG AACAACTGGG AGTGTCGCTA CTCTCCCAAA
{1539cds}  AGTGCGCCAA GTGTCTGAAG AACAACTGGG AGTGTCGCTA CTCTCCCAAA 151                                             200
{1210cds}  ACCAAAAGGT CTCCGCTGAC TAGGGCACAT CTGACAGAAG TGGAATCAAG
{1539cds}  ACCAAAAGGT CTCCGCTGAC TAGGGCACAT CTGACAGAAG TGGAATCAAG 201                                             250
{1210cds}  GCTAGAAAGA CTGGAACAGC TATTTCTACT GATTTTTCCT CGAGAAGACC
{1539cds}  GCTAGAAAGA CTGGAACAGC TATTTCTACT GATTTTTCCT CGA.......

251                                             300
{1210cds}  TTGACATGAT TTTGAAAATG GATTCTTTAC AGGATATAAA AGCATTGTTA
{1539cds}  ..................................................

301                                             350
{1210cds}  GAATTCCCGG GTGTCGACCA GAAAAAGTTC AATAAAGTCA GAGTTGTGAG
{1539cds}  ................GACCA GAAAAAGTTC AATAAAGTCA GAGTTGTGAG 351                                             400
{1210cds}  AGCACTGGAT GCTGTTGCTC TCCCACAGCC AGTGGGCGTT CCAAATGAAA
{1539cds}  AGCACTGGAT GCTGTTGCTC TCCCACAGCC AGTGGGCGTT CCAAATGAAA 401                                             450
{1210cds}  GCCAAGCCCT AAGCCAGAGA TTCACTTTTT CACCAGGTCA AGACATACAG
{1539cds}  GCCAAGCCCT AAGCCAGAGA TTCACTTTTT CACCAGGTCA AGACATACAG 451                                             500
{1210cds}  TTGATTCCAC CACTGATCAA CCTGTTAATG AGCATTGAAC CAGATGTGAT
{1539cds}  TTGATTCCAC CACTGATCAA CCTGTTAATG AGCATTGAAC CAGATGTGAT 501                                             550
{1210cds}  CTATGCAGGA CATGACAACA CAAAACCTGA CACCTCCAGT TCTTTGCTGA
{1539cds}  CTATGCAGGA CATGACAACA CAAAACCTGA CACCTCCAGT TCTTTGCTGA
```

*Fig. 7A*

```
            551                                                          600
{1210cds}   CAAGTCTTAA TCAACTAGGC GAGAGGCAAC TTCTTTCAGT AGTCAAGTGG
{1539cds}   CAAGTCTTAA TCAACTAGGC GAGAGGCAAC TTCTTTCAGT AGTCAAGTGG 601                                                          650
{1210cds}   TCTAAATCAT TGCCAGGTTT TCGAAACTTA CATATTGATG ACCAGATAAC
{1539cds}   TCTAAATCAT TGCCAGGTTT TCGAAACTTA CATATTGATG ACCAGATAAC 651                                                          700
{1210cds}   TCTCATTCAG TATTCTTGGA TGAGCTTAAT GGTGTTTGGT CTAGGATGGA
{1539cds}   TCTCATTCAG TATTCTTGGA TGAGCTTAAT GGTGTTTGGT CTAGGATGGA 701                                                          750
{1210cds}   GATCCTACAA ACACGTCAGT GGGCAGATGC TGTATTTTGC ACCTGATCTA
{1539cds}   GATCCTACAA ACACGTCAGT GGGCAGATGC TGTATTTTGC ACCTGATCTA 751                                                          800
{1210cds}   ATACTAAATG AACAGCGGAT GAAAGAATCA TCATTCTATT CATTATGCCT
{1539cds}   ATACTAAATG AACAGCGGAT GAAAGAATCA TCATTCTATT CATTATGCCT 801                                                          850
{1210cds}   TACCATGTGG CAGATCCCAC AGGAGTTTGT CAAGCTTCAA GTTAGCCAAG
{1539cds}   TACCATGTGG CAGATCCCAC AGGAGTTTGT CAAGCTTCAA GTTAGCCAAG 851                                                          900
{1210cds}   AAGAGTTCCT CTGTATGAAA GTATTGTTAC TTCTTAATAC AATTCCTTTG
{1539cds}   AAGAGTTCCT CTGTATGAAA GTATTGTTAC TTCTTAATAC AATTCCTTTG 901                                                          950
{1210cds}   GAAGGGCTAC GAAGTCAAAC CCAGTTTGAG GAGATGAGGT CAAGCTACAT
{1539cds}   GAAGGGCTAC GAAGTCAAAC CCAGTTTGAG GAGATGAGGT CAAGCTACAT 951                                                         1000
{1210cds}   TAGAGAGCTC ATCAAGGCAA TTGGTTTGAG GCAAAAAGGA GTTGTGTCGA
{1539cds}   TAGAGAGCTC ATCAAGGCAA TTGGTTTGAG GCAAAAAGGA GTTGTGTCGA 1001                                                        1050
{1210cds}   GCTCACAGCG TTTCTATCAA CTTACAAAAC TTCTTGATAA CTTGCATGAT
{1539cds}   GCTCACAGCG TTTCTATCAA CTTACAAAAC TTCTTGATAA CTTGCATGAT 1051                                                        1100
{1210cds}   CTTGTCAAAC AACTTCATCT GTACTGCTTG AATACATTTA TCCAGTCCCG
{1539cds}   CTTGTCAAAC AACTTCATCT GTACTGCTTG AATACATTTA TCCAGTCCCG 1101                                                        1150
{1210cds}   GGCACTGAGT GTTGAATTTC CAGAAATGAT GTCTGAAGTT ATTGCTGGGT
{1539cds}   GGCACTGAGT GTTGAATTTC CAGAAATGAT GTCTGAAGTT ATTGCTGGGT
```

*Fig. 7B*

```
             1151                                                    1200
{1210cds} CGACGCCCAT GGAATTCCAG TACCTGCCAG ATACAGACGA TCGTCACCGG
{1539cds} CGACGCCCAT GGAATTCCAG TACCTGCCAG ATACAGACGA TCGTCACCGG
             1201                                                    1250
{1210cds} ATTGAGGAGA AACGTAAAAG GACATATGAG ACCTTCAAGA GCATCATGAA
{1539cds} ATTGAGGAGA AACGTAAAAG GACATATGAG ACCTTCAAGA GCATCATGAA 1251                                                    1300
{1210cds} GAAGAGTCCT TTCAGCGGAC CCACCGACCC CCGGCCTCCA CCTCGACGCA
{1539cds} GAAGAGTCCT TTCAGCGGAC CCACCGACCC CCGGCCTCCA CCTCGACGCA 1301                                                    1350
{1210cds} TTGCTGTGCC TTCCCGCAGC TCAGCTTCTG TCCCCAAGCC AGCACCCCAG
{1539cds} TTGCTGTGCC TTCCCGCAGC TCAGCTTCTG TCCCCAAGCC AGCACCCCAG 1351                                                    1400
{1210cds} CCCTATCCCT TTACGTCATC CCTGAGCACC ATCAACTATG ATGAGTTTCC
{1539cds} CCCTATCCCT TTACGTCATC CCTGAGCACC ATCAACTATG ATGAGTTTCC 1401                                                    1450
{1210cds} CACCATGGTG TTTCCTTCTG GGCAGATCAG CCAGGCCTCG GCCTTGGCCC
{1539cds} CACCATGGTG TTTCCTTCTG GGCAGATCAG CCAGGCCTCG GCCTTGGCCC 1451                                                    1500
{1210cds} CGGCCCCTCC CCAAGTCCTG CCCCAGGCTC CAGCCCCTGC CCCTGCTCCA
{1539cds} CGGCCCCTCC CCAAGTCCTG CCCCAGGCTC CAGCCCCTGC CCCTGCTCCA 1501                                                    1550
{1210cds} GCCATGGTAT CAGCTCTGGC CCAGGCCCCA GCCCCTGTCC CAGTCCTAGC
{1539cds} GCCATGGTAT CAGCTCTGGC CCAGGCCCCA GCCCCTGTCC CAGTCCTAGC 1551                                                    1600
{1210cds} CCCAGGCCCT CCTCAGGCTG TGGCCCCACC TGCCCCCAAG CCCACCCAGG
{1539cds} CCCAGGCCCT CCTCAGGCTG TGGCCCCACC TGCCCCCAAG CCCACCCAGG 1601                                                    1650
{1210cds} CTGGGGAAGG AACGCTGTCA GAGGCCCTGC TGCAGCTGCA GTTTGATGAT
{1539cds} CTGGGGAAGG AACGCTGTCA GAGGCCCTGC TGCAGCTGCA GTTTGATGAT 1651                                                    1700
{1210cds} GAAGACCTGG GGGCCTTGCT TGGCAACAGC ACAGACCCAG CTGTGTTCAC
{1539cds} GAAGACCTGG GGGCCTTGCT TGGCAACAGC ACAGACCCAG CTGTGTTCAC 1701                                                    1750
{1210cds} AGACCTGGCA TCCGTCGACA ACTCCGAGTT TCAGCAGCTG CTGAACCAGG
{1539cds} AGACCTGGCA TCCGTCGACA ACTCCGAGTT TCAGCAGCTG CTGAACCAGG
```

*Fig. 7C*

```
              1751                                                    1800
{1210cds}  GCATACCTGT  GGCCCCCCAC  ACAACTGAGC  CCATGCTGAT  GGAGTACCCT
{1539cds}  GCATACCTGT  GGCCCCCCAC  ACAACTGAGC  CCATGCTGAT  GGAGTACCCT 1801                                                    1850
{1210cds}  GAGGCTATAA  CTCGCCTAGT  GACAGGGGCC  CAGAGGCCCC  CCGACCCAGC
{1539cds}  GAGGCTATAA  CTCGCCTAGT  GACAGGGGCC  CAGAGGCCCC  CCGACCCAGC 1851                                                    1900
{1210cds}  TCCTGCTCCA  CTGGGGGCCC  CGGGGCTCCC  CAATGGCCTC  CTTTCAGGAG
{1539cds}  TCCTGCTCCA  CTGGGGGCCC  CGGGGCTCCC  CAATGGCCTC  CTTTCAGGAG 1901                                                    1950
{1210cds}  ATGAAGACTT  CTCCTCCATT  GCGGACATGG  ACTTCTCAGC  CCTGCTGAGT
{1539cds}  ATGAAGACTT  CTCCTCCATT  GCGGACATGG  ACTTCTCAGC  CCTGCTGAGT 1951       1965
{1210cds}  CAGATCAGCT  CCTAA
{1539cds}  CAGATCAGCT CCTAA
```

Fig. 7D

GeneSwitch amino acid sequence pGS1210/1382 - GeneSwitch amino acid sequence v 3.1 (SEQ.ID. NO: 14)
pGS1539/1598 - GeneSwitch amino acid sequence v 4.0 (GAL4 domain underlined) (SEQ.ID. NO: 15)

```
              1                                                    50
{1210}   MDSQQPDLKL LSSIEQACDI CRLKKLKCSK EKPKCAKCLK NNWECRYSPK
{1539}   MDSQQPDLKL LSSIEQACDI CRLKKLKCSK EKPKCAKCLK NNWECRYSPK 51                                                  100
{1210}   TKRSPLTRAH LTEVESRLER LEQLFLLIFP REDLDMILKM DSLQDIKALL
{1539}   TKRSPLTRAH LTEVESRLER LEQLFLLIFP R.................

101                                                 150
{1210}   EFPGVDQKKF NKVRVVRALD AVALPQPVGV PNESQALSQR FTFSPGQDIQ
{1539}   .....DQKKF NKVRVVRALD AVALPQPVGV PNESQALSQR FTFSPGQDIQ 151                                                 200
{1210}   LIPPLINLLM SIEPDVIYAG HDNTKPDTSS SLLTSLNQLG ERQLLSVVKW
{1539}   LIPPLINLLM SIEPDVIYAG HDNTKPDTSS SLLTSLNQLG ERQLLSVVKW 201                                                 250
{1210}   SKSLPGFRNL HIDDQITLIQ YSWMSLMVFG LGWRSYKHVS GQMLYFAPDL
{1539}   SKSLPGFRNL HIDDQITLIQ YSWMSLMVFG LGWRSYKHVS GQMLYFAPDL 251                                                 300
{1210}   ILNEQRMKES SFYSLCLTMW QIPQEFVKLQ VSQEEFLCMK VLLLLNTIPL
{1539}   ILNEQRMKES SFYSLCLTMW QIPQEFVKLQ VSQEEFLCMK VLLLLNTIPL 301                                                 350
{1210}   EGLRSQTQFE EMRSSYIREL IKAIGLRQKG VVSSSQRFYQ LTKLLDNLHD
{1539}   EGLRSQTQFE EMRSSYIREL IKAIGLRQKG VVSSSQRFYQ LTKLLDNLHD 351                                                 400
{1210}   LVKQLHLYCL NTFIQSRALS VEFPEMMSEV IAGSTPMEFQ YLPDTDDRHR
{1539}   LVKQLHLYCL NTFIQSRALS VEFPEMMSEV IAGSTPMEFQ YLPDTDDRHR 401                                                 450
{1210}   IEEKRKRTYE TFKSIMKKSP FSGPTDPRPP PRRIAVPSRS SASVPKPAPQ
{1539}   IEEKRKRTYE TFKSIMKKSP FSGPTDPRPP PRRIAVPSRS SASVPKPAPQ 451                                                 500
{1210}   PYPFTSSLST INYDEFPTMV FPSGQISQAS ALAPAPPQVL PQAPAPAPAP
{1539}   PYPFTSSLST INYDEFPTMV FPSGQISQAS ALAPAPPQVL PQAPAPAPAP
```

*Fig. 8A*

```
          501                                                        550
{1210}    AMVSALAQAP APVPVLAPGP PQAVAPPAPK PTQAGEGTLS EALLQLQFDD
{1539}    AMVSALAQAP APVPVLAPGP PQAVAPPAPK PTQAGEGTLS EALLQLQFDD 551                                                        600
{1210}    EDLGALLGNS TDPAVFTDLA SVDNSEFQQL LNQGIPVAPH TTEPMLMEYP
{1539}    EDLGALLGNS TDPAVFTDLA SVDNSEFQQL LNQGIPVAPH TTEPMLMEYP 601                                                        650
{1210}    EAITRLVTGA QRPPDPAPAP LGAPGLPNGL LSGDEDFSSI ADMDFSALLS
{1539}    EAITRLVTGA QRPPDPAPAP LGAPGLPNGL LSGDEDFSSI ADMDFSALLS 651     655
{1210}    QISS*
{1539} QISS*
```

*Fig. 8B*

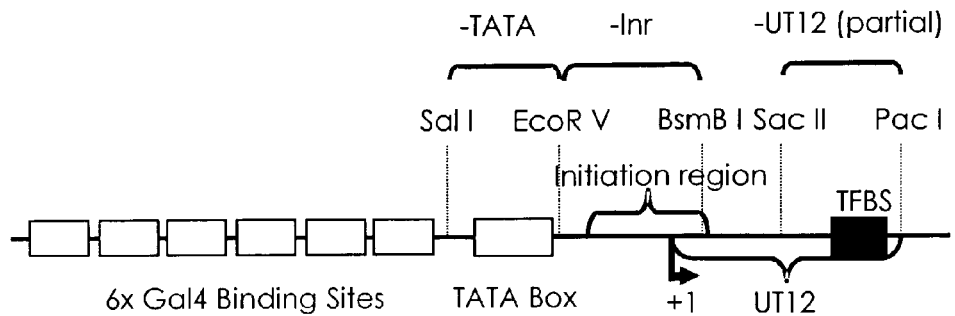
Fig. 9A
Inducible 6X GAL4/TATA Promoter
...AAGCGGAGTACTGTCCTCCGAGTGGAGTACTGTCCTCCGAGCGGAGTACTGTCCTCCGAGTCG
AGGGTCGAAGCGGAGTACTGTCCTCCGAGTGGAGTACTGTCCTCCGAGCGGAGTACTGTCCTCCG
AGTCGACTCTAGAGGGTATATAATGGATCTCGAGATATCGGAGCT ↓ CGTTTAGTGAACCGTC..
(SEQ.ID.NO:25)
Fig. 9B
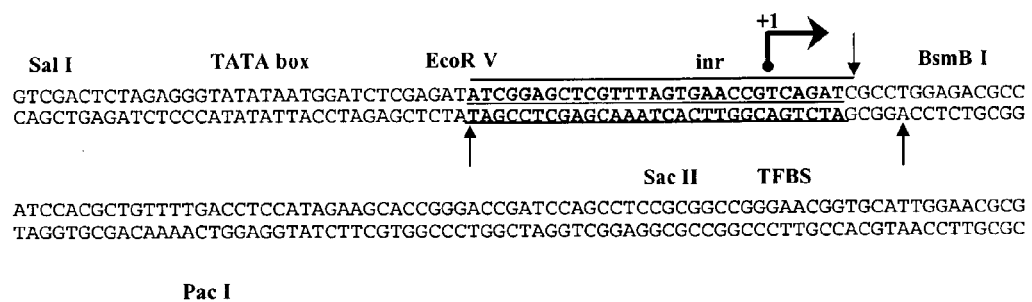
SEQ.ID.NO: 17
Fig. 9C

*Inducible Promoter Region* pEP1556 - intact inducible promoter region: | TATA box |/initiator region (inr)/UT12
  transcription factor binding site (UT12-TFBS)
pEP1595 - *Sal*I/*Eco*RV deletion of TATA box promoter region:  inr/UT12-TFBS
pEP1596 - *Eco*RV/*Bsm*BI deletion of inr region:  | TATA box |/UT12-TFBS
pEP1597 - *Sac*II/*Pac*I deletion of UT12 region:  | TATA box |/inr

```
             1                                                    50
{pep1556}  CCGAGTCGAC TCTAGAGGGT ATATAATGGA TCTCGAGATA TCGGAGCTCG
{pep1595}  CCGAGTCGA~ ~~~~~~~~~~ ~~~~~~~~~~ ~~~~~~~~~A TCGGAGCTCG
{pep1596}  CCGAGTCGAC TCTAGAGGGT ATATAATGGA TCTCGAGAT~ ~~~~~~~~~~
{pep1597}  CCGAGTCGAC TCTAGAGGGT ATATAATGGA TCTCGAGATA TCGGAGCTCG 51                                                  100
{pep1556}  TTTAGTGAAC CGTCAGATCG CCTGGAGACG CCATCCACGC TGTTTTGACC
{pep1595}  TTTAGTGAAC CGTCAGATCG CCTGGAGACG CCATCCACGC TGTTTTGACC
{pep1596}  ~~~~~~~~~~ ~~~~~~~~CG CCTGGAGACG CCATCCACGC TGTTTTGACC
{pep1597}  TTTAGTGAAC CGTCAGATCG CCTGGAGACG CCATCCACGC TGTTTTGACC 101                                                 150
{pep1556}  TCCATAGAAG ACACCGGGAC CGATCCAGCC TCCGCGGCCG GGAACGGTGC
{pep1595}  TCCATAGAAG ACACCGGGAC CGATCCAGCC TCCGCGGCCG GGAACGGTGC
{pep1596}  TCCATAGAAG ACACCGGGAC CGATCCAGCC TCCGCGGCCG GGAACGGTGC
{pep1597}  TCCATAGAAG ACACCGGGAC CGATCCAGCC TCC~~~~~~~ ~~~~~~~~~~

151              184
{pep1556}  ATTGGAACGC GGATTCCCCG TGTTAATTAA CAGG    (SEQ. ID. NO: 18)
{pep1595}  ATTGGAACGC GGATTCCCCG TGTTAATTAA CAGG    (SEQ. ID. NO: 19)
{pep1596}  ATTGGAACGC GGATTCCCCG TGTTAATTAA CAGG    (SEQ. ID. NO: 20)
{pep1597}  ~~~~~~~~~~ ~~~~~~~~~~ ~~~~~~~TAA CAGG    (SEQ. ID. NO: 21)
```

*Fig. 10*

Feature Map
SK Promoter
  Start: 2   End: 440
UT12
  Start: 440   End: 550
IVS8
  Start: 561   End: 678
GeneSwitch CDS
  Start: 701   End: 2593
Gal4 (2-74)
  Start: 725   End: 943
hPR LBD
  Start: 950   End: 1774
p65 Activation Domain
  Start: 1784   End: 2593
hGH pA
  Start: 2626   End: 2821
pUC ori
  Start: 2946   End: 3802
KanR
  Start: 3853   End: 4647
f1 ori
  Start: 4912   End: 5367

Feature Map
6x GAL4 sites
  Start: 8   End: 137
E1b TATA
  Start: 147   End: 160
UT12
  Start: 171   End: 274
IVS8
  Start: 285   End: 402
hEPO
  Start: 410   End: 1001
hGH pA
  Start: 1028   End: 1217
pUC ori
  Start: 1286   End: 2072
Kan R
  Start: 2085   End: 2998
KanR CDS
  Start: 2085   End: 2879

```
            1 ggggccgctc tagctagagt ctgcctgccc cctgcctggc acagcccgta
           51 cctggccgca cgctccctca caggtgaagc tcgaaaactc cgtccccgta
          101 aggagccccg ctgcccccg aggcctcctc cctcacgcct cgctgcgctc
          151 ccggctcccg cacggccctg ggagaggccc ccaccgcttc gtccttaacg
          201 ggcccggcgg tgccggggga ttatttcggc cccggccccg gggggcccg
          251 gcagacgctc cttatacggc ccggcctcgc tcacctgggc cgcggccagg
          301 agcgccttct ttgggcagcg ccgggccggg ccgcgccgg gcccgacacc
          351 caaatatggc gacggccggg gccgcattcc tgggggccgg gcggtgctcc
          401 cgcccgcctc gataaaaggc tccggggccg gcgggcgact cagatcgcct
          451 ggagacgcca tccacgctgt tttgacctcc atagaagaca ccgggaccga
          501 tccagcctcc gcggccggga acgtgcatt ggaacgcgga ttccccgtgt
          551 taattaacag gtaagtgtct tcctcctgtt tccttcccct gctattctgc
          601 tcaaccttcc tatcagaaac tgcagtatct gtattttgc tagcagtaat
          651 actaacggtt cttttttct cttcacaggc caccaagcta ccggtccacc
GAL4 -    701 atggactccc agcagccaga tctgaagcta ctgtcttcta tcgaacaagc
DNA       751 atgcgatatt tgccgactta aaaagctcaa gtgctccaaa gaaaaaccga
binding   801 agtgcgccaa gtgtctgaag aacaactggg agtgtcgcta ctctcccaaa
domain    851 accaaaaggt ctccgctgac tagggcacat ctgacagaag tggaatcaag
from      901 gctagaaaga ctggaacagc tatttctact gatttttcct cgagaccaga
725-943   951 aaaagttcaa taaagtcaga gttgtgagag cactggatgc tgttgctctc
         1001 ccacagccag tgggcgttcc aaatgaaagc caagccctaa gccagagatt
         1051 cacttttca ccaggtcaag acatacagtt gattccacca ctgatcaacc
         1101 tgttaatgag cattgaacca gatgtgatct atgcaggaca tgacaacaca
         1151 aaacctgaca cctccagttc tttgctgaca agtcttaatc aactaggcga
Ligand   1201 gaggcaactt ctttcagtag tcaagtggtc taaatcattg ccaggttttc
binding  1251 gaaacttaca tattgatgac cagataactc tcattcagta ttcttggatg
domain   1301 agcttaatgg tgtttggtct aggatggaga tcctacagaac acgtcagtgg
(LBD)    1351 gcagatgctg tattttgcac ctgatctaat actaaatgaa cagcggatga
from     1401 aagaatcatc attctattca ttatgcctta ccatgtggca gatcccacag
950-1774 1451 gagtttgtca agcttcaagt tagccaagaa gagttcctct gtatgaaagt
         1501 attgttactt cttaatacaa ttcctttgga agggctacga agtcaaaccc
         1551 agtttgagga gatgaggtca agctacatta gagagctcat caaggcaatt
         1601 ggtttgaggc aaaaaggagt tgtgtcgagc tcacagcgtt tctatcaact
         1651 tacaaaactt cttgataact tgcatgatct tgtcaaacaa cttcatctgt
         1701 actgcttgaa tacatttatc cagtcccggg cactgagtgt tgaatttcca
         1751 gaaatgatgt ctgaagttat tgctgggtcg acgcccatgg aattccagta
         1801 cctgccagat acagacgatc gtcaccggat tgaggagaaa cgtaaaagga
         1851 catatgagac cttcaagagc atcatgaaga agagtccttt cagcggaccc
P65      1901 accgaccccc ggcctccacc tcgacgcatt gctgtgcctt cccgcagctc
trans    1951 agcttctgtc cccaagccag caccccagcc ctatcccttt acgtcatccc
domain   2001 tgagcaccat caactatgat gagtttccca ccatggtgtt tccttctggg
from     2051 cagatcagcc aggcctcggc cttggccccg gcccctcccc aagtcctgcc
1784-    2101 ccaggctcca gcccctgccc ctgctccagc catggtatca gctctggccc
2593     2151 aggccccagc ccctgtccca gtcctagccc caggccctcc tcaggctgtg
         2201 gccccacctg cccccaagcc cacccaggct ggggaaggaa cgctgtcaga
         2251 ggccctgctg cagctgcagt ttgatgatga agacctgggg gccttgcttg
         2301 gcaacagcac agacccagct gtgttcacag acctggcatc cgtcgacaac
         2351 tccgagtttc agcagctgct gaacaagggc atacctgtgg ccccccacac
         2401 aactgagccc atgctgatgg agtaccctga ggctataact cgcctagtga
         2451 caggggccca gaggcccccc gacccagctc ctgctccact gggggccccg
         2501 gggctcccca atggcctcct tcaggagat gaagacttct cctccattgc
         2551 ggacatggac ttctcagccc tgctgagtca gatcagctcc taaggatcct
```

*Fig. 13A*

```
2601 ccggactaga aaagccgaat tctgcaggaa ttgggtggca tccctgtgac
2651 ccctccccag tgcctctcct ggccctggaa gttgccactc cagtgcccac
2701 cagccttgtc ctaataaaat taagttgcat cattttgtct gactaggtgt
2751 ccttctataa tattatgggg tggaggggg tggtatggag caaggggcaa
2801 gttgggaaga caacctgtag ggctcgaggg ggggcccggt acgatctgcc
2851 ggtctcccta tagtgagtcg tattaatttc gataagccag gttaacctgc
2901 attaatgaat cggccaacgc gcggggagag gcggtttgcg tattgggcgc
2951 tcttccgctt cctcgctcac tgactcgctg cgctcggtcg ttcggctgcg
3001 gcgagcggta tcagctcact caaaggcggt aatacggtta tccacagaat
3051 caggggataa cgcaggaaag aacatgtgag caaaaggcca gcaaaaggcc
3101 aggaaccgta aaaaggccgc gttgctggcg tttttccata ggctccgccc
3151 ccctgacgag catcacaaaa atcgacgctc aagtcagagg tggcgaaacc
3201 cgacaggact ataaagatac caggcgtttc ccctggaag ctccctcgtg
3251 cgctctcctg ttccgaccct gccgcttacc ggatacctgt ccgcctttct
3301 cccttcggga agcgtggcgc tttctcatag ctcacgctgt aggtatctca
3351 gttcggtgta ggtcgttcgc tccaagctgg gctgtgtgca cgaaccccc
3401 gttcagcccg accgctgcgc cttatccggt aactatcgtc ttgagtccaa
3451 cccggtaaga cacgacttat cgccactggc agcagccact ggtaacagga
3501 ttagcagagc gaggtatgta ggcggtgcta cagagttctt gaagtggtgg
3551 cctaactacg gctacactag aagaacagta tttggtatct gcgctctgct
3601 gaagccagtt accttcggaa aaagagttgg tagctcttga tccggcaaac
3651 aaaccaccgc tggtagcggt ggtttttttg tttgcaagca gcagattacg
3701 cgcagaaaaa aaggatctca agaagatcct ttgatctttt ctacggggtc
3751 tgacgctcag tggaacgaaa actcacgtta agggattttg gtcatgagcg
3801 cgcctaggct tttgcaaaga tcgatcaaga gacaggatga ggatcgtttc
3851 gcatgattga acaagatgga ttgcacgcag gttctccggc cgcttgggtg
3901 gagaggctat tcggctatga ctgggcacaa cagacaatcg gctgctctga
3951 tgccgccgtg ttccggctgt cagcgcaggg gcgcccggtt ctttttgtca
4001 agaccgacct gtccggtgcc ctgaatgaac tgcaagacga ggcagcgcgg
4051 ctatcgtggc tggccacgac gggcgttcct tgcgcagctg tgctcgacgt
4101 tgtcactgaa gcgggaaggg actggctgct attgggcgaa gtgccggggc
4151 aggatctcct gtcatctcac cttgctcctg ccgagaaagt atccatcatg
4201 gctgatgcaa tgcggcggct gcatacgctt gatccggcta cctgcccatt
4251 cgaccaccaa gcgaaacatc gcatcgagcg agcacgtact cggatggaag
4301 ccggtcttgt cgatcaggat gatctggacg aagagcatca ggggctcgcg
4351 ccagccgaac tgttcgccag gctcaaggcg agcatgcccg acggcgagga
4401 tctcgtcgtg acccatggcg atgcctgctt gccgaatatc atggtggaaa
4451 atggccgctt ttctggattc atcgactgtg gccgctgggt gtggcggac
4501 cgctatcagg acatagcgtt ggctacccgt gatattgctg aagagcttgg
4551 cggcgaatgg gctgaccgct tcctcgtgct ttacggtatc gccgctcccg
4601 attcgcagcg catcgccttc tatcgccttc ttgacgagtt cttctgagcg
4651 ggactctggg gttcgaaatg accgaccaag cgacgcccaa cctgccatca
4701 cgagatttcg attccaccgc cgccttctat gaaaggttgg gcttcggaat
4751 cgttttccgg gacgccggct ggatgatcct ccagcgcggg gatctcatgc
4801 tggagttctt cgcccaccct aggcgcgctc atgagcggat acatatttga
4851 atgtatttag aaaaataaac aatagggt ccgcgcaca tttccccgaa
4901 aagtgccacc taaattgtaa gcgttaatat tttgttaaaa ttcgcgttaa
4951 attttgtta aatcagctca ttttttaacc aataggccga atcggcaaa
5001 atcccttata aatcaaaaga atagaccgag atagggttga gtgttgttcc
5051 agtttggaac aagagtccac tattaaagaa cgtggactcc aacgtcaaag
5101 ggcgaaaaac cgtctatcag ggcgatggcc cactacgtga accatcaccc
5151 taatcaagtt ttttggggtc gaggtgccgt aaagcactaa atcggaaccc
```

*Fig. 13B*

```
5201 taaagggagc ccccgattta gagcttgacg gggaaagccg gcgaacgtgg
5251 cgagaaagga agggaagaaa gcgaaaggag cgggcgctag ggcgctggca
5301 agtgtagcgg tcacgctgcg cgtaaccacc acacccgccg cgcttaatgc
5351 gccgctacag ggcgcgtccc attcgccatt caggctgcgc aactgttggg
5401 aagggcgatc ggtgcgggcc tcttcgctat tacgccagct ggcgaaaggg
5451 ggatgtgctg caaggcgatt aagttgggta acgccagggt tttcccagtc
5501 acgacgttgt aaaacgacgg ccagtgagcg cgcgtaatac gactcactat
5551 agggcgaatt gggtac      (SEQ. ID. NO: 22)
```

*Fig. 13C*

|     |      |            |            |            |            |            |
|-----|------|------------|------------|------------|------------|------------|
|     | 1    | gggtcgaagc | ggagtactgt | cctccgagtg | gagtactgtc | ctccgagcgg |
|     | 51   | agtactgtcc | tccgagtcga | gggtcgaagc | ggagtactgt | cctccgagtg |
|     | 101  | gagtactgtc | ctccgagcgg | agtactgtcc | tccgagtcga | ctctagaggg |
|     | 151  | tatataatgg | atctcgagat | gcctggagac | gccatccacg | ctgttttgac |
|     | 201  | ctccatagaa | gacaccggga | ccgatccagc | ctccgcggcc | gggaacggtg |
|     | 251  | cattggaacg | cggattcccc | gtgttaatta | acaggtaagt | gtcttcctcc |
|     | 301  | tgtttccttc | ccctgctatt | ctgctcaacc | ttcctatcag | aaactgcagt |
|     | 351  | atctgtattt | ttgctagcag | taatactaac | ggttcttttt | ttctcttcac |
|     | 401  | aggccaccaa | gcttccatgg | gggtgcacga | atgtcctgcc | tggctgtggc |
|     | 451  | tgctcctgtc | cctgctgtcc | ctcctctgg  | gcctcccagt | cctgggcgcc |
|     | 501  | ccaccacgcc | tcatctgtga | cagccgcgtc | ctggagaggt | atctcctgga |
| Human | 551 | ggccaaggag | gccgagaata | tcacgacggg | ctgtgctgaa | cactgcagcc |
| EPO | 601 | tgaatgagaa | tatcactgtc | ccagacacca | aagtgaattt | ctatgcctgg |
| Coding | 651 | aagaggatgg | aggtcgggca | gcaggccgtg | gaagtctggc | agggcctggc |
| Sequence | 701 | cctgctgtcc | gaagctgtcc | tgcggggcca | ggccctgctg | gtcaactctt |
| 417-998 | 751 | cccagccgtg | ggagcccctg | cagctgcatg | tggataaagc | cgtcagtggc |
|     | 801  | ctgcgcagcc | tcaccactct | gctgcgggct | ctgggagccc | agaaggaagc |
|     | 851  | catctcccct | ccagatgcgg | cctccgctgc | tccactccgc | acaatcactg |
|     | 901  | ctgacacttt | ccgcaaactc | ttccgagtct | actccaattt | cctccgggga |
|     | 951  | aagctgaagc | tgtacacagg | ggaggcctgc | aggacagggg | acagatgagt |
|     | 1001 | ctagaaaagc | cgaattctgc | aggaattggg | tggcatccct | gtgacccctc |
|     | 1051 | cccagtgcct | ctcctggccc | tggaagttgc | cactccagtg | cccaccagcc |
|     | 1101 | ttgtcctaat | aaaattaagt | tgcatcattt | tgtctgacta | ggtgtccttc |
|     | 1151 | tataatatta | tggggtggag | ggggtggta  | tggagcaagg | ggcaagttgg |
|     | 1201 | gaagacaacc | tgtagggctc | gagggggggc | ccggtaccag | cttttgttcc |
|     | 1251 | ctttagtgag | ggttaatttc | gagcttggtc | ttccgcttcc | tcgctcactg |
|     | 1301 | actcgctgcg | ctcggtcgtt | cggctgcggc | gagcggtatc | agctcactca |
|     | 1351 | aaggcggtaa | tacggttatc | cacagaatca | ggggataacg | caggaaagaa |
|     | 1401 | catgtgagca | aaaggccagc | aaaaggccag | gaaccgtaaa | aaggccgcgt |
|     | 1451 | tgctggcgtt | tttccatagg | ctccgccccc | ctgacgagca | tcacaaaaat |
|     | 1501 | cgacgctcaa | gtcagaggtg | gcgaaacccg | acaggactat | aaagatacca |
|     | 1551 | ggcgtttccc | cctggaagct | ccctcgtgcg | ctctcctgtt | ccgaccctgc |
|     | 1601 | cgcttaccgg | atacctgtcc | gcctttctcc | cttcgggaag | cgtggcgctt |
|     | 1651 | tctcatagct | cacgctgtag | gtatctcagt | tcggtgtagg | tcgttcgctc |
|     | 1701 | caagctgggc | tgtgtgcacg | aaccccccgt | tcagcccgac | cgctgcgcct |
|     | 1751 | tatccggtaa | ctatcgtctt | gagtccaacc | cggtaagaca | cgacttatcg |
|     | 1801 | ccactggcag | cagccactgg | taacaggatt | agcagagcga | ggtatgtagg |
|     | 1851 | cggtgctaca | gagttcttga | agtggtggcc | taactacggc | tacactagaa |
|     | 1901 | ggacagtatt | tggtatctgc | gctctgctga | agccagttac | cttcggaaaa |
|     | 1951 | agagttggta | gctcttgatc | cggcaaacaa | accaccgctg | gtagcggtgg |
|     | 2001 | ttttttgtt  | tgcaagcagc | agattacgcg | cagaaaaaaa | ggatctcaag |
|     | 2051 | aagatccttt | gatcttttct | acggggtctg | acgctcagaa | gaactcgtca |
|     | 2101 | agaaggcgat | agaaggcgat | gcgctgcgaa | tcgggagcgg | cgataccgta |
|     | 2151 | aagcacgagg | aagcggtcag | cccattcgcc | gccaagctct | tcagcaatat |
|     | 2201 | cacgggtagc | caacgctatg | tcctgatagc | ggtccgccac | acccagccgg |
|     | 2251 | ccacagtcga | tgaatccaga | aaagcggcca | ttttccacca | tgatattcgg |
|     | 2301 | caagcaggca | tcgccatgcg | tcacgacgag | atcctcgccg | tcgggcatgc |
|     | 2351 | gcgccttgag | cctggcgaac | agttcggctg | gcgcgagccc | ctgatgctct |
|     | 2401 | tcgtccagat | catcctgatc | gacaagaccg | gcttccatcc | gagtacgtgc |
|     | 2451 | tcgctcgatg | cgatgtttcg | cttggtggtc | gaatgggcag | gtagccggat |
|     | 2501 | caagcgtatg | cagccgccgc | attgcatcag | ccatgatgga | tactttctcg |
|     | 2551 | gcaggagcaa | ggtgagatga | caggagatcc | tgccccggca | cttcgcccaa |

*Fig. 14A*

```
2601 tagcagccag tcccttcccg cttcagtgac aacgtcgagc acagctgcgc
2651 aaggaacgcc cgtcgtggcc agccacgata gccgcgctgc ctcgtcctgc
2701 agttcattca gggcaccgga caggtcggtc ttgacaaaaa gaaccgggcg
2751 cccctgcgct gacagccgga acacggcggc atcagagcag ccgattgtct
2801 gttgtgccca gtcatagccg aatagcctct ccacccaagc ggccggagaa
2851 cctgcgtgca atccatcttg ttcaatcatg cgaaacgatc ctcatcctgt
2901 ctcttgatca gatcttgatc ccctgcgcca tcagatcctt ggcggcaaga
2951 aagccatcca gtttactttg cagggcttcc caaccttacc agagggcgcc
3001 ccagctggca attccggttc gcttgctgtc cataaaaccg cccagtctag
3051 caactgttgg gaagggcggg gctgcaggaa ttcgagcttg catgcctgca
        (SEQ.ID.NO:23)
```

*Fig. 14B*

GENE SWITCH SYSTEMS EMPLOYING REGULATORS WITH DECREASED DIMERIZATION

This application is a Continuation of International Application Serial No. PCT/US01/30305, filed Sep. 25, 2001 and published in English under PCT Article 21(2), which claims the benefit of U.S. Provisional Application Ser. No. 60/235,030, filed Sep. 25, 2000, U.S. Provisional Application Ser. No. 60/260,781, filed Jan. 10, 2001, and U.S. Provisional Application Ser. No. 60/278,281, filed Mar. 23, 2001, which are hereby incorporated by reference as if fully set forth herein.

TECHNICAL FIELD

The present invention relates to an improved regulated-gene-expression system characterized by low basal expression and high specific inducibility, and to the use of regulated gene expression for control of immunoreactivity in gene therapy.

BACKGROUND OF THE INVENTION

One goal of gene therapy is to deliver genes to somatic tissue in a manner that provides correction of inborn or acquired deficiencies and imbalances. Gene-based drug delivery offers a number of advantages over administration of recombinant proteins. These advantages include: conservation of native protein structure; improved biological activity; prolonged exposure to protein in the therapeutic range; prolonged availability of protein from each administration; avoidance of systemic toxicities; and avoidance of infectious and toxic impurities.

Efforts to develop gene-based delivery of therapeutic proteins such as, for example, erythropoietin ("EPO") for treatment of anemias of various etiologies have been underway for almost a decade. EPO is produced primarily in the kidney in adults and is responsible for stimulating the production of red blood cells from progenitor cells. In patients with renal insufficiency, compromised EPO production results in anemia. Low serum EPO levels may also be seen in anemic patients with cancer, as well as those with rheumatoid arthritis, HIV infection, ulcerative colitis, sickle cell anemia, and in anemia of prematurity. However, certain proteins such as erythropoietin may have adverse effects if administration is not carefully controlled. For example, unregulated exposure to erythropoietin may result in life-threatening erythroid hyperplasia. In humans suffering from polycythemia, or a high red-blood cell count, prophylactic phlebotomy or blood removal is employed to maintain a hematocrit level below 45%. In animal models of erythropoietin-gene therapy, unregulated expression systems routinely result in hematocrit levels in the range of 60-85%. (Savino, R., et al., International Patent Publication No. WO0009713, "Adenoviral Vectors Encoding Erythropoietin and Their Use in Gene Therapy"; Podsakoff, G., et al., U.S. Pat. No. 5,846,528; Svensson, E., et al., Hum Gene Ther 8(15):1797 (1997); Lemieux, P., et al., Gene Therapy 7:986 (2000)). Periodic blood removal may be necessitated to avoid stroke and other severe polycythemic pathologies. (Zhou, S., et al., Gene Therapy 5, 665 (1998)).

In unregulated viral-vector-based erythropoietin-gene-delivery systems, the resulting hematocrit has been found to be viral dose dependent. Attempted adjustment of the hematocrit has been through empirical titration of the administered viral dose. (Kessler, et al., Proc. Natl. Acid. Sci. 93:14082 (1996)). Control of adverse and life threatening side effects through viral-dose titration, however, does not provide a satisfactory margin of therapeutic safety. What is needed for expression of proteins such as erythropoietin is the ability to closely regulate expression of the introduced gene across a range of administration dosages.

Several regulated gene-expression systems for erythropoietin have been explored. For example, Rizzuto, G., et al., Proc. Natl. Acad. Sci. 96:6417 (1999), utilized a tetracycline-inducible promoter to drive expression of a mouse EPO gene from plasmid DNA administered in saline with electroporation. As a consequence of the high basal level of expression in this system, however, the amount of plasmid DNA that could be administered for controlled expression had to be empirically titrated to a sufficiently low delivery amount.

Regulated viral vector systems for EPO delivery have also been described. For example, Rendahl, K. et al., Nature Biotechnology 16:757 (1998), reported a regulated two-viral vector system in which administration of tetracycline is designed to down regulate EPO production through the interaction of the two-vector gene products. However, control of EPO production was dependent on administered viral dose with gradual uncontrolled rise in hematocrit levels at higher viral doses. Ye, X., et al., Science 283:88 (1999) also reported the use of a two-viral vector system designed to be regulated by rapamycin. Although plasma EPO levels could be regulated by rapamycin, the hematocrit level could not, thereby indicating a basal level of EPO expression sufficient to stimulate a maximal increase in hematocrit.

In addition, the use of viral vectors is complicated by the generation of immune responses to the vector in immunocompetent hosts. As a consequence, viral vectors are considered to have limited readministration potential. Manning, W. et al., International Published Application WO09906562, "Method Enabling Readministration of AAV Vector Via Immunosuppression of Host", described efforts to control this phenomena through the use of transient immunosuppression at the time of vector delivery. But immunosuppression, in general, may lead to undesirable side effects.

The use of a viral vector for ex vivo transformation of fibroblasts to provide a mutated steroid-hormone-regulated system of erythropoietin gene expression has also been reported. (Serguera, C. et al., Human Gene Therapy 10:375 (1999)). However, induction of gene expression by mifepristone resulted in polycythemia that was not reversible upon cessation of mifepristone treatment. What is needed is an improved regulated system where increases in hematocrit are not obtained in the absence of specific induction.

Recombinant interferon alpha "IFN-alpha" is the primary treatment for chronic hepatitis C virus infection. The current best treatment regimen (interferon with ribavirin) has a relatively low response rate that is attributed in part to the short half-life of interferon alpha in the circulation. Emerging therapies are interferons with covalently attached polyethylene glycol moieties (peginterferon) that are shown to have a longer half-life, sustained absorption and a slower rate of clearance. Clinical trials have indicated that use of peginterferon given once weekly is more effective than using non-modified interferon three times weekly. However, all of the routinely injected IFN-alpha protein therapies are associated with substantial side effects that result in part from the high levels of interferon that are obtained by bolus injection. What is needed is a long term continuous and consistent expression of low circulating levels of INF-alpha such that a sufficient anti-viral level is obtained without toxic peak levels. A potential method of achieving this goal with a minimum number of treatments is gene therapy. An adenoviral delivery system for expression of interferon alpha from the liver has been reported to provide protection of the liver from a hepatitis virus infection in a mouse model. Aurisicchio et al., J Virol 2000 May; 74(10):4816-23. However, because of potential adverse effects with uncontrolled interferon expression, the ability to regulate expression of the interferon may be required. What is needed in this context is a tightly regulated gene expression system for interferon alpha whereby induction can be obtained through administration of a non-toxic small molecule inducer.

Furthermore, the etiologies of many disease states are characterized by expression of a mutated protein or lack of protein expression due to a defect in one or more genes. Current treatment regimens include administration of human-derived protein or recombinant protein products to supplement the loss of endogenously produced protein. These proteins when administered are often viewed by the host as foreign, leading to the generation of antibodies to the administered protein that renders the treatment regimen ineffective. One example of a class of diseases that are due to a genetic absence of functional protein is hemophilia. Hemophilia A and B are caused by functional deficiencies in Factor VIII and Factor IX respectively. Hemophilic patients have a high incidence of developing inhibitors to replacement factors and much effort is focused on how to avoid this complication.

It has been demonstrated that expression of foreign proteins using a gene therapy approach can result in an immune response against the foreign protein. This response can be cellular, humoral or both and can result in rapid loss of vector-bearing cells (Fields et al., Mol Ther 1(3):225 (2000); Song et al. Hum Gene Ther 8(10):1207 (1997); Michou, et al., Gene Ther 4(5):473 (1997); Dai et al., Proc Natl Acad Sci USA 92(5):1401 (1995)). As an example of the effects of foreign transgene expression, when recombinant human EPO ("hEPO") transgenes are delivered to mice, immune responses to the foreign transgene product can neutralize elevations in hematocrit level, and antibody cross-reactivity to endogenous EPO can result in erythroid hypoplasia that may lead to fatal anemia. (Tripathy, et al. Nat Med. 2:545 (1996); (Kessler, et al., Proc. Natl. Acid. Sci. 93:14082 (1996)).

Hence, what is needed is an improved, regulated gene expression system having extremely low levels of basal expression while retaining high inducibility. What is further needed is a system for minimizing the potential for developing of an immune response to therapeutic gene products.

SUMMARY OF THE INVENTION

The present invention provides an improved molecular-switch, inducible-expression system for regulating the expression of a nucleic acid sequence in gene therapy under conditions in which tight control of expression is of particular importance. In one aspect of the invention, a system is provided wherein expression of the gene to be induced is characterized by low or undetectable expression or biological effect in the absence of the inducer, but in the presence of the inducer, is characterized by efficient induction of expression or biological effect. In another aspect of the present invention, a method is provided that induces a measure of tolerance to transgenic proteins, thus making long-term administration of the protein by gene therapy or recombinant protein possible and effective.

In one embodiment of the invention, the molecular-switch, inducible-expression system comprises two nucleic acid or expression cassettes. The first expression cassette includes a promoter driving the expression of a molecular switch protein. The molecular switch protein is a chimeric or fusion protein that includes a mutated DNA binding domain characterized by a modification that eliminates a domain having a potential for autodimerization in the absence of an inducer while retaining those domains required for recognition of its cognate DNA sequence on the promoter of the second expression cassette. In one embodiment the DNA binding domain is a truncated GAL-4 DNA binding domain. The fusion protein further comprises a transactivation domain, and a mutated ligand-binding domain of a steroid-hormone receptor capable of being activated by a non-natural ligand inducer such as mifepristone. In a one embodiment, the promoter is a tissue-specific promoter such as α-ac tin promoter specific for muscle tissues. The first expression cassette may also include 5' untranslated regions, synthetic introns, and poly (A) signals that increase the fidelity and level of expression of the molecular switch gene. The second expression cassette includes a transgene encoding a desired gene product controlled by an inducible promoter comprising GAL-4 DNA-binding sites linked to a minimal promoter. The second expression cassette may also include 5' untranslated regions, synthetic introns, and poly (A) signals that increase the fidelity and level of expression of the transgene to be induced.

In another embodiment of the invention, the inducible expression system is applied in vivo to effect expression of a transgene for gene therapy purposes. In one embodiment the inducible expression system is formulated with non-ionic or anionic polymers and injected into an animal or human. Enhancement of transfection in vivo may be obtained with in vivo electroporation. In addition to using a tightly regulated expression system, a method is provided to minimize the immune response of the animal to the transgene product or any other introduced nucleic acids and proteins. Preferably, after administration of the expression system, the induction of the expression system occurs after the animal's initial immune reaction to the injection and electroporation has subsided. For example, a lag time between the administration of the expression system and the inducer may be at least 12 days, more preferably, at least 20 days, or most preferably, greater than 50 days. Furthermore, the method may also include the administration of the inducer using a pulsatile program that further enhances the immunotolerance of the animal.

In another embodiment of the invention, the inducible expression system as introduced in an animal may be characterized by the ability to repetitively effect a biological response using repetitive administration of an inducer of the expression system. In a preferred embodiment, the biological response to the inducer is maintained over a period of at least one year using only a single administration of the expression system.

Other and further objects, features and advantages will be apparent from the following description of the presently preferred embodiments of the invention which are given for the purposes of disclosure when taken in conjunction with the accompanying drawings.

BRIEF DESCRIPTION OF THE DRAWINGS

FIG. 2 also depicts the interaction between the gene product (i.e. regulator protein) of the GENESWITCH® plasmid and an inducer (e.g. anti-progestin) to induce the expression of EPO encoded by the inducible EPO plasmid.

FIG. 3 depicts the consensus intron structure SEQ. ID. NO. 6 and the sequence of a synthetic intron SEQ. ID. NO. 5 according to one embodiment of the present invention.

FIG. 4 depicts the sequence of a particular synthetic intron, IVS8 SEQ. ID. NO. 7, according to one embodiment of the present invention.

FIG. 6 also depicts the comparison of basal and induced expression of human EPO in COS-1 cells using inducible hEPO plasmids regulated by various GENESWITCH® plasmids (pGS1210 (CMV-GSv3.1) or pGS1539 (CMV-GSv4.0) according to one aspect of the present invention.

FIG. 7 depicts the coding sequences of the GENESWITCH® plasmids v.3.1 (SEQ. ID. NO. 12) and v.4.0 (SEQ. ID. NO. 13), wherein SEQ. ID. NO. 13 has a truncated GAL-4 DNA-binding domain.

FIG. 8 depicts the amino acid sequences of the GENESWITCH® regulator proteins (SEQ. ID. NOS. 14 & 15) encoded by the coding sequences depicted in FIG. 7. SEQ. NOS. 12 & 13 respectively.

FIG. 9A depicts a schematic representation of relevant regions of an inducible promoter with unique restriction sites indicated. FIG. 9B depicts the nucleic acid sequence of the 6×GAL-4/TATA promoter region SEQ. ID. NO. 25, and FIG. 9C depicts the nucleic acid sequence of the TATA box, initiation ("inr") region and the UT12 Transcription factor binding site, SEQ. ID. NO. 17.

FIG. 10 depicts nucleic acid sequences of the inducible promoter regions of plasmids tested in development of an improved inducible promoter. SEQ. ID. NOS. 18, 19, 20, & 21.

FIG. 13 depicts the complete nucleic acid sequence of pGS1694, SEQ. ID. NO. 22.

FIG. 14 depicts the complete nucleic acid sequence of pEP1666, SEQ. ID. NO. 23.

FIG. 17 demonstrates the rapid onset of erythroid hypocythemia in mice with constitutive EPO expression using a CMV-hEPO plasmid. 75 mg of pEP1549 (CMV-hEPO) was formulated with sodium poly-L-glutamate and delivered with electroporation to both tibialis and gastrocnemius muscles of five mice.

FIG. 18 depicts the long-term regulation of a foreign transgene (human EPO) in mice using an improved expression-regulated system according to one embodiment of the present invention.

DETAILED DESCRIPTION OF THE PREFERRED EMBODIMENTS

With long term expression of gene products, and particularly in circumstances in which physiological effects are unpredictable, or are associated with adverse effects or toxicities, delivery of certain genes or gene products may require the ability to closely control expression of transfected genes from outside the body.

Figure 2:
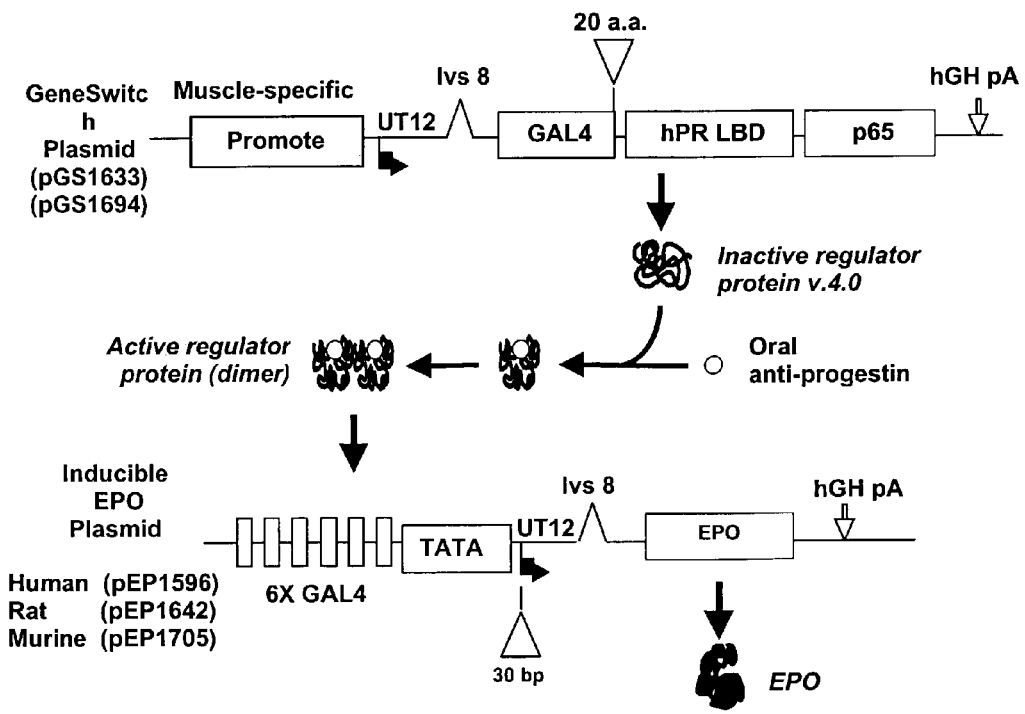
FIG. 2 is a schematic representation of the nucleic acid structures of an improved expression-regulated system comprising a GENESWITCH® regulator plasmid and an inducible EPO plasmid according to one embodiment of the present invention.

Ideally, control of transgene expression via a "molecular switch" should allow specificity, selectivity, precise timing and level of expression, safety, and rapid clearance of the triggering compound. According to one aspect of the present invention, a system for regulating gene expression is generally depicted in FIG. 2 using the EPO gene as an example. The "molecular switch" expression system is generally comprised of two nucleic acid or expression cassettes: (1) a molecular switch or otherwise called a GENESWITCH® plasmid, and (2) an inducible gene plasmid (e.g., Inducible EPO plasmid, inducible F.IX plasmid, inducible IFN plasmid). Although FIG. 2 suggests that the two nucleic acid cassettes are carried on two different plasmid vectors, the two nucleic acid cassettes may also be carried on two viral vectors or combined in a single plasmid vector or a single viral vector having both nucleic acid cassettes.

The term "molecular switch plasmids," as used herein, refers to plasmids encoding chimeric transcriptional regulator or "molecular switch" molecules or proteins having, but not limited to: 1) a sequence specific DNA binding domain (DBD) such as for example the GAL-4 DBD; 2) a mutated steroid receptor ligand binding domain such as for example a human progesterone receptor ligand binding domain having a C-terminal deletion of about 19-66 amino acids wherein the mutant may be activated in the presence of an antagonist for the naturally occurring or wild-type progesterone receptor; and 3) a transactivation domain, such as for example the herpes virus VP-16 or NFkappaB p65 transactivation domain. The transactivation domains may also be selected from a number of other transactivation domains known to those of skill in the art, such as for example, TAF-1, TAF-2, TAU-1, and TAU-2.

The term "GENESWITCH®" is a registered trademark of Valentis, Inc. and is used to identify "molecular switch plasmids," "molecule switch" proteins or molecules, and expression systems generated by Valentis, Inc. The prefix "pGS" is abbreviation identifying GENESWITCH® plasmids.

FIG. 2 generally depicts the interaction of the molecular-switch plasmid and proteins with the inducible gene plasmid. In general, the first expression cassette contained in the GENESWITCH® plasmid may comprise a promoter driving the expression of a fusion or chimeric protein. The promoter may be any promoter such as a CMV promoter or a tissue-specific promoter for expression in an animal cell. A preferred promoter for use with one aspect of the invention is a muscle-specific promoter with advantages as will be discussed below. The fusion or chimeric protein expressed from the fusion or chimeric gene generally comprises three structural domains represented by GAL-4, hPR LBD, and p65 in the GENESWITCH® plasmid in FIG. 2. These three domains also correlate to the functional domains of the fusion protein.

For example, GAL-4 represents nucleic acid sequence correlating to the GAL-4 DNA-binding domain responsible for the interaction or binding of the fusion protein to the GAL-4 sites in the inducible promoter of a second nucleic acid cassette, depicted as the inducible EPO plasmid. p65 represents nucleic acid sequence correlating to the transcription regulatory domain of the NFkappaB p65 protein.

The hPR LBD correlates to the ligand-binding domain of the fusion protein, which is responsible for the interaction of the fusion protein with a ligand represented by an oral anti-progestin in FIG. 2. In a specific example, the ligand-binding domain (LBD) is derived from the amino acid sequence correlating to the ligand-binding domain of human progesterone receptor (hPR), a receptor in the steroid-receptor family. As will be discussed in greater details below, the amino acid sequence in the LBD of hPR may be mutated to result in a mutated hPR LBD (or, more generally, a mutated steroid-receptor LBD) that selectively binds to the anti-progestin instead of progestin, the natural ligand/agonist of the progesterone receptor. Through a mutated hPR LBD, the fusion protein may, thus, be selectively activated by an anti progestin, instead of the naturally occurring progestin. Thus anti-progestins bind to the natural PR, but act as antagonists. Progestins bind to the natural PR and act as agonists. Progestins do not bind to the truncated PR and thus have no activity. The mutated PR retains the ability to bind anti-progestins, but now they act as agonists.

As shown generally in FIG. 2, when the anti-progestin binds to the fusion protein expressed from the GENESWITCH® plasmid, the fusion protein is activated and forms a dimer complex. The dimer/anti-progestin complex, in turn, binds to the promoter of the inducible EPO plasmid and transactivates the transcription of the EPO gene. It should be noted that the specific nucleic acid structures depicted in the two nucleic acid cassettes in FIG. 2 are provided as examples, and various modifications can be made to achieve a similarly tightly regulated expression system.

For example, the transregulatory domain represented by NFkappaBp65 may be substituted with various other trans-regulatory domains such as, for example, VP-16, TAF-1 and TAF-2 (Pham et al. Mol Endocrinol 1992 July; 6(7):1043-50), TAU-1 (Dahlman-Wright et al. (1994) Proc. Natl. Acad. Sci. U.S.A. 91, 1619-1623), TAU-2 (Milhon et al. Mol Endocrinol 1997 November; 11(12):1795-805), ORF-10 (Moriuchi et al. Proc Natl Acad Sci USA 1995 Sep. 26; 92(20):9333-7); TEF-1 (Hwang et al. EMBO J 1993 June; 12(6):2337-48) and any other nucleic acid/amino acid sequences having a transcription regulatory function. In one embodiment, the preferred transactivation domain is a human transactivation domain, such as for example NFkappaB p65, where relative humanization of the molecular switch protein is desired.

The DNA-binding domain and the corresponding 6×GAL-4 binding site in the inducible gene plasmid should not be seen as being limited to the modified GAL-4 DNA-binding domain described herein. Other DNA binding domains that have been altered to remove sequences that are not essential for recognition of binding sites but may be predicted to contribute to autodimerization by virtue of their secondary structure may also be used. Other DNA binding domains that may be so modified include for example the known DNA binding domains of the steroid-receptor family (e.g., glucocorticoid receptor, progesterone receptor, retinoic acid receptor, thyroid receptor, androgen receptor, ecdysone receptor) or other cellular DNA binding proteins such as the cAMP Response Element Binding protein (CREB) or zinc finger DNA binding proteins, such as SP1. The GAL-4 DNA-binding domain is preferred in one embodiment because it readily allows for greater control and selectivity of gene activation using this expression system in mammalian cells.

The steroid-receptor family of gene regulatory proteins is also ideal for the construction of molecular switches. Steroid receptors are ligand activated transcription factors whose ligands can range from steroids to retinoids, fatty acids, vitamins, thyroid hormones, and other presently unidentified small molecules. These compounds bind to receptors and either up-regulate or down-regulate the expression of steroid-regulated genes. The compounds are usually cleared from the body by existing mechanisms and are usually non-toxic. The term "ligand," as used herein, refers to any compound or molecule that activates the steroid receptor, usually by interaction with (binding) the ligand-binding domain (LBD) of the steroid receptor.

The term "steroid-hormone receptor" as used herein refers to steroid-hormone receptors in the superfamily of steroid receptors, some of which are known steroid receptors whose primary sequence suggests that they are related to each other. Representative examples of the steroid-hormone receptors include the estrogen, progesterone, glucocorticoid-α, glucocorticoid-β, mineralocorticoid, androgen, thyroid hormone, retinoic acid, retinoid X, Vitamin D, COUP-TF, ecdysone, Nurr-1 and orphan receptors. The receptors for hormones in the steroid/thyroid/retinoid supergene family, for example, are transcription factors that bind to target sequences in the regulatory regions of hormone-sensitive genes to enhance or suppress their transcription. These receptors have evolutionarily conserved similarities in a series of discrete structural domains, including a ligand binding domain (LBD), a DNA binding domain (DBD), a dimerization domain, and one or more trans-activation domain(s).

Various mutations or changes in the amino acid sequences of the different structural domains may be generated to form a mutated steroid receptor or, more specifically, mutated steroid-hormone receptor. The term "mutated steroid receptor," "modified steroid receptor," or a "mutated steroid-hormone receptor" or "modified steroid-hormone receptor," as used herein is a steroid receptor or steroid-hormone receptor that has been mutated in its amino acid sequences such that the mutated form is capable of preferentially binding to a non-natural or non-native ligand rather than binding to the wild type, or naturally occurring, hormone receptor ligand. Usually this mutation is generated in the ligand-binding domain of the steroid receptor and may be denoted as "mutated steroid-receptor LBD." A mutated steroid receptor has the property to activate transcription of a desired gene (such as a gene encoding erythropoeitin) in the presence of an antagonist for a wild type steroid hormone receptor protein.

Normally, a non-natural or non-native ligand may act as an antagonist or may have an antagonist effects to a wild-type steroid receptor or steroid-hormone receptor. "Antagonist" as used herein is a compound that interacts with or binds to a native steroid hormone receptor and blocks the activity of the agonist of the native steroid hormone receptor. "Agonist" as used herein is a compound that interacts with the wild type steroid hormone receptor to promote a transcriptional response.

For example, progesterone or progestin is an agonist for the progesterone receptor because progesterone normally binds to the progesterone receptor to activate the transcription of progesterone-regulated genes. Compounds, which mimic progesterone, would also be defined as progesterone receptor agonists. Mifepristone (MFP) or otherwise known as RU486 is a non-natural ligand that also binds to the progesterone receptor and competes with progesterone for binding. Although under certain special circumstances, MFP may slightly activate certain progesterone-regulated genes through the progesterone receptor, the amount of activation is minimal when compared to the major activity of MFP, which is to block the activation of the progesterone receptor by progesterone. Hence, in the presence of progesterone and the progesterone receptor, MFP exerts an antagonistic effect on the progesterone receptor because it blocks the normal activation of the receptor by progesterone.

The progesterone receptor may be mutated, e.g. in the ligand-binding domain of the progesterone receptor, such that it only binds to MFP and not to progesterone. The mutation of the ligand-binding domain of progesterone receptor may be such that binding of the MFP may actually activate the progesterone receptor under typical cellular conditions. When a mutated PR LBD, or more generally any other mutated steroid-receptor LBD, is combined as a fusion protein with a particular DNA-binding domain such as the GAL-4 DNA binding domain, binding of MFP selectively activates the fusion protein to transactivate gene expression driven by a promoter recognized by the DNA-binding domain. Thus, the mutated steroid receptor of the subject invention is not activated in the presence of agonists for the native receptor, but instead the mutated steroid receptors may be activated in the presence of "non-natural ligands."

The term "non-natural ligands" or "non-native ligands" refers to compounds which are normally not found in animals or humans and which bind to the ligand binding domain of a receptor. Examples of non-natural ligands and non-native ligands are anti-hormones that may include the following: 11β-(4-dimethylaminophenyl)-17β-hydroxy-17α-propynyl-4,9-estradiene-3-one (RU38486 or Mifepristone); 11β-(4-dimethylaminophenyl)-17α-hydroxy-17β-(3-hydroxypropyl)-13α methyl-4,9-gonadiene-3-one (ZK98299 or Onapristone); 11β-(4-acetylphenyl)-17β-hydroxy-17α-(1-propynyl)-4,9-estradiene-3-one (ZK112993); 11β-(4-dimethylaminophenyl)-17β-hydroxy-17α-(3-hydroxy-1(Z)-propenyl-estra-4,9-diene-3-one (ZK98734); (7β,11β,17β)-11-(4-dimethylaminophenyl)-7-methyl-4',5'-dihydrospiro [ester-4,9-diene-17,2'(3'H)-furan]-3-one (Org31806); (11β,14β,17α)-4',5'-dihydro-11-(4-dimethylaminophenyl)-[spiroestra-4,9-diene-17,2'(3'H)-furan]-3-one (Org31376); 5-α-pregnane-3,20-dione, Org 33628 (Kloosterboer et al. Ann N Y Acad Sci 1995 Jun. 12; 761:192-201), Org 33245 (Schoonen et al. J Steroid Biochem Mol Biol 1998 February; 64(3-4):157-70).

"Mutant," "mutation," "mutated," "modified," or "modification" refers to an alteration of the primary sequence of a receptor or any other gene or protein such that it differs from the wild type or naturally occurring sequence. For example, a mutant, mutated or modified steroid-hormone receptor protein as used in this disclosure can be a mutant of any member of the steroid-hormone receptor superfamily. For example, a steroid receptor can be mutated by addition of amino acid(s), substitution of amino acid(s) or deletion of amino acid(s). Preferably, the deletion of the amino acids occurs on the carboxy terminal end of the protein. Generally, a deletion of from about 1 to about 120 amino acids from the carboxy terminal end of the protein provides a mutant useful in the present invention. A person having ordinary skill in this art will recognize, however, that a shorter deletion of carboxy terminal amino acids will be necessary to create useful mutants of certain steroid hormone receptor proteins. For example, a mutant of the progesterone receptor protein will contain a carboxy terminal amino acid deletion of from about 1 to about 60 amino acids. In another embodiment, 19 carboxy terminal amino acids are deleted from the progesterone receptor protein.

Furthermore, a mutated steroid-hormone receptor LBD may be selected based on the ability of an antagonist for the wild-type steroid-hormone receptor to activate the mutant receptor even in the presence of an agonist for the wild-type receptor. Thus, in the case of the progesterone receptor, progesterone is the normal ligand and functions as a strong agonist for the receptor. The anti-progestin, mifepristone (RU486), is a non-natural or non-native ligand for the progesterone receptor. Mifepristone (MFP) is considered an "anti-progestin" because, although it is able to exert a slight agonist effect on the wild-type progesterone receptor, MFP inhibits the strong agonistic effects of progesterone. Thus, MFP may be considered an "antagonist" for the wild-type progesterone receptor when in the presence of the normal agonist, i.e. when both MFP and progesterone are together in the presence of the wild-type progesterone receptor. In contrast, in one example of a mutated steroid-hormone receptor according to the invention, the mutated progesterone receptor is not activated by progesterone (agonist for the wild type receptor) but is activated in the presence of MFP ("antagonist" for the wild type receptor). In addition, progesterone is not able to block the activation of the mutated steroid-hormone receptor by MFP. Thus, the mutated receptor may be characterized as activated when bound to an antagonist (MFP) for the wild-type receptor even in the presence of an agonist (progesterone) for the wild-type progesterone receptor.

Further examples of mutated and modified steroid-hormone receptor for used with the current invention are described in, for example: (1) "Adenoviral Vector-Mediated Delivery of Modified Steroid Hormone Receptors and Related Products and Methods" International Patent Publication No. WO0031286 (PCT/US99/26802); (2) "Modified Glucocorticoid Receptors, Glucocorticoid Receptor/Progesterone Receptor Hybrids" International Patent Publication No. WO9818925 (PCT/US97/19607); (3) "Modified Steroid Hormones for Gene Therapy and Methods for Their Use" International Patent Publication No. WO9640911 (PCT/

US96/0432); (4) "Mutated Steroid Hormone Receptors, Methods for Their Use and Molecular Switch for Gene Therapy" International Patent Publication No. WO 9323431 (PCT/US93/0439); (5) "Progesterone Receptors Having C-Terminal Hormone Binding Domain Truncations", U.S. Pat. No. 5,364,791; (6) "Modified Steroid Hormone Receptors, Methods for Their Use and Molecular Switch for Gene Therapy" U.S. Pat. No. 5,874,534; and (7) "Modified Steroid Hormone Receptors, Methods for Their Use and Molecular Switch for Gene Therapy" U.S. Pat. No. 5,935,934, all of which are incorporated herein by reference in their entirety, including any drawings.

Although the examples provided in this disclosure use plasmid-based mutated steroid hormone receptor system, viral-based versions of a mutated steroid hormone receptor system according to the present invention may also be used to regulate gene expression in vitro or in vivo. There are several specific examples of the use of early versions of inducible transcriptional regulator system in viral vectors. For example: (1) the positive and negative regulation of gene expression in eukaryotic cells with an inducible transcriptional regulator is described in Wang, et al., Gene Therapy, 4: 432-441, 1997; and (2) drug inducible transgene expression in brain using a herpes simplex virus vector is described in Oligino, et al., Gene Therapy, 5: 491-496, 1998. These above examples may be applied to provide for viral-based regulated gene-expression systems according to the present invention.

To improve the tightness of regulated expression, several aspects of the GENESWITCH® expression cassette and the inducible therapeutic molecule expression cassette were modified. First, the transcribed portion of the GENESWITCH® expression cassette was modified to include post-transcriptional elements (5' UTR, synthetic intron and poly(A) signal) that improve the level and fidelity of transgene expression. Second, the structure of the GENESWITCH® regulatory protein was modified. The regulator protein appears to have a propensity, in the absence of ligand, to form dimers that could bind GAL-4 sites in the inducible promoter and thereby partially activate transcription. To minimize this possibility, truncation or mutation on the GAL-4 domain of the regulator protein may be made such as deleting from the C-terminal portion of the GAL-4 DBD, about 20 residues, thereby reducing the length of a coiled-coil structure that was predicted to contribute to GAL-4 homodimer formation. GENESWITCH® regulator protein v.4.0 embodies this modification. Third, the CMV promoter of the GENESWITCH® expression cassette may be replaced with a tissue-specific promoter such as avian skeletal alpha-actin promoter, which is muscle-specific. Under certain circumstances the muscle specific may be more or less active than the CMV promoter in muscle tissue.

The inducible therapeutic molecule expression plasmid may be also that modified in the core region of the inducible promoter. It has been found that delivery of 75 micrograms of the original inducible mEPO plasmid (pEP1442) by itself (in the absence of the GENESWITCH® plasmid) caused hematocrit level in mice to increase to 50% or greater. It was then determined that a deletion in the transcription initiation region of the inducible EPO plasmid can reduce the intrinsic activity of the promoter by approximately 10-fold without impairing its ability to be induced. When tested in combination with an improved GENESWITCH v.4.0 plasmid in transfected COS-1 cells, the level of basal expression was reduced 8-fold and the level of induced expression remained essentially unchanged. It should be noted that the modifications described above may be employed independently or in combination with each other depending on the desired effect.

In one embodiment of the present invention, a molecular switch protein comprising a chimeric receptor having a mutated progesterone-receptor ligand-binding domain, a truncated GAL-4 DNA binding domain, and a VP16 or p65 transregulatory domain is disclosed. The p65 transregulatory domain is part of the activation domain of the human p65 protein, a component of the NFkappaB complex. By replacing VP16 with a variety of human-derived activation domains such as, for example, residues 286-550 of the human p65, the potent inducibility of the chimeric receptor can be retained while "humanizing" the protein or reducing the potential for a foreign protein immune response due to the viral VP16 component. In the presence of the anti-progestin MFP (RU486), this chimeric regulator binds to a target nucleic acid sequence containing a 17-mer GAL-4 binding site, and results in an efficient ligand-inducible transactivation of the target gene downstream of the GAL-4 binding site. The modified steroid-hormone ligand-binding domain of the receptor protein may also be modified by deletion of carboxy terminal amino acids, preferably, from about one to one hundred-twenty carboxy terminal amino acids. The extent of deletion desired can be modulated according to conventional molecular biological techniques to achieve both selectivity for the desired ligand and high inducibility when the ligand is administered. In one embodiment, the mutated steroid hormone receptor LBD is mutated by deletion of about one to about sixty carboxy terminal amino acids. In another embodiment forty-two carboxy terminal amino acids are deleted. In yet another embodiment, having both high selectively and high inducibility, nineteen carboxy terminal amino acids are deleted.

Figure 5:
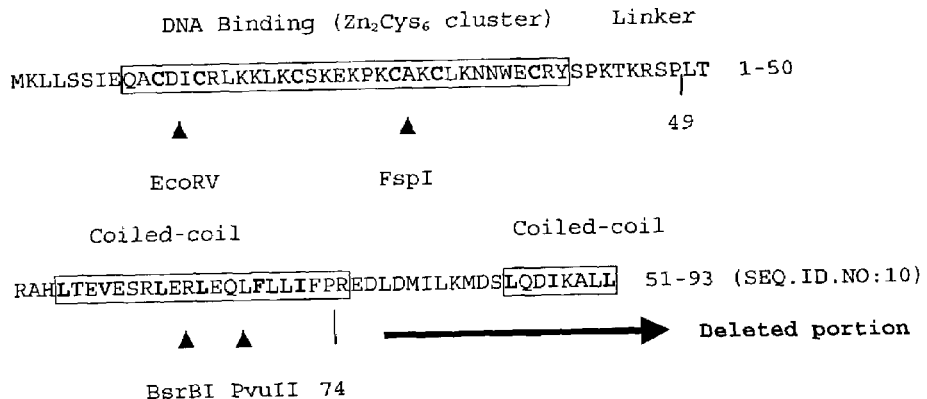
FIG. 5 depicts the amino acid sequence and structure of the GAL-4 DNA binding domain, amino acid residues 1-93. SEQ. ID. NO. 10.

As used herein, the GAL-4 DNA Binding Domain ("GAL-4 DBD") refers to amino acids 1-93 of the N-terminal DNA binding domain of GAL-4 as shown in FIG. 5 SEQ. ID. NO. 10. As used herein, a "modified GAL-4 DBD" or mutated GAL-4 DBD refers to a GAL-4 DBD that has a mutation in the primary amino acid structure, or to a amino acid sequence derived from the GAL-4 DBD, that retains the ability to bind to the canonical 17-mer binding site, CGGAA-GACTCTCCTCCG, (SEQ.ID. NO. 9), but has a reduced ability to form a helical tertiary structure needed for auto-dimerization. In one example, a deletion of a region represented by amino acids 75 to 93 of the native GAL-4 DBD as depicted in FIG. 5, provides for a modified or mutated GAL-4 DBD that when combined with the GENESWITCH® regulator protein decreases the basal expression of EPO from an inducible expression plasmid. Other mutations or deletions may also be made to the region spanning amino acid sequence 54-74 of the GAL-4 DBD as shown in FIG. 5. For example, a deletion of amino 54-64, or 65-75 may be made such that autodimerization through the coiled coil region is minimized.

In one example, an optimized transgene regulation system is disclosed below which meets desired criteria for a robust system. In particular, an improved regulated muscle-specific EPO/GENESWITCH® system disclosed in one embodiment herein provides an undetectable biological effect from a pharmacological dose of introduced erythropoietin transgene in the absence of inducer. By "biological effect" it is meant that, although it may be possible to detect the production of messenger RNA by ultra sensitive assays such by Polymerase Chain Reaction ("PCR"), no physiologic effect, such as for example in the cases of EPO, no rise in hematocrit, is observed. In one experiment using the most sensitive measurement of basal EPO expression, i.e., an increase in hematocrit level, the increase did not occur in mice with the improved mEPO/GENESWITCH® system, in rats with the rEPO/GENESWITCH® system, or in mice with hEPO/GE- NESWITCH® system, even at plasmid doses (7.5 mg/Kg body weight) that greatly exceed those projected to be used in humans. In addition, serum levels of hEPO were undetectable in the absence of inducing drug when plasmids were delivered to dogs at 3.5 mg/Kg.

On the other hand, the improved system responded to doses of MFP as low as 0.01 mg/Kg and stable increases in hematocrit were maintained by a chronic dosing schedule. Responsiveness to low doses of MFP is highly favorable; especially since chronically administered 25 mg doses (0.25-0.5 mg/Kg) are well tolerated in humans.

The kinetics of induction in response to oral MFP dosing was also rapid. In mice, peak expression occurs within 24 hours, and in dogs, peak expression occurs within 48 hours. In mice, baseline expression levels were restored after 72-96 hours after cessation of MFP treatment. In dogs, near baseline levels of expression were observed 3 days after cessation of MFP treatment. Responses following a single administration of plasmid were also durable and consistent. The consistency in the kinetics and peak levels for each of the four cycles of hEPO induction over an 8-month period in mice is a particularly good example.

The improved system may also be scalable to larger animals. In dogs, for example, inducible EPO expression occurred at plasmid doses of 0.5-3.5 mg/Kg. In rats, plasmid doses as low as 0.03 mg/Kg were also sufficient.

No evidence for immunogenicity or toxicity due to expression of the chimeric GENESWITCH® regulator protein was found. The ability of the improved plasmid-based system to avoid neutralizing immune responses and thereby achieve long-term (8-month) regulated expression of a foreign transgene (human EPO) in a majority of mice is a surprising finding. Tight expression control may permit a pulsatile program of transgene expression that may deprive the immune system of a source of antigen at certain critical times. The control of neutralizing immune responses to foreign transgene products is directly relevant to the treatment of genetic deficiencies, like hemophilia A or B in which the normal protein can appear to be a foreign antigen. The above benefits of the presently disclosed improved regulated EPO/GE-NESWITCH® system represent an important advance in gene therapy.

The improved system may also have several optional components that permit advantages over existing systems. First, the present improved GENESWITCH® regulator protein is mostly humanized (86%) (amino acid sequences derived from human proteins except for the GAL-4 DNA-binding domain), thus reducing the potential for long-term immune responsiveness to the system in immune-competent recipients.

Second, exogenous control of expression in the present system having undetectable baseline expression may also permit a lag time prior to first induction by MFP or other inducer. The length of the lag period between plasmid delivery and the first induction of transgene expression permits reduction in the potential for developing immune responses to the expressed transgene. Delivery of plasmids with electroporation, for example, is associated with transient inflammation and cellular infiltration that are able to activate dendritic cell maturation. Foreign transgene expression that is induced after inflammation at the muscle site has subsided avoids transgene expression in a hyperinflammatory environment. Third, use of a muscle-specific promoter may also provide low level GENESWITCH® protein production and may minimize expression in non-muscle cells.

An IFN gene therapy is an attractive potential therapy for a number of indications including cancer and chronic viral infections. Sequences for a number of different interferons, including interferon beta, gamma, omega and over 20 interferon alpha species, some of which may be pseudogenes, can be found in GenBank (for example, the reference sequence of interferon alpha 2 NM_000605). Variants of human leukocyte interferon alpha 2 (IFN-alpha 2a, alpha 2b, and alpha 2c) differ from each other by changes in their coding regions at nucleotide positions 137 and 170. IFNalpha2b has been determined to be a predominant species among the alpha 2 interferons, however the present invention is applicable to and encompasses regulated expression of any one of the naturally occurring, modified or synthetic interferons.

For chronic hepatitis C infection, current therapies with recombinant IFN-alpha protein and PEGylated forms of IFN-alpha are partially effective and require combination treatment with ribavirin. Advantages of PEGylated IFN-alpha are reduction in the frequency of injection from 3× to 1× weekly, and improvement in therapeutic response. However, all of the routinely injected IFN-alpha protein therapies are associated with substantial side effects.

The elimination half-life of recombinant and pegylated INF-alpha proteins in humans is 4.8-7.2 h and 27-39 h, respectively. From published pharmacokinetic data on PEG-Intron A in humans (Glue et al, 2000, Hepatol. 32:647; Glue et al, 2000, Clin Pharm Ther 68:556), it is calculated using a conversion factor (1 unit=3.714 picogram; 1 picogram=0.269 units), that continuous expression of ~100 pg/ml should provide the same area under the curve of serum interferon levels as weekly treatments with PEGylated interferon alpha. This value probably defines the upper limit, as continuous infusion of non-pegylated INF-alpha protein in hepatitis C patients yielded therapeutic benefit at circulating levels of ~15 pg/ml (Schenker et al., 1997, J. Int. Cyt. Res. 17:665; Smith et al., 1987, Canc. Chemother. Pharmacol. 20:327). Moreover, the side effects resulting from continuous infusion were lesser in intensity than those resulting from intermittent dosing, particularly when circulating levels were less than 200 pg/ml.

Plasmid encoding human interferon alpha (hIFN-alpha) was injected into the tibialis of mice followed by administration of electrical pulses (electroporation) to facilitate plasmid uptake. Using a plasmid driven by the CMV enhancer/promoter and injected plasmid doses of 1.0 micrograms to 100 micrograms, a dose response of hIFN-alpha expression was achieved with peak levels of 16,458±897 pg/ml with electroporation. Expression without electroporation was approximately 70-fold lower (238±100 pg/ml). The ability to tightly regulate expression of an interferon gene therapy is expected to be a key component of the safety profile. Accordingly, hIFN-alpha was expressed in mice using the GENESWITCH® regulatory system. A two plasmid mixture was injected into the tibialis of mice. One plasmid encoded the GENESWITCH® protein under control of the skeletal actin promoter and the other plasmid encoded for hIFN-alpha containing the GAL4 binding sites linked to a consensus TATA box. Using this system hIFN-alpha levels peaked ~24 hours after administration of mifepristone, the low molecular weight inducer. In mice, a pulsatile pattern of hIFN-alpha expression was achieved in CD-1 mice for more than 30 days. Mean peak levels of hIFN-alpha protein exceeded 200 pg/ml. In C57BL/6 mice, mean peak levels of hIFN-alpha protein exceeded 400 pg/ml and pulsatile regulation was achieved for ~100 days.

The term "expression cassette" or "nucleic acid cassette," as used herein refers to the combination of nucleic acid sequences involved in expression of a particular functional product. This functional product is typically a protein although it could also be a nucleic acid such as for example, an RNA molecule such as a ribozyme or antisense RNA. The expression cassette may also be comprised of a number of non-coding elements in addition to sequences encoding a product such as a protein. Non-coding elements are nucleic acid sequences bounded or defined by consensus sequences or having a contextual location identifiable or recognized by those of skill in the art. A "5' untranslated region" or "5' UTR" refers to a sequence located 3' to promoter region and 5' of the coding region. For example, the 5' end of the 5' UTR is typically defined as the transcription start site. Although the start of transcription may not be precisely known, it is often estimated to be approximately 30 base pairs 3' of the end of the TATA box. The 3' end of the 5' UTR would be defined as the base immediately 5' to the start codon (ATG). Thus, such a sequence, while transcribed, is upstream of the translation initiation codon and therefore is not translated into a portion of the polypeptide product. Such a 5' UTR may also have an intron within it. In one embodiment of the present invention, the expression cassette includes: promoter sequences, transcription start sequences, 5' untranslated ("5' UTR") sequences, coding sequences from a start codon through a stop codon, and 3' untranslated sequences ("3' UTR") including polyadenylation sequences. As used herein the 5' UTR may include one or more functional non-coding elements able to increase the level and fidelity of expression. As used herein, the 5' UTR may include intron sequences that are transcribed and present in pre-messenger RNA ("pre-mRNA"), but are removed by splicing and are absent in the mature messenger RNA ("mRNA").

The term "intron" as used herein refers to a sequence encoded in a DNA sequence that is transcribed into an RNA molecule by RNA polymerase but is removed by splicing to form the mature messenger RNA. A "synthetic intron" refers to a sequence that is not initially replicated from a naturally occurring intron sequence and generally will not have a naturally occurring sequence, but will be removed from an RNA transcript during normal post-transcriptional processing. Such synthetic introns can be designed to have a variety of different characteristics, in particular such introns can be designed to have a desired strength of splice site and a desired length. In a preferred embodiment of the present invention, both the molecular switch expression cassette and the therapeutic gene expression cassette include a synthetic intron. The synthetic intron includes consensus sequences for the 5' splice site, 3' splice site, and branch point. When incorporated into eukaryotic vectors designed to express therapeutic genes, the synthetic intron will direct the splicing of RNA transcripts in a highly efficient and accurate manner, thereby minimizing cryptic splicing and maximizing production of the desired gene product.

A "therapeutic molecule" or "therapeutic gene" is one that has a pharmacologic activity when administered appropriately to a mammal suffering from a disease or condition. Such a pharmacological property is one that is expected to be related to a beneficial effect on the course or a symptom of the disease or condition. The term "therapeutic protein" as used herein refers to the native, full-length secreted form of a therapeutic protein, as well as to analogs or derivatives thereof comprising single or multiple amino acid substitutions, deletions or additions that retain native therapeutic protein function or activity. Sequences encoding therapeutic proteins may include codon optimized versions of native sequences. Optimal codon usage in humans is indicated by codon usage frequencies for highly expressed human genes and may be determined from the program "Human High-.codN" from the Wisconsin Sequence Analysis Package, Version 8.1, Genetics Computer Group, Madison, Wis. The codons that are most frequently used in highly expressed human genes are presumptively the optimal codons for expression in human host cells, and thus form the basis for constructing a synthetic coding sequence.

The term "plasmid" as used herein refers to a construction comprised of extrachromosomal genetic material, usually of a circular duplex of DNA that can replicate independently of chromosomal DNA. Plasmids may be used in gene transfer as vectors.

The term "vector" as used herein refers to a construction comprised of genetic material designed to direct transformation of a targeted cell. A vector may contain multiple genetic elements positionally and sequentially oriented with other necessary elements such that an included nucleic acid cassette can be transcribed and when necessary translated in the transfected cells. As used herein the term "expression vector" refers to a DNA plasmid that contains all of the information necessary to produce a recombinant protein in a heterologous cell.

"Erythropoietin", or "EPO," as used herein, refers to a glycoprotein hormone produced in fetal liver and adult kidney that acts to stimulate the formation of red blood cells from progenitor cells in the bone marrow and other hematopoietic tissue. Genes encoding human and other mammalian EPOs show a high degree of sequence homology in the coding region. (Wen et al. Blood 82:1507(1993)). The sequence of the gene encoding native human EPO, including methods of obtaining such sequences, are described in, for example among others: U.S. Pat. Nos. 4,954,437 and 4,703,008; Shoemaker, U.S. Pat. No. 4,835,260; Sytkowski and Grodberg, U.S. Pat. Nos. 6,153,407 and 5,614,184); Sytkowski, U.S. Pat. No. 5,580,853; Mellovitz, U.S. Pat. Nos. 5,888,772 and 5,457,089; Fibi and Powell, U.S. Pat. No. 5,688,679; Jacobs et al., Nature 313:806-810 (1985); Lin et al. Proc. Natl. Acad. Sci. USA 82:7580 (1985); International Publication Number WO 85/02610; and European Patent Publication Number 232,034 B1, all of which are hereby incorporated herein by reference in their entirety.

The sequences of the genes encoding other mammalian EPOs such as for example feline (GenBank Acc. No.: L10606), canine (GenBank Ace. No.: L13027); porcine EPO (GenBank Acc. No.: L10607), and monkey (Macaca mulatta) (GenBank ace. No.: L10609) are also known.

The term "pharmacological dose" as used herein with a vector/molecular switch complex refers to a dose of vector and level of gene expression resulting from the action of the promoter on the nucleic acid cassette when introduced into the appropriate cell type which will produce sufficient protein, polypeptide, or antisense RNA to either (1) increase the level of protein production, (2) decrease or stop the production of a protein, (3) inhibit the action of a protein, (4) inhibit proliferation or accumulation of specific cell types, or (5) induce proliferation or accumulation of specific cell types. The dose will depend on the protein being expressed, the promoter, uptake and action of the protein or RNA. The term "pharmacological dose" as used herein with a ligand refers to a dose of ligand sufficient to cause either up-regulation or down-regulation of the nucleic acid cassette. Thus, there will be a sufficient level of ligand such that it will bind with the receptor in the appropriate cells in order to regulate expression from the nucleic acid cassette. The specific dose of any ligand will depend on the characteristics of the ligand entering the cell, binding to the receptor and then binding to the DNA and the amount of protein being expressed and the amount of up-regulation or down-regulation needed.

In a plasmid based expression system, a non-viral gene medicine may also be composed of a synthetic gene delivery system in addition to the nucleic acid encoding a gene product (e.g., a therapeutic protein). The non-viral gene medicine products are generally intended to have low toxicity due to the use of synthetic components for gene delivery (minimizing for instance the risks of immunogenicity generally associated with viral vectors) and non-integrating plasmids for gene expression. Since no integration of plasmid sequences into host chromosomes has been reported in vivo to date, they should neither activate oncogenes nor inactivate tumor suppressor genes. This built-in safety with non-viral systems contrasts with the risks associated with the use of most viral vectors. As episomal systems residing outside the chromosomes, plasmids have defined pharmacokinetics and elimination profiles, leading to a finite duration of gene expression in target tissues.

Formulating the nucleic acid with non-ionic and anionic polymers is particularly desirable because the polymers enhance transfection and expression of the nucleic acid, protect the nucleic acid from degradation, and are biodegradable. In addition, because formulating the nucleic acid with non-ionic anionic polymers results in more efficient transfection, lower amounts of DNA may be used. By biodegradable, it is meant that the polymers can be metabolized or cleared by the organism in vivo without any or minimal toxic effects or side effects. The term "anionic polymers" means polymers having a repeating subunit which includes, for example, an ionized carboxyl, phosphate or sulfate group having a net negative charge at neutral pH. Examples of the anionic polymers include poly-amino acids (such as poly-glutamic acid, poly-aspartic acid and combinations thereof), poly-nucleic acids, poly-acrylic acid, poly-galacturonic acid, and poly-vinyl sulfate. In the case of polymeric acids, the polymer will typically be utilized as the salt form. Examples of other polymers include PVP, PVA, chitosan, etc.

The term "poly-L-glutamic acid" is used interchangeably herein with "poly-L-glutamic acid, sodium salt", "sodium poly-L-glutamate" and "poly-L-glutamate." "Poly-L-glutamate" refers to the sodium salt of poly-L-glutamic acid. Although the L stereoisomer of polyglutamic acid has been primarily employed, the other stereoisomer or racemic mixtures of isomers are within the scope of the invention. The present invention contemplates that other salts of anionic amino acid polymers may be equally suitable.

The term "anionic amino acid polymers" means polymeric forms of a given anionic amino acid such as, for example, poly-glutamic acid or poly-aspartic acid. The present invention contemplates that polymers formed of a mixture of anionic amino acids, such as for example glutamic acid and aspartic acid, may be equally suitable.

Efforts have been made to enhance the delivery of plasmid DNA to cells by physical means including electroporation, sonoporation and pressure. Injection by electroporation is a modern technique that involves the application of a pulsed electric field to create transient pores in the cellular membrane without causing permanent damage to the cell and thereby allows for the introduction of exogenous molecules. This technique has been used widely in research laboratories to create hybridomas and is now being applied to gene transfer approaches for therapy. By adjusting the electrical pulse generated by an electroporetic system, nucleic acid molecules can find their way through passageways or pores in the cell that are created during the procedure. U.S. Pat. No. 5,704,908 describes an electroporation apparatus for delivering molecules to cells at a selected location within a cavity in the body of a patient. (U.S. Pat. No. 5,704,908, including any drawings contained therein, is hereby incorporated by reference as if fully set forth herein.)

The term "pulse voltage device", or "pulse voltage injection device" as used herein relates to an apparatus that is capable of causing or causes uptake of nucleic acid molecules into the cells of an organism by emitting a localized pulse of electricity to the cells, thereby causing the cell membrane to destabilize and result in the formation of passageways or pores in the cell membrane. It is understood that conventional devices of this type are calibrated to allow one of ordinary skill in the art to select and/or adjust the desired voltage amplitude and/or the duration of pulsed voltage and therefore it is expected that future devices that perform this function will also be calibrated in the same manner. The type of injection device is not considered a limiting aspect of the present invention. The primary importance of a pulse voltage device is, in fact, the capability of the device to facilitate delivery of compositions of the invention into the cells of an organism. The pulse voltage injection device can include, for example, an electroporetic apparatus as described in U.S. Pat. Nos. 5,439,440, 5,704,908 or 5,702,384 or as published in PCT WO 96/12520, PCT WO 96/12006, PCT WO 95/19805, and PCT WO 97/07826, all of which are incorporated herein by reference in their entirety.

EXAMPLE 1

Plasmid Delivery and Induction

For some experiments, inducible EPO (mouse, rat or human) and GENESWITCH® plasmids were mixed in a 1:1 ratio and formulated with 6 mg/ml sodium poly-L-glutamate (Sigma, St. Louis, Mo.) and 0.15 M NaCl. The maximal plasmid concentration of the formulated material was 1.5 mg/ml. Formulated plasmids were delivered to mouse and rat hind-limb muscles with 1.5 and 2.0 $cm^2$ size plate electrodes. Female C57BL/6 mice (18-20 g) were purchased from Harlan Sprague-Dawley.

Plasmid mixtures in saline or polymers were injected into bilateral hind-limb muscles (150 microliters total volume: 25 microliters per tibialis cranialis, 50 microliters per gastrocnemius) by direct injection. Two minutes later, the injected hind-limb muscles were subjected to electroporation using two stainless-steel parallel-plate-caliper electrodes connected to an Electro Square Porator™, Model T820, and BTX Enhancer™ 400 oscilloscope (BTX Division of GeneTronics, Inc., San Diego Calif.). The electrodes were placed noninvasively in contact with the skin of the leg (plate separation distance of 3 or 4 mm) and two square wave pulses were applied at 375 V/cm (pulse duration 25 ms). These electroporation conditions yielded elevated levels of transgene expression and improved reproducibility.

Mifepristone (Sigma) was either dissolved in sesame oil and administered in a 100 microliter volume (intraperitoneally or orally) or implanted subcutaneously as a pellet using a 10-gauge Precision Trochar (Innovative Research of America, Sarasota, Fla.). Blood was collected by retroorbital bleeds. Serum samples were assayed for SEAP activity, hVEGF, or EPO protein levels by ELISA (R & D Systems). All procedures conformed to state and federal guidelines.

For delivery to dog muscles, 1:1 mixture of plasmids formulated in poly-L-glutamate were injected, using 2 ml per site, into two (bilateral semimembranosus) or six (bilateral semimembranosus, semitendanosus and triceps) muscle sites of adult dogs (3-7 kg in body weight). Two minutes following injection, each site was subjected to electroporation with a 6-needle electrode array that consisted of six 22G needles arranged in a circle of 1.0 cm diameter and 1 cm length. Electroporation conditions were 200 V/cm, 6 pulses of 60 ms duration, with 1 second between pulses, and polarity was rotated following each pulse. The 6-needle electrode array, Electro Square Porator™, model T820, and Enhancer™ 400 Graphic Pulse Display were from BTX Division of Genetronics, Inc. (San Diego, Calif.).

Determination of Expression Levels

Murine and rat blood was collected by retro-orbital methods. Canine blood was collected by venipuncture of the jugular vein. Whole blood was used for hematocrit measurements and serum was used for EPO assays by the R&D Systems ELISA Quantikine kit (R&D Systems, Minneapolis, Minn.).

Quantities of mEPO plasmid DNA in murine muscles were determined by TaqMan® real time quantitative PCR (Applied Biosystems, Foster City, Calif.) as described in Mahato, R. I. et al., Hum. Gene Ther. 9:2083 (1998). The forward primer was from the 5' untranslated region, and the reverse primer was from the murine EPO coding region. CMV-mEPO plasmid DNA was used to generate a standard curve.

For measuring human EPO, an indirect ELISA technique using rhEPO (R&D Systems, Minneapolis, Minn.) as the target antigen was used according to Urra, J. M., et al., Clin. Chem. 43:848 (1997).

Test of significance between groups were performed by One-Way ANOVA analysis (SPSS Base 9.0, Chicago, Ill.). P values<0.05 were considered significant.

EXAMPLE 2

Expression of Erythropoietin in a Regulated Expression System

Experiments were conducted to assess the ability of various GENESWITCH® plasmids to regulate the long-term expression of a transgene, in particular, the erythropoietin (EPO) gene. The first GENESWITCH® system tested (GENESWITCH® version v.3.1 ("GSv3.1")), was comprised of the pGS1158 (CMV-GENESWITCH® v.3.1 gene) and the pEP1442 (inducible murine EPO (mEPO) gene). The pGS1158 plasmid is comprised of a nucleic acid cassette having a CMV promoter driving the expression of a fusion protein; the fusion protein being comprised of a NFkappaBp65 transactivation domain amino acids 285-551 ("p65"), a 92 amino-acid yeast GAL-4 sequence specific DNA binding domain ("GAL-$4_{2-93}$"), and a mutant progesterone receptor ligand-binding domain lacking a C-terminal 19 amino acids ("hPR$_{640-914}$ LBD"). The nucleic acid coding sequence for the GENESWITCH® v.3.1 protein is shown in FIG. 7, SEQ. ID. NO. 12 and the amino acid sequence in the FIG. 8, SEQ. ID. NO. 14.

A mixture of pEP1442 (coding for a codon optimized murine erythropoietin (mEPO) gene expressed from the inducible 6×GAL-4/TATA promoter) and pGS1158 (CMV-GSv.3.1, includes a CMV promoter, a SV40 intron located within the 3' UTR and a SV40 polyadenylation signal) was delivered to murine skeletal muscle with electroporation, and monitored for the inducibility of mEPO expression by oral doses of MFP.

Figure 1:
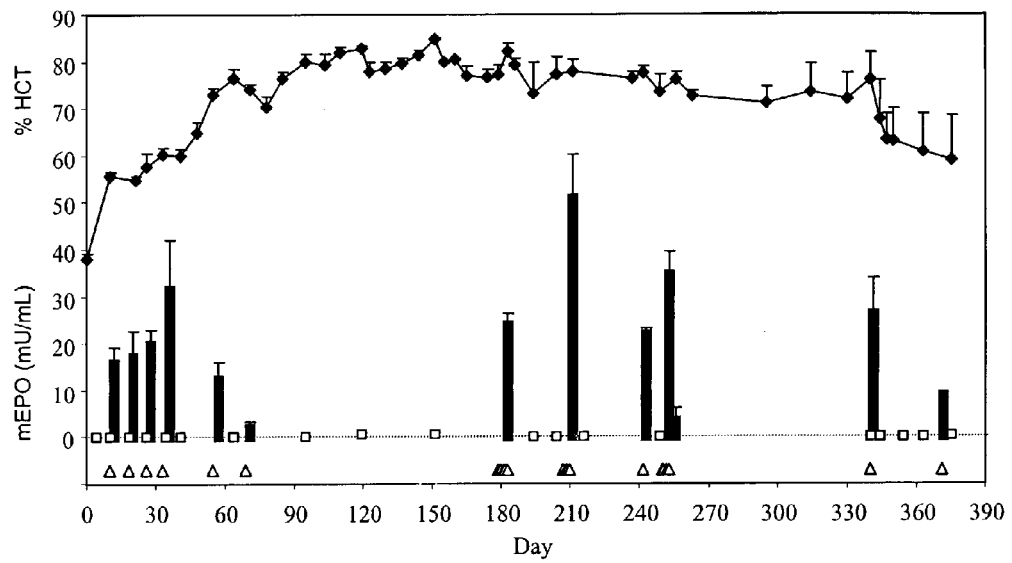
FIG. 1 depicts the regulation of murine EPO expression in mice for 1 year using a prior expression-regulated system.

FIG. 1 shows the regulation of murine EPO expression in mice for 1 year using the GENESWITCH® version 3.1 expression system. Briefly, a 1:1 mixture of the pEP1442 (inducible mEPO) and pGS1158 at total dose of 150 micrograms, was delivered with electroporation to both tibialis and gastrocnemius muscles of three mice on day 0. MFP (0.3 mg/Kg) was administered on the days indicated by the open triangles (Δ). Serum mEPO levels were measured 24 hours after single MFP doses or on the fifth day of 5 daily doses. Detectable mEPO levels are indicated by filled bars; undetectable levels by open squares (□). The level of mEPO on day 69 is lower than expected, because the serum sample was inadvertently collected after 72 hours. Hematocrit levels are indicated by filled diamonds (♦). All data points are mean±SEM. Similar patterns of mEPO induction (total of 11 induction cycles) occurred at various times throughout the 1-year period in response to single or multiple doses of MFP. Quantitative PCR was also used to measure the amount of plasmid retained in muscles harvested on day 413. The average amount of mEPO plasmid per animal was 14±6 pg (approximately 4 million copies).

As seen in FIG. 1, administration of MFP on day 7 induced mEPO expression; serum levels of mEPO appeared within 24 hours, and returned to undetectable levels within four days. Importantly, and as is apparent from FIG. 1, although long-term inducibility of mEPO expression in response to MFP dosing was achieved, regulation of hematocrit level was not achieved. The level of hematocrit did not diminish significantly during the 1-year period. For example, an increase in hematocrit level occurred prior to the first dose of MFP, and elevated levels of 60-80% were maintained regardless of when or how often mEPO expression was induced (FIG. 1). Thus, although mEPO was not detectable by ELISA, the amount of EPO produced was nonetheless sufficient to induce a maximal rise in hematocrit level.

Similarly, in in vitro experiments, significant transgene expression in the absence of mifepristone (MFP) was also observed, although the induction levels over background nonetheless exceeded 100-fold in some cell lines. Thus, these sensitive in vitro and in vivo experiments revealed that the EPO transgene was being expressed even in the absence of an inducer (MFP).

This data also suggest that the hematocrit level is a particularly sensitive indicator of basal expression of EPO due to the ability of EPO to induce changes in hematocrit even at EPO levels that are undetectable by ELISA. For these reasons, efforts were undertaken to tighten regulation of transgene expression using erythropoietin as the model for the development of an improved tightly regulated system.

In one embodiment of the present invention, the tightness of regulated EPO expression was improved by modifying certain aspects of the GENESWITCH® and inducible EPO plasmids. The starting GENESWITCH® plasmid was either the pGS1158 or analogous plasmids that code for GENESWITCH® regulator protein v3.1, and contain a CMV promoter and has an SV40 intron located in the 3' untranslated region and has an SV40 poly(A) signal. Modifications, as will be discussed in succeeding examples included: (1) modifications to the transcribed but untranslated portions of the GENESWITCH® plasmid; (2) truncation of the GAL-4 DNA binding domain; (3) use of a muscle specific promoter in the GENESWITCH® plasmid; and (4) modification of the core promoter on the inducible therapeutic gene plasmid. It should be noted that these modifications may be applied independently or in combination with the GENESWITCH® system.

EXAMPLE 3

Modifications to the Transcribed but Untranslated Portions of the GENESWITCH® Plasmid The transcribed portions of the GENESWITCH® plasmid were modified to include post-transcriptional elements (5' UTR including a synthetic intron and poly (A) signal) that could be expected to improve the level and fidelity of transgene expression. In a preferred embodiment of the present invention, both the molecular switch expression cassette and the therapeutic gene expression cassette include a synthetic intron.

Cryptic splicing in transcripts from eukaryotic expression vectors is obviously undesirable. To obtain control over the splicing pattern and to maximize gene expression, suboptimal introns can be replaced by a strong intron. A synthetic intron with consensus splicing sequences should be optimal for this purpose. The synthetic intron of the present embodiment includes consensus sequences for the 5' splice site, 3' splice site and branch point. When incorporated into eukaryotic vectors designed to express therapeutic genes, the synthetic intron will direct the splicing of RNA transcripts in a highly efficient and accurate manner, thereby minimizing cryptic splicing and maximizing production of the desired gene product.

The first and sixth position of the 5' splice site consensus sequence are partially ambiguous. The 5' splice site pairs with U1 snRNA. The chosen sequence minimizes the free energy of helix formation between U1 RNA and the synthetic 5' splice site.

```
5' ss    5'  CAGGUAAGU  3'    SEQ.ID.NO: 1
             |||||||||
U1 RNA   3'  GUCCAUUCA  5'    SEQ.ID.NO: 2
```

In mammals, the branch point sequence is very ambiguous. The branch point sequence, except for a single bulged A residue, pairs with U2 snRNA. The chosen sequence minimizes the free energy of helix formation between U2 RNA and the synthetic branch point sequence. It also matches the branch point sequence that is obligatory for yeast pre-mRNA splicing. The branch point is typically located 18-38 nts upstream of the 3' splice site. The branch point of the synthetic intron is located 24 nts upstream from the 3' splice site.

```
BP       5'  UACUA^AC  3'    SEQ.ID.NO: 3
             ||||| |
U2 RNA   3'  AUGAU G   5'    SEQ.ID.NO: 4
```

The polypyrimidine tract of the consensus sequence for 3' splice sites is not exactly defined. At least 5 consecutive uracil residues are needed for optimal 3' splice site function. This concept is incorporated into the polypyrimidine tract of the synthetic intron, which has 7 consecutive uracil residues.

Splicing in vitro is optimal when introns are >80 nts in length. Although many introns may be thousands of bases in length, most naturally occurring introns are 90-200 nt in length. The elemental structure of a synthetic intron according to the present invention (SEQ.ID.NO: 5) is shown in FIG. 3 compared with italicized consensus sequences (SEQ.ID.NO: 6).

In one synthetic intron embodiment of the present invention, IVS8, the length of the synthetic intron is 118 nucleotides. The sequence of IVS8, (SEQ.ID.NO: 7), is shown in FIG. 4. Exonic sequences are in boldface. N=any base. Consensus splicing signals are double-underlined. Restriction enzyme recognition sites are over-lined. The restriction enzyme BbsI may be used to cleave the DNA precisely at the 5' splice site, and EarI may be used to cleave the DNA precisely at the 3' splice site. The two restriction sites, BbsI and EarI, located within the synthetic intron, permit the intron to be easily and precisely deleted. The PstI and NheI sites are included to facilitate the verification of cloning procedures. Double-stranded DNA with this sequence may be prepared using mutually priming long oligonucleotides.

To more closely match the structure of naturally occurring genes, which typically contain many introns, the synthetic intron may be inserted into the gene of interest at multiple locations. When multiple introns are inserted, however, care must be taken to ensure that the lengths of resultant internal exons are less than 300 nucleotides. If internal exons are greater than 300 nucleotides in length, exon skipping may occur.

In one embodiment, the expression cassette was further modified to introduce a CMV 5' UTR, termed UT12 (SEQ. ID. NO: 8) in addition to the synthetic intron, IVS8 (SEQ.ID.NO: 7), within the 5' UTR. The SV40 polyadenylation signal was replaced with a human growth hormone ("hGH") poly (A) signal.

These modifications, or other expression cassette modifications known to those of skill in the art, may be employed to generally increase the level and fidelity of transgene expression from plasmid and viral vectors.

EXAMPLE 4

Truncation of the GAL-4 DNA Binding Domain

The GAL-4 DNA binding domain binds as a dimer to the palindromic 17-mer GAL-4 DNA binding site (CGGAA-GACTCTCCTCCG). The Kd for binding of GAL-4, residues 1-100, is 3 nM (Reece and Ptashne (1993) Science 261: 909-911). Thus, in order to bind to the GAL-4 promoter and activate transcription of the inducible EPO plasmid, it is contemplated that a GENESWITCH® regulatory protein having a GAL-4 DNA binding domain is required to form a homodimer. In the presence of the inducer, MFP, binding of MFP to the mutated hPR LBD may trigger a conformational change in the protein so as to initiate dimerization.

As discussed in Example I, however, increases in hematocrit levels were observed in the presence of the GENESWITCH® v.3.1 protein even without the MFP ligand, indicating that the GENESWITCH® v3.1 protein may be able to dimerize and bind the GAL-4 binding site and induce transgene expression in the absence of MFP. Efforts were undertaken to reduce this drug-independent induction of expression by considering the tertiary structure of GAL-4 using molecular modeling and designing truncation mutant having lower dimerization potential but retaining sequence-specific DNA binding activity.

FIG. 5 depicts the structure of the GAL-4 protein DNA binding domain, residues 1-93 SEQ. ID. NO. 10; residues 2-93 of which has been incorporated into the GENESWITCH® version 3.1 plasmids (correlating to the underlined nucleic acid sequence in FIG. 7, SEQ. ID. NO. 12, and amino acid sequence in FIG. 8, SEQ. ID. NO. 14). The DNA recognition unit (residues 9-40) is boxed, with the cysteine (C) residues involved in chelating zinc shown in bold. The coiled-coil structures that form the dimerization elements (residues 54-74 and 86-93) are also boxed, with the generally hydrophobic first and fourth positions of each heptad repeat sequence shown in bold. Residue Ser 47 and Arg 51, which form an H-bond between chains, are marked by carats.

The first seven residues of the GAL-4 DNA binding domain are disordered and are not known to contribute any function, while residues 8-40 form the Zn binding domain or the DNA recognition unit. This unit has two alpha helical domains that form a compact globular structure and in the presence of Zn resulting in a structure that is a binuclear metal ion cluster rather than a zinc finger, i.e., the cysteine-rich amino-acid sequence ($Cys^{11}$-$Xaa_2$-$Cys^{14}$-$Xaa_6$-$Cys^{21}$-$Xaa_6$-$Cys^{28}$-$Xaa_2$-$Cys^{31}$-$Xaa_6$-$Cys^{38}$) binds two Zn(II) ions (Pan and Coleman (1990) PNAS 87: 2077-81). The Zn cluster is responsible for making contact with the major groove of the 3 bp at extreme ends of the 17-mer binding site. A proline at 26 (cis proline) forms the loop that joins the two alpha-helical domains of the zinc cluster domain and is also critical for this function.

Residues 41-49 exist as a disordered linker that joins the DNA recognition unit and the dimerization elements (54-74 and 86-93). Once dimerized, residues 47-51 of dimerized subunits also interact with phosphates of the DNA target. Residues 50-64 are contemplated to be involved in weak dimerization. They consist of a short coiled-coil that forms an amphipathic alpha-helix and wherein two alpha-helices are packed into a parallel coiled-coil similar to a leucine zipper. In addition to hydrophobic interactions of 3 pairs of leucines and a pair of valines found within residues 54-74, there are two pairs of arg-glu salt links, and H-bonds between Arg 51 of one monomer to Ser 47 of the other monomer. Residues 65-93 are contemplated to form a strong dimerization domain. The structure of residues 65-71 has not been fully determined, but it is most likely a continuation of the coiled-coil structure for one heptad repeat. Residues 72-78 contain a proline and therefore disrupt the amphipathic helix. Residues 79-99, however, contain three more potentially alpha-helical heptad sequences (Marmorstein et al (1992) Nature 356: 408-414).

There are a number of possible modifications that can be made to the regions of the GAL-4 domain as discussed above. Modifications in these regions may result in lower basal expression but still retain sequence-specific DNA binding. For example, the length of the region that contains the interacting coiled-coil sequences (residues 54-74 and residues 86-93) could be shortened by deletion such as deleting amino acid sequence 54-64, 65-74, 54-74, or 86-93. As such, GAL-4 mutants with only one coiled-coil region could be constructed by deleting one of the coiled-coil regions. In addition, mutant or artificial sequences may also be used to replace the fragment GAL-4 domain with unique restriction sites positioned at key spots, for example at the junctions of each of the alpha-helical heptad sequences. Thus, modified versions of the GAL-4 protein domain could be produced that have progressively reduced alpha-helical heptad sequences.

In one exemplary embodiment of the present invention, the GAL-4 domain was truncated by deletion of amino acids 75-93. This was achieved through the use of a convenient restriction endonuclease sites (Hinc II and Xho I) although other truncations may be produced according to molecular biology techniques known to those of skill in the art. By deleting the 72 bp XhoI-HincII fragment from pGS1210, pGS1539 (CMV-GENESWITCH® v.4.0) was generated, which has a 19 amino acid truncation at the C-terminal portion of the GAL-4 DNA-binding domain (the deletion corresponding to amino acid sequence 75-93 of SEQ. ID. NO. 10 in FIG. 5). FIG. 7 shows the nucleic acid sequences of the GENESWITCH® coding region of both GENESWITCH® v.3.1 and v.4.0, SEQ. ID. NOS. 12 & 13, while FIG. 8 shows the amino acid sequences of the same SEQ. ID. NOS. 14 & 15. Molecular modeling indicates that deletion of residues 75-93 removed the C-terminal helical portion without affecting the helical and coiled structure of the upstream amino acid sequences.

Figure 6:
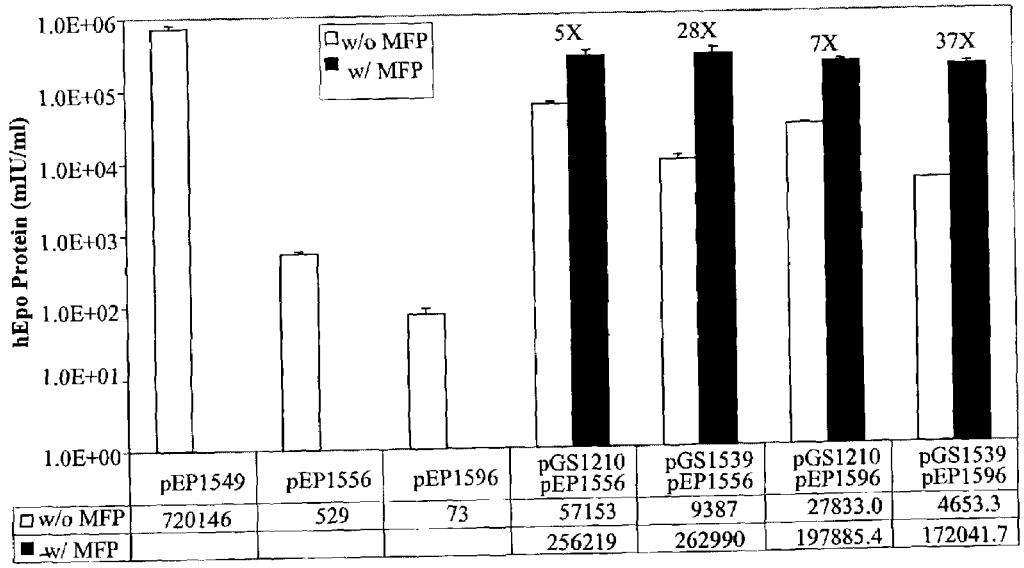
FIG. 6 depicts the comparison between the basal expression of human EPO in COS-1 cells using a CMV-controlled (constitutive) hEPO expression plasmid and various inducible EPO plasmids (pEP1556 (intact inducible promoter) and pEP1596 (initiator, "inr", deleted promoter).

FIG. 6 shows the effect of this C-terminal truncation of the GAL-4 DNA binding domain. COS-1 cells were transfected with pEP1556 (intact inducible promoter) and with either pGS1210 (CMV-GSv3.1) or pGS1539 (CMV-GSv4.0). When comparing the effect on EPO protein expression by GENESWITCH® v3.1 and v4.0 with the intact inducible promoter (pGS1210/pEP1556 vs pGS1539/pEP1556), a 5-fold increase (from 5× to 28×) in induction was observed mainly due to a decrease in basal EPO expression (57153 to 9387 mIU/ml), brought about by the truncation of the GAL-4 DNA binding domain.

It is notable that a 1-74 amino acid GAL-4 domain has been reported in a regulator protein chimera having a native estrogen-receptor ligand-binding domain and a VP-16 transactivation domain. Webster, J. et al., Cell 54:199 (1988). However, this construct was reported to have only 50% of the activity of a construct having amino acids 1-147 of the GAL-4 domain. In contrast, the present construct having GAL-4 (2-74) together with a mutated progesterone receptor ligand-binding domain was as active as a GAL-4 1-93 construct in the presence of ligand while having lower background in the absence of ligand.

FIG. 7 shows the nucleic acid sequences of the GENESWITCH® coding region of both GENESWITCH® plasmids v.3.1 (SEQ. ID. NO: 12) and v.4.0 (SEQ. ID. NO: 13), while FIG. 8 shows the amino acid sequences of the same, GENESWITCH® proteins v.3.1 (SEQ. ID. NO: 14) and v.4.0 (SEQ. ID. NO: 15). As is apparent in FIG. 8, the N-terminal methionine of the native GAL-4 sequence have been removed and a further eight amino acids have been added to the N-terminal end of the GENESWITCH® protein. Modifications to the N-terminal seven amino acids region are not of consequence as long as they do not affect the tertiary structure of residues 8-40 of the Zn binding domain.

EXAMPLE 5

Modification of the Transgene Core Promoter

The core region of the inducible promoter in the regulated EPO plasmid was also modified to reduce the basal expression of EPO without reducing the inducibility of EPO expression. This was desirable because increases in hematocrit level were observed when the original inducible mEPO plasmid was delivered by itself (in the absence of GENESWITCH® plasmid) to mice. This increase in hematocrit level was found to be dose dependent such that at higher plasmid doses, sufficient EPO was produced to result in an increase in hematocrit level from the EPO plasmid alone in the absence of the GENESWITCH® plasmid. It was, thus, desirable to develop a system in which the basal expression from the EPO plasmid was significantly reduced in order to increase reliance on administration of the inducer drug and provide an increased margin of safety by virtue of extrinsically controlled expression rather than through dependence on plasmid administration dose.

The promoter of an inducible EPO plasmid usually contains 6× GAL-4 sites linked to a TATA box. (FIGS. 9A and B) Different numbers of GAL-4 sites may be employed and the optimal number may be determined empirically. FIG. 9B depicts the nucleotide sequence of an inducible 6× GAL-4/TATA promoter (SEQ.ID.NO. 25). The six GAL-4 elements (17 bp in length) are boxed, the TATA box (−29 to −24) is double-underlined, and the predicted transcription initiation site (+1) is marked by the arrow. The sequence from −33 to −22, which contains the TATA box, is from the E1b region of Adenovirus type 2 (residues 1665-1677 of NCBI accession no. J01917).

For this experiment, human, mouse or rat EPO coding sequences, adjusted for codon usage and removal of cryptic splice sites, were synthesized by Operon Technologies, Inc. (Alameda, Calif.) and cloned into plasmids with the inducible 6× GAL-4/TATA box promoter. One inducible murine EPO plasmid is pEP1442 having a core promoter shown schematically in FIG. 9A wherein relevant regions of the inducible promoter with unique restriction sites are indicated. The core promoter also consists of 6× GAL-4 sites linked to an Ad E1b TATA box joined to a CMV sequence that contains the putative initiator (inr) region of the CMV promoter (Macias et al., Journ. of Virol. 70(6):3628 (1996)). Just downstream of this inr region is UT12 (5' untranslated region (UTR) of CMV, +1 to +112). The high activity of this core promoter has been observed to result in drug-independent increases in the hematocrit level of mice.

Utilizing unique restriction endonuclease sites engineered into the core promoter region, different regions of the promoter and 5' UTR were deleted to determine what effect, if any, this would have on overall expression of the transgene in the presence or absence of the GENESWITCH® protein. FIG. 9A indicates schematically the unique restriction endonuclease sites used to delete the TATA box (Sal I/EcoR V), inr (EcoR V/BsmB I) and part of the UT12 (Sac II/Pac I). FIG. 9C depicts the sequence of the inducible promoter, SEQ. ID. NO. 17, with relevant regions and unique restriction enzyme sites boxed. BsmBI enzyme cleavage sites are indicated with arrows. "TF" refers to transcription factor binding site, and "inr" refers to initiator.

To reduce the basal activity of the inducible promoter, a 30 bp BsmBI-EcoRV fragment (13-42 bp downstream from the TATATAAT box) was deleted. The resultant inducible mEPO, rEPO and hEPO plasmids were pEP 1705, pEP1642 and pEP1596, respectively. In the case of the human EPO plasmid (pEP1596) having a deletion in the inr region, FIG. 6 shows that the level of EPO expression from pEP1596 (73 mIU/ml) was 7-10× lower than with the level of EPO expression from pEP1556 (529 mIU/ml) (intact inducible promoter) in the absence of a GENESWITCH® plasmid.

On the other hand, when the plasmid pEP1596 was co-transfected with the pGS1210 plasmid (GENESWITCH® v. 3.1), the inducibility of the EPO expression was increased from 5× inducibility to 7× inducibility. Hence, a deletion in the transcription initiation region (inr) of the inducible EPO plasmid significantly reduced the intrinsic activity of the promoter without impairing, and may even enhance, its ability to be induced.

EXAMPLE 6

Combination of Modifications to the Truncated GAL-4 DNA-binding Domain and the Modified Transgene Core Promoter FIG. 6 also shows that when the modifications to the truncated GAL-4 DNA-binding domain and inr-deleted transgene core promoter were combined, there was an even higher level of expression inducibility (37× inducibility for pGS1539 and pEP1596) compared to the truncated GAL-4 DNA binding domain alone (28× inducibility for pGS1539 and pEP 1556) and the inr-deleted transgene core promoter alone (7× inducibility for pGS 1210 and pEP1596). Again, this was attributed to a further decrease in basal EPO expression (pGS1539/pEP1596 level of 4650 mIU/ml in the absence of MFP).

EXAMPLE 7

Muscle Specific Promoter in the GENESWITCH® Plasmid

Where expression in a particular tissue is desired, strong non-tissue specific promoters may be replaced with tissue specific promoters. For example, if the target tissue for gene expression is muscle, an actin promoter may be employed. Several advantages may be gained through the use of tissue-specific promoters. In a particular tissue, such as for example, muscle tissue, use of muscle-specific promoters may increase the fidelity of expression. Tissue-specific promoters may be expected to decrease the potential for unscheduled gene expression in non-target tissues. In particular, tissue-specific promoters may provide the advantage of reduced expression in dendritic and other antigen presenting cells, thus avoiding immune responses to the expressed proteins. In certain circumstances, a low level of regulator plasmid expression may also be desirable. In a combination plasmid system, it is also preferable to regulate the level of transgene expression by inherent properties of the plasmid delivered rather than by attempting to variably titrate the dose of plasmid delivered.

As the level of basal expression without MFP was found to increase with increasing plasmid dose, it was desirable to reduce the amount of GENESWITCH® protein made by utilizing a weaker promoter. In muscle tissue for example, the avian skeletal alpha-actin promoter results in less gene expression that the CMV promoter. In one embodiment, the CMV promoter of the GENESWITCH® plasmid was replaced with a muscle-specific promoter, avian skeletal alpha-actin promoter (SK promoter) (SEQ. ID. NO. 16) to reduce the level of regulator protein produced. The avian skeletal alpha-actin promoter is described in U.S. Pat. No. 5,298,422, incorporated herein by reference in its entirety.

In another embodiment, the muscle-specific avian skeletal alpha-actin promoter was combined with an optimized arrangement of post-transcriptional elements (5' untranslated region (UT12), synthetic intron (IVS 8) and poly(A) signal (hGH pA)).

As depicted in FIG. 2, the improved plasmids (pGS1633, pGS1694) code for GENESWITCH® regulator protein v.4.0 constructed by deleting about 20 C-terminal residues of the GAL-4 region (indicated by the inverted triangle in FIG. 2) together with. replacement of the CMV promoter with a muscle-specific promoter. Muscle-specific GENESWITCH® v.4.0 constructs (pGS1633 and pGS1694, identical except for minor variations in plasmid backbone) were generated by replacing the CMV promoter with the chicken skeletal alpha-actin promoter (base pairs –420 to –1).

Use of the muscle specific promoter for the molecular switch expression cassette resulted in lower basal expression in the absence of inducer and higher level with induction. With the muscle-specific system (pEP1596/pGS1633), hEPO expression was regulated in a manner that was strictly dependent on the inducing drug, MFP. No hEPO expression or increase in hematocrit level was detected in the absence of MFP treatment, and when MFP was administered, hEPO was induced to high levels (>300 mU/mL), which caused hematocrit to increase from 45% to 60%. In contrast, with the CMV-GENESWITCH® system (pEP1596/pGS1539), hEPO expression was regulated in a manner that was significantly less robust. Low levels of hEPO expression and increases in hematocrit level occurred in the absence of MFP treatment, and when MFP was administered, the level of induced hEPO expression was modest (~50 mU/mL).

EXAMPLE 8

Figure 11:
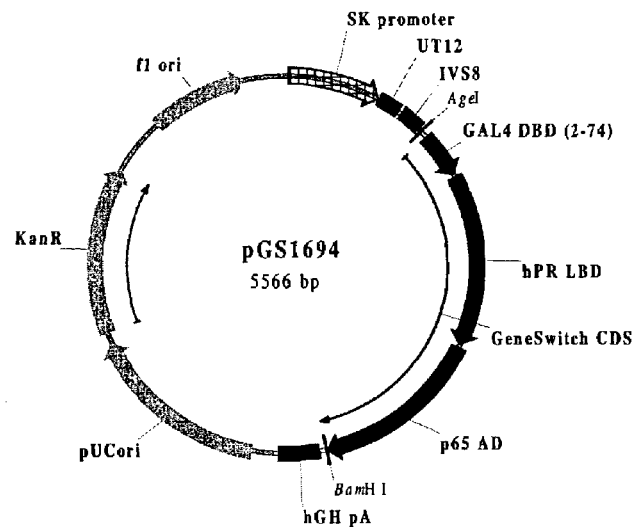
FIG. 11 depicts the plasmid map of pGS1694, GENESWITCH® Plasmid Version 4.0 having a chicken skeletal α-actin ("SK") promoter according to one embodiment of the present invention.
Figure 12:
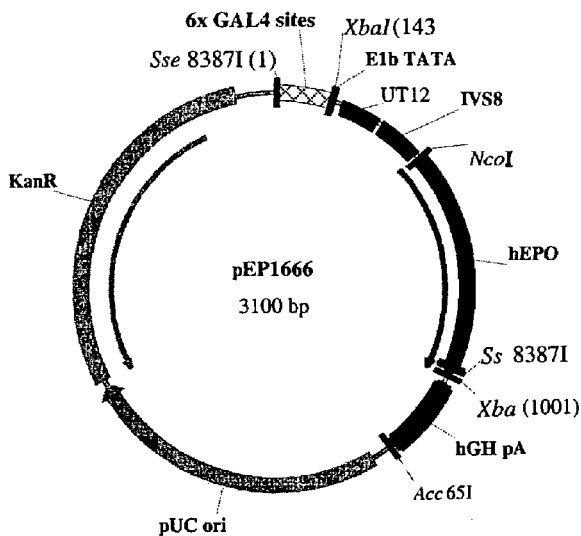
FIG. 12 depicts the plasmid map of pEP1666, a expression-regulated hEPO expression plasmid, according to one embodiment of the present invention.

In a preferred embodiment that combines the various improvements discussed above, a muscle-specific GENESWITCH® plasmid having a truncation of GAL-4 DNA binding domain ($DBD_{2-74}$) (pGS1694) may be used together with a regulated human EPO expression plasmid having the inr deletion (pEP1666). The GENESWITCH® regulator protein plasmid may utilize an α-actin muscle specific promoter upstream of the regulator protein coding sequences that include a truncated GAL-4 domain, a mutated progesterone receptor having a C-terminal deletion of 19 amino acids and a p65 transactivation domain. A map of an exemplary plasmid having this construction, SK GENESWITCH® plasmid version 4.0 (pGS1694) is shown in FIG. 11 with the corresponding sequence on FIG. 13 SEQ. ID. NO. 22 (the GAL-4 sequence is bold in italics, the mutated steroid binding domain is underlined, and the p65 transactivation domain is in bold). A map of an exemplary regulated human-EPO plasmid, pEP1666 is shown in FIG. 12 SEQ. ID. NO. 23 with the corresponding sequence on FIG. 14 (EPO sequence in italics).

Figure 15:
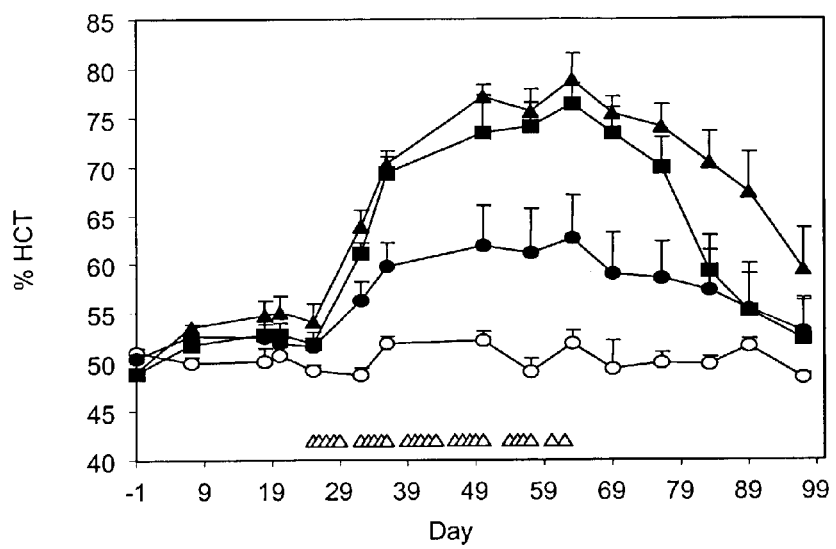
FIG. 15 depicts hematocrit regulation in mice by low oral doses of mifepristone (MFP) using an improved expression-regulated system according to one embodiment of the present invention. A 1:1 mixture of the improved plasmids, pEP 1705 (inducible mEPO) and pGS1694 (muscle-specific GENESWITCH® v.4.0) in a total dose of 150 micrograms, was formulated with sodium poly-L-glutamate and delivered with electroporation to both tibialis and gastrocnemius muscles of mice on day 0. Beginning on day 25, oral MFP (Δ) was administered chronically (daily on weekdays) at doses of 0.0 (○), 0.01 mg/kg (●), 0.03 mg/kg (▲) or 0.10 mg/Kg (■).

FIG. 15 depicts the results of administering a 1:1 mixture of the improved plasmids, pEP1705 (inducible mEPO with inr deletion) and pGS1694 (muscle-specific GENESWITCH® v.4.0) at a total dose of 150 micrograms, which was formulated with sodium poly-L-glutamate and delivered with electroporation to both tibialis and gastrocnemius muscles of mice on day 0. Beginning on day 25, oral MFP (Δ) was administered chronically (daily on weekdays) at doses of 0.0 (○), 0.01 mg/kg (●), 0.03 mg/kg (▲) or 0.10 mg/Kg (■). Blood samples were analyzed for hematocrit level. Each group contained five animals and data are expressed as mean±SEM.

In the absence of MFP treatment, serum levels of mEPO were undetectable and no significant increases in hematocrit level occurred in the animals from day 0 to day 25 (FIG. 15). Thus, the improvements to the mEPO/GENESWITCH® system sufficiently reduced the level of basal expression, in the absence of an inducer, even when the plasmids were delivered to mice at a high dose (7.5 mg/Kg body weight). Starting at day 25, when oral doses of MFP were administered for 6 weeks, induction of stable, statistically significant increases in mEPO expression and hematocrit levels were observed. Induced levels of mEPO were barely detectable at the lowest MFP dose (0.01 mg/Kg), but hematocrit levels gradually increased from 50 to 61% (FIG. 15, (●) from day 25 to about day 37). This 11-point increase, which was significant compared to the control group, was also maintained during the course of MFP treatment.

At MFP doses of 0.03 or 1.0 mg/Kg, induced levels of mEPO exceeded 20 mU/mL and hematocrit levels increased to 73-78%. (FIG. 15, (▲) and (■) about day 37 and day 49) These hematocrit levels were significantly higher than those of animals treated with 0.01 mg/Kg (●). When MFP dosing was ceased, mEPO expression immediately returned to undetectable levels and hematocrit levels began to decline. A complete return to baseline levels was observed to require at least 30 days. To summarize, strict, ligand-dependent regulation of hematocrit levels in mice following delivery of the improved mEPO/GENESWITCH® plasmids was obtained in contrast to the unregulated hematocrit levels as discussed in Example I in conjunction with FIG. 1. Furthermore, increases in hematocrit levels have been shown to be controlled by adjusting the dose of the orally administered ligand.

EXAMPLE 9

Figure 17A:
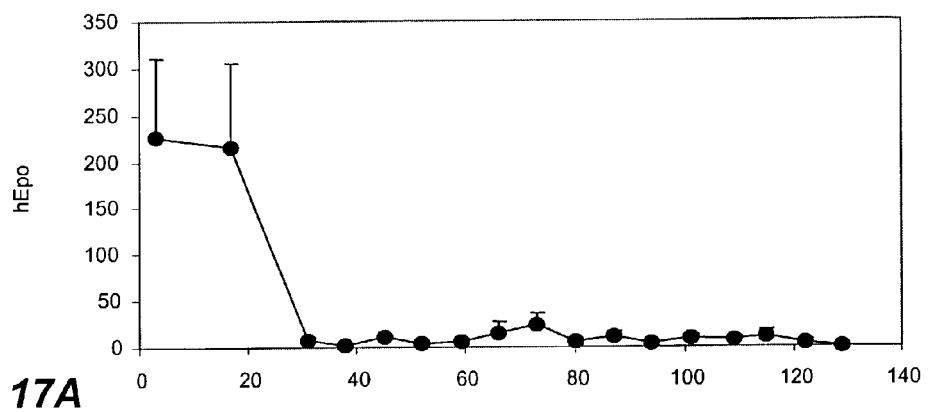
FIG. 17A demonstrates levels of hEPO expression exhibited by 5/5 mice (mean±SEM).
Figure 17B:
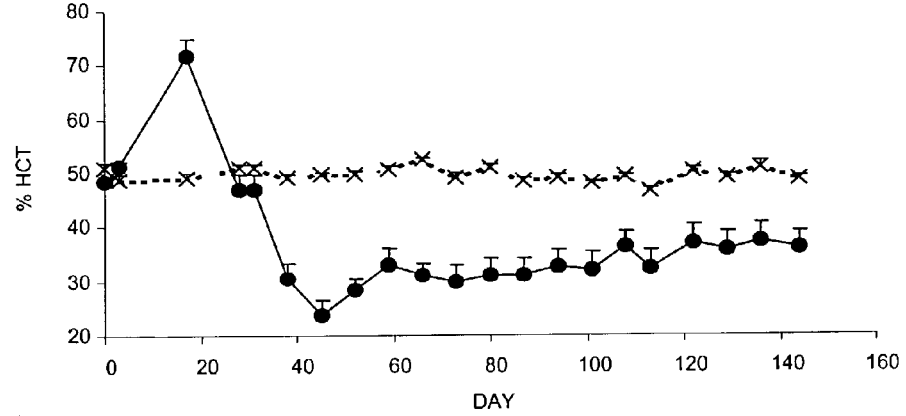
FIG. 17B demonstrates hematocrit levels exhibited by 5/5 mice (mean±SEM).

Immune responses resulting from administration of a gene encoding a foreign species protein can be analogized to immune responses occurring in humans receiving replacement therapy for a genetic defect characterized by absence of a normal functional protein such as the hemophilias. This scenario was modeled by administration of 75 mg of pEP 1549 (CMV-human EPO) formulated with sodium poly-L-glutamate and delivered with electroporation to both tibialis and gastrocnemius muscles of five mice. FIG. 17A demonstrates levels of hEPO expression exhibited by 5/5 mice (mean±SEM). FIG. 17B demonstrates hematocrit levels exhibited by 5/5 mice (mean±SEM). As shown in FIG. 17, when a human protein such as human EPO was produced in mice constitutively using a CMV-hEPO plasmid administered to muscle with electroporation, all animals developed erythroid hypoplasia, characterized by subnormal hematocrit, loss of hEPO expression and the appearance of anti-hEPO antibodies.

The ability of a regulated system to control immune responses to a foreign transgene was explored. Induction of gene expression was delayed for various periods following gene administration. The results of long-term regulation of a foreign transgene (human EPO) in mice are shown in FIG. 18. A 1:1 mixture of pEP1596 (inducible hEPO having deletion of the inr region) and pGS1633 (muscle-specific GENESWITCH® v.4.0 having a truncation in the GAL-4 domain), total dose of 150 micrograms, was formulated with sodium poly-L-glutamate or saline and delivered with electroporation to both tibialis and gastrocnemius muscles of five mice. Each formulation group (saline or poly-L-glutamate) was then subdivided into two groups, where one group received its first mifepristone (MFP) dosing on day 13, and the other group received it on day 55. All MFP dosing regimens consisted of five consecutive days of oral administration of a 0.33 mg/Kg dose in sesame seed oil. After the initial MFP dosing, all animals were given MFP on the following days: 105-109, 154-158, 210-214. Finally, on day 268 a slow release. MFP pellet was implanted subcutaneously into all remaining animals. hEPO protein levels were measured four days after the first MFP dose and hematocrit levels were measured weekly.

The saline formulated hEPO/SK-GS system was induced four times over a 270-day period by MFP. The hEPO protein level, in the 12-day lag group, was induced to ~300 mU/mi after each induction. Three of the five animals showed elevated hematocrit levels (increased from 45 to ~55%) after all four inductions, while the remaining two animals in this group had elevated hematocrit levels after just the first and second inductions. The hEPO protein levels in the 54-day lag group were also induced to ~300 mU/ml after each induction. However, four out of five animals had elevated hematocrit levels (~55%) after all four inductions. The remaining animal in this group responded to just the first two inductions. All three of the non-responder animals in these two groups went anemic (hematocrit level 5% below normal) sometime after the second induction. Very low levels of antibodies to hEPO (OD450 values <0.25) were detected in all ten animals in these groups on days 109 and 113.

Figure 18A:
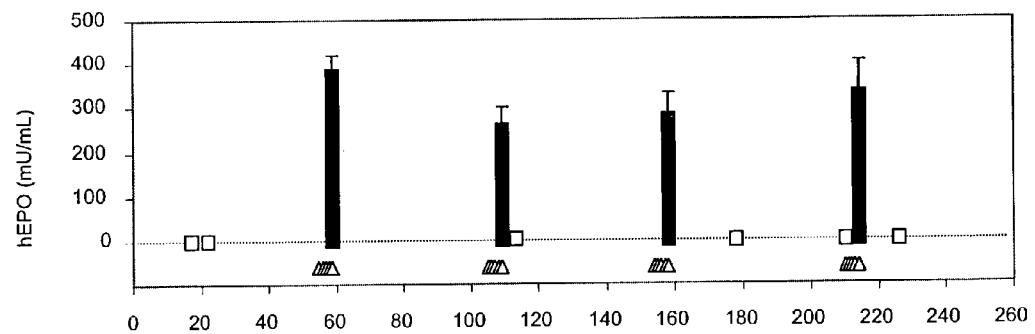
FIG. 18A depicts the level of hEPO in the serum of mice and FIG. 18B depicts the % hematocrit level.
Figure 18B:
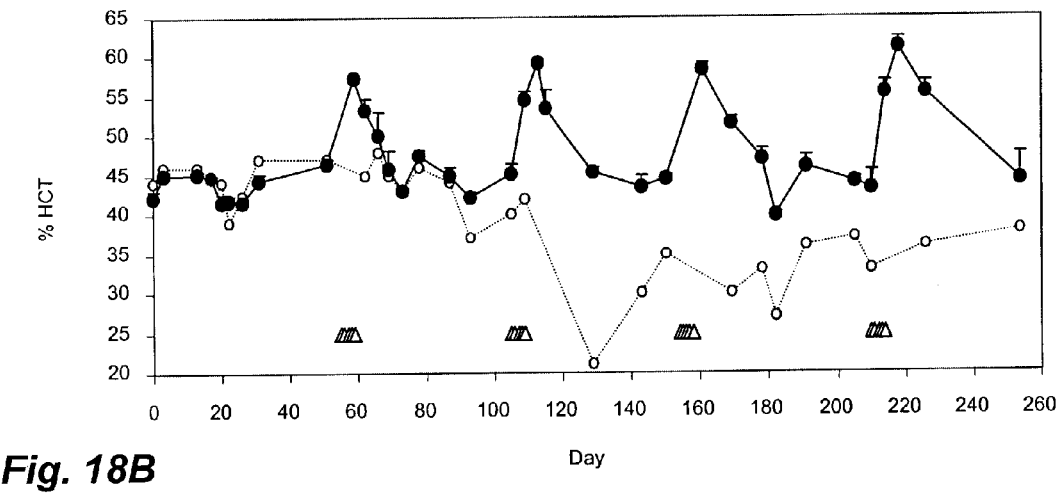

The poly-L-glutamate formulated hEPO/SK-GS system was induced four times over a 270-day period by MFP. The hEPO protein level, in the 12-day lag group, was induced to ~400 mU/ml after each dosing. Two of five animals showed elevated hematocrit levels (~60%) after all four inductions. Two of the remaining animals responded to just the first induction, while the final animal in the group responded to the first two inductions. The hEPO protein levels in the 54-day lag group were induced to ~250 mU/ml after each dosing. Following rounds of MFP dosing initiated on days 104, 154 and 210, hEPO levels increased to 249±51, 272±59 and 322±81 mU/mL, respectively, and hematocrits increased to 59±0.5%, 58±0.9 and 61±1.3%, respectively (FIG. 18). Each data point shown is the mean± SEM of 4/5 animals. FIG. 18A depicts levels of hEPO expression exhibited by 4/5 mice (mean±SEM). FIG. 18B depicts hematocrit levels exhibited by 4/5 mice (●, mean±SEM) and one individual animal, (○), in which antibodies to the foreign EPO developed.

Anemia was observed after the second round of inductions in all the non-responders in the two groups. A significant antibody response to hEPO was detected in only one animal from each group on day 113, and both animals went anemic after the second induction.

On day 268, all of the animals that received the poly-L-glutamate formulated hEPO/SK-GS system, were administered a MFP pellet by subcutaneous implantation. Two of the 12-day lag animals responded to the pellet and achieved hematocrit levels of ~75%. One animal had no change in hematocrit level, and the final two animals were hypocythemic. Three of the 54-day lag animals responded to the pellet and achieved hematocrit levels of ~75%. The hematocrit of one animal appeared to be declining towards anemia (after an initial increase in hematocrit to ~65%) when the experiment ended, and there was no effect on the remaining animal that was already hypocythemic.

These studies showed that when 1:1 (w/w) mixtures of inducible human EPO and muscle-specific GENESWITCH® plasmids (pEP1596/pGS1633 or pEP1666/pGS1694) were delivered to the tibialis and gastrocnemius muscles of C57BL/6 mice at doses as high as 150 □g (~7.5 mg/kg body weight), no hEPO expression was detected and no increases in hematocrit occurred in the absence of MFP dosing. In one study, the lack of basal expression in the period between plasmid delivery and induction of hEPO expression was confirmed for 55 days. The lack of "leaky" expression in mice at plasmid doses of ~7.5 mg/kg body weight predicts that a similar lack of "leaky" expression will occur when plasmids are delivered to humans at doses of 0.5 mg/kg body weight (the highest proposed human dose) or less.

In summary, although immune responses to the hEPO protein occasionally occurred when hEPO/GENESWITCH® plasmids were delivered to mice, neutralizing responses were more moderate and less frequent. In one study, neutralizing immune responses, characterized by the loss of inducible hEPO expression, a decline in hematocrit to subnormal levels, and the appearance of elevated levels of anti-hEPO antibodies, occurred in only 45% of the animals, and 65% retained the ability to induce hEPO expression and hematocrit for more than 8 months. In contrast, expression of CMV-hEPO leads to neutralizing immune responses in 100% of the animals. The tightly regulated gene switch system disclosed herein permits is the imposition of a lag time between plasmid delivery and induction of hEPO expression.

Delivery of plasmids with electroporation is associated with transient damage to muscle fibers and inflammatory cell infiltrates. Thus, plasmids with constitutive promoters will express foreign transgene products in an inflammatory environment that is highly immunostimulatory. On the other hand, if transgene expression is delayed to a time when inflammatory responses have subsided, as is done with the hEPO/GENESWITCH® system, immune responses appear to be lessened considerably.

Thus, by increasing the length of the lag period (time before inducing the foreign transgene) from 12 to 54 days, the incidence of erythroid hypocythemia and anti-hEPO antibody production can be decreased.

EXAMPLE 10

Hematocrit Regulation in Rats in the Improved System Following Delivery of Low Plasmid Doses The next set of experiments was performed to determine the reproducibility of the mice results in larger animals such as a rodent. Hence, plasmids were formulated with sodium poly-L-glutamate and delivered to the gastrocnemius muscles of rats with electroporation. Fischer female rats (250 g) were obtained from Harlan Sprague Dawley (Raleigh, N.C.). Mifepristone (Sigma, St. Louis, Mo.) in sesame oil was administered to the rats (150-400 microliters, intraperitoneal).

Figure 16A:
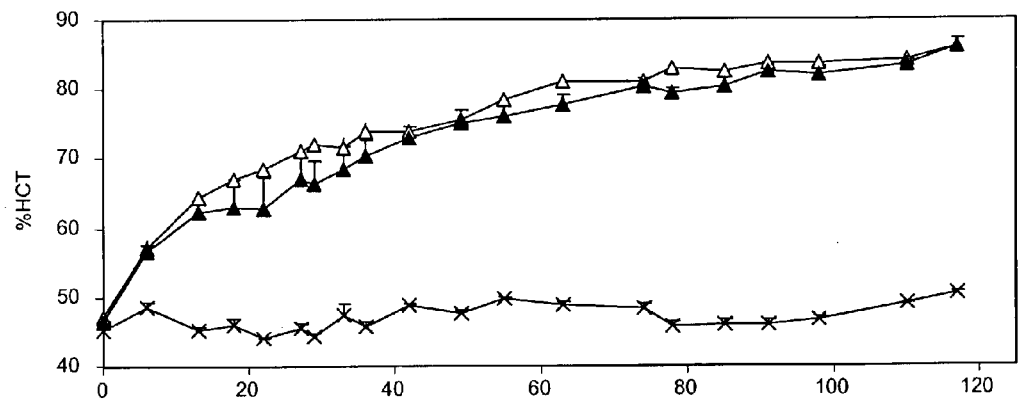
FIG. 16A depicts the hematocrit regulation in rats following delivery of low plasmid doses of CMV-controlled EPO expression plasmid.

FIG. 16A shows the results of an experiment using a constitutively expressing rat EPO (rEPO) expression plasmid. At day 0, 1:1 mixtures of pEP1641 (CMV-rEPO) and pEP1642 (inducible rEPO, added as filler) were formulated with sodium poly-L-glutamate and were administered at doses of 7.5 (Δ) or 25 micrograms (▲) per animal and the hematocrit levels of the rats were monitored. As a control, naïve animals (X) received no plasmid treatment. Following delivery of CMV-rEPO plasmid at doses of 7.5 or 25 micrograms, hematocrit levels increased within 7 days and rapidly reached levels that exceeded 80%. rEPO expression was maintained for at least 91 days at 9±3 and 28±16 mU/mL at the lower and higher plasmid doses, respectively. Hence, uncontrolled polycythemia resulted from the delivery of a constitutively expressed EPO plasmid even at a dose as low as 0.025 mg/Kg. This data emphasize the need for a tightly regulated EPO transgene expression system.

Figure 16B:
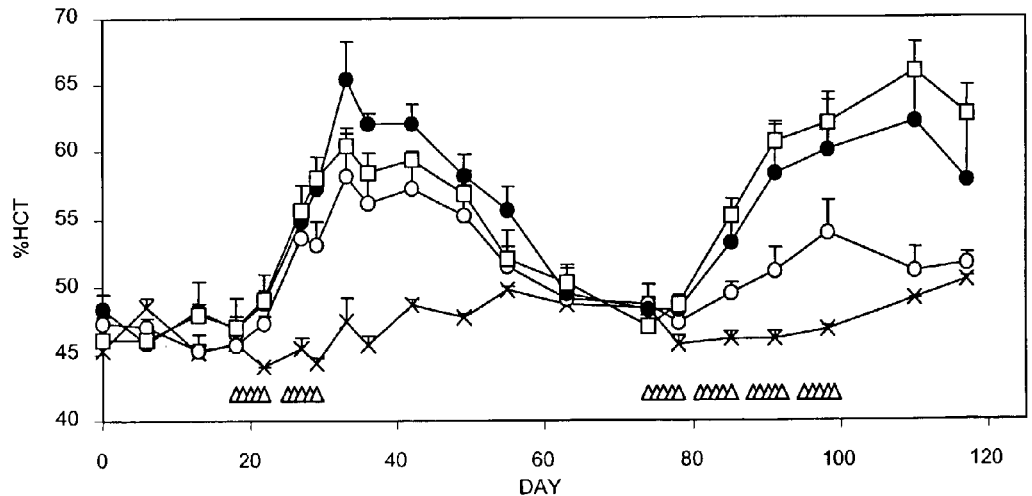
FIG. 16B depicts the hematocrit regulation in rats following the delivery of pEP1642 (inducible rat EPO) and pGS1694 (muscle-specific GENESWITCH® v.4.0) and induction by MFP.

FIG. 16B depicts an improved regulated EPO expression system in rats according to one embodiment of the present invention. Using electroporation, 1:1 mixtures of pEP1642 (inducible rat EPO) and pGS1694 (muscle-specific GENESWITCH® v.4.0) were administered at doses of 7.5 (○), 25 (●), or 75 (□) micrograms per animal to rat gastrocnemius muscle at day 0. The days when MFP were administered to the animals are indicated as open triangles (Δ) at the X-axis of FIG. 16B. For the first induction cycle, MFP was administered on days 18-22 at 1 mg/Kg, and on days 25-29 at 5 mg/Kg. For the second induction cycle, MFP was administered at 1 mg/Kg on each weekday, for 6 weeks, beginning on day 73. Blood samples were assayed for hematocrit levels. Each group contained five animals and data are expressed as mean±SEM. To induce rEPO expression, we administered MFP at a relatively high dose (1-5 mg/Kg), since it is cleared rapidly in rats (half-life of 1 hr, Deraedt, R. et al. in The Antiprogestin Steroid RU486 and Human Fertility Control, E. E. Balieu, S. Segal, Eds. 103-122, Plenum Press, New York, 1985).

During the 17 days immediately after plasmid delivery, no significant change in hematocrit level occurred in contrast to the first 25 days shown in FIG. 16A. When MFP was orally administered for two weeks starting on day 18, hematocrit levels increased following administration and peak hematocrit levels were observed to have occurred on day 33, four days after the final MFP dose in the first induction cycle. Unexpectedly, the lowest plasmid dose (0.025 mg/Kg (○))

yielded a hematocrit response that was indistinguishable from that achieved by the highest plasmid dose (0.8 mg/Kg (□)). Hematocrit values of all treated groups were significantly different than naïve groups (X) and remained elevated for approximately 1 month before returning to baseline levels.

When MFP was re-administered at a lower dose (1 mg/Kg for 4 weeks, beginning on day 73), re-induction of hematocrit levels was observed. Peak hematocrit levels occurred two weeks after the completion of MFP dosing, and then began to decline. At the higher plasmid doses, the increases in hematocrit level were significant compared to näive animals. However, at the lowest plasmid dose, where a more modest response was observed, the increases in hematocrit level did not achieve statistical significance. This data demonstrate that durable, ligand-dependant regulation of hematocrit levels can be achieved in rats by low plasmid doses of the improved regulated EPO expression system.

EXAMPLE 11

Regulation of Human EPO Expression in Larger Animals

To further assess the applicability of the improved EPO/GENESWITCH® system in larger animals, the plasmid-based hEPO/GENESWITCH® v.4.0 system was tested in dogs. On day 0, 1:1 mixtures of pEP1596 (inducible hEPO with an inr-deleted region) and pGS1633 (muscle-specific GENESWITCH® v.4.0) were formulated with sodium poly-L-glutamate, injected into 2 or 6 skeletal muscle sites of dogs, and then subjected to electroporation with a 6-needle electrode array. The use of the needle electrode device facilitates electroporation of muscles in larger animals. In one case, 6 mg of formulated plasmid mixture was delivered to two sites (semimembranosus muscles) per dog (n=3). In another case, 18 mg of formulated plasmid mixture was delivered to six sites (triceps, semimembranosus, semitendanosus muscles) per dog (n=4). Six days following plasmid delivery, MFP (1 mg/kg) was administered orally and serum hEPO levels were measured.

During the 6 days following delivery of the 6 mg plasmid dose but before the administration of MFP, hEPO expression was undetectable. Following two days of oral MFP dosing, however, an induction of serum hEPO was observed. Four days after cessation of the 3-day MFP treatment, hEPO levels dropped to near baseline levels. When MFP was re-administered on days 12-17, hEPO levels were again induced to similar levels as before. A similar pattern of expression was also observed using an 18 mg plasmid dose except that the induced levels of hEPO were 4 to 6-fold higher. Thus, the hEPO/GENESWITCH® system functions effectively in a larger animal.

However, no increase in hematocrit level was observed in any of the dogs. Instead, anti-hEPO antibodies appeared in all dogs by 3-4 weeks, which apparently neutralized the biological response. The appearance of antibodies may also account for the decline in hEPO levels that occurred in the midst of the second period of MFP dosing. This data showing the presence of neutralizing immune responses in all of the dogs are in contrasts with the lack of neutralizing immune responses in most of the mice treated with the hEPO/GENESWITCH® system (FIG. 18).

In addition to the difference in species, one other factor may contribute to the difference in the results in dogs and mice. In dogs, the MFP treatment was initiated after only six days from the day the plasmids were introduced into the animal. In contrast, MFP treatment was initiated in mice 55 days after the plasmids were introduced. As discussed in the experiments with mice, increasing the lag time between the time the plasmids are introduced and the start of MFP dosing significantly decrease the occurrence of erythroid hypoplasia. Thus, the length of time between plasmid delivery and induction of transgene expression may be a critical factor in preventing immune response to the foreign transgene. It is desirable then to lengthen the delay between the introduction of the plasmids and the start of the MFP to at least 12 days. More preferably, the lag period should be about 20 days (as shown in rats with FIG. 17B), and even more preferably to about 55 days as shown in mice (FIG. 18B).

EXAMPLE 12

Table 1 below describes the fundamental characteristics of the various test plasmids used in the development of a tightly regulated expression system while the nucleic acid sequences of the inducible promoter regions of the plasmids are set out in FIG. 10 (pEP1556— intact inducible promoter region: TATA box/initiator region (inr)/UT12 transcription factor binding site (UT12-TFBS)(SEQ. ID. NO. 18); pEP1595-SalI/EcoRV deletion of the TATA box promoter region:inr/UT12-TFBS (SEQ. ID. NO. 19); pEP1596— EcoRV/BsmBI deletion of the inr region: TATA box/UT12-TFBS (SEQ. ID. NO. 20); pPE1597— SacII/PacI deletion of the UT12 region: TATA box/inr (SEQ. ID. NO. 21).

TABLE 1

Plasmids used in testing the expression plasmid modifications

| Name | Promoter | GAL-4 domain | Promoter modification | Transgene |
|---|---|---|---|---|
| pEP1556 | 6xGAL-4/TATA | — | none | hEpo |
| pEP1595 | 6xGAL-4 | — | deleted TATA box | hEpo |
| pEP1596 | 6xGAL-4/TATA | — | deleted inr region | hEpo |
| pEP1597 | 6xGAL-4/TATA | — | deleted UT12 region | hEpo |
| pEP1549 | CMV enh/pro | — | none | hEpo |
| pGS1210 | CMV enh/pro | 2-93 | none | GENESWITCH ® v3.1 |
| pGS1539 | CMV enh/pro | 2-74 | none | GENESWITCH ® v4.0 |
| pGS1382 | 4xGAL-4/tk | 2-93 | none | GENESWITCH ® v3.1 |
| pGS1598 | 4xGAL-4/tk | 2-74 | none | GENESWITCH ® v4.0 |

The resultant inducible mEPO, rEPO and hEPO plasmids are pEP1705, pEP 1642 and pEP 1596, respectively.

EXAMPLE 13

In another embodiment of the present invention, the improved molecular switch protein may have the amino acid sequence: $MX_n/[yGAL-4_{2-74}]/X_n/[hPR_{640-914}]/X_n/[hP65_{285-551}]$ as exemplified by SEQ.ID.NO: 24 wherein $X_n$ represents a series of amino acid sequence. X can be any amino acid and n can be any number but preferably between 1-10. In another embodiment of the present invention, the improved molecular switch protein, encoded for example in GS v4.0 has the amino acid sequence $MDSQQPDL/[yGAL-4_{2-74}]/DQ/[hPR_{640-914}]/GST/[hP65_{285-551}]$ as exemplified by (SEQ.ID.NO: 15). Amino acids for the N-terminus and linker regions are indicated by single letter abbreviations. Individual protein components are bracketed and the amino acid residues are specified in subscript. yGAL-4 is the N-terminal DNA binding domain of the yeast GAL-4 protein (GenBank accession no. AAA34626). hPR is a C-terminal truncated portion of the ligand binding domain of the human progesterone receptor (GenBank accession no. AAA60081), where $hPR_{640-933}$ is the full-length version of the hPR-LBD. hP65 is the activation domain of the p65 subunit of human NFkappaB (GenBank accession no. AAA46408). The human components of the GENESWITCH® regulator protein comprise 86% of its sequence.

EXAMPLE 14

Expression of EPO Using Polymer Formulations and Electroporation

Plasmid DNA/anionic polymer formulations were preferably prepared by aliquoting appropriate volumes of sterile stock solutions of plasmid, anionic polymer and 5M NaCl to obtain selected final plasmid and anionic polymer concentrations. The anionic polymer was added to the DNA solution prior to adding salt for tonicity adjustment. Thus, poly-L-glutamate formulations are preferably prepared by combining an aqueous stock solution of sodium poly-L-glutamate (sodium salt of poly-L-glutamic acid) with a stock solution of purified plasmid DNA in saline or up to 10 mM Tris, pH 7.5. After the poly-L-glutamic acid and DNA are combined, the solution is adjusted to a final concentration of 150 mM NaCl by addition of a stock solution of 5M NaCl.

The ability of poly-L-glutamate to increase the expression of a non-viral erythropoietin ("EPO") gene delivery was undertaken. Using quantitative polymerase chain reaction (qPCR) analysis, plasmid formulated in poly-L-glutamate resulted in at least a log increase in levels of mEPO DNA compared with animals receiving a saline/DNA formulation.

Animals received CMV-mEPO formulated either in 15-50 kDa poly-L-glutamate or in saline. Plasmid formulations were injected intramuscularly in each leg, 25 microliters in each tibialis, 50 microliters in each gastrocnemius followed by electroporation 2 min after injection (375 V/cm (113 V/0.3 cm), 2 pulses, 25 msec pulse length. At defined time intervals, blood was collected by retro-orbital methods and hematocrit levels determined or the serum assayed for EPO levels.

Figure 19:
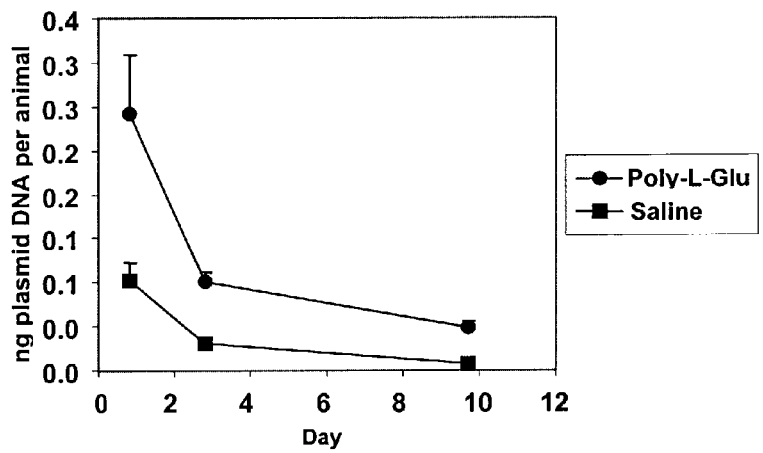
FIG. 19 depicts the quantitative PCR results showing the duration of retention of the mouse EPO plasmid DNA following delivery by electroporation using saline and poly-L-glutamic acid formulations.

At indicated times, total muscle DNA was extracted and levels of were quantified by qPCR as follows: Plasmid DNA quantities in mouse muscles were determined by conducting TaqMan® real time quantitative PCR (Applied Biosystems, Foster City, Calif.) on isolated DNA samples as previously described (Mahato, R. I. et al. Hum. Gene Ther. 9:2083 (1998)). The primers used in the PCR were a forward primer, which primes in the 5' untranslated region, and a reverse primer, which primes in the mouse EPO coding region. The probe sequence was located within the EPO gene. Purified CMV-mEPO plasmid DNA was used to generate a standard curve for the PCR assay. As shown in FIG. 19, formulation in poly-L-glutamate results in a several fold increase in the amount of plasmid DNA that can be detected in tissues after electroporation.

Figure 20:
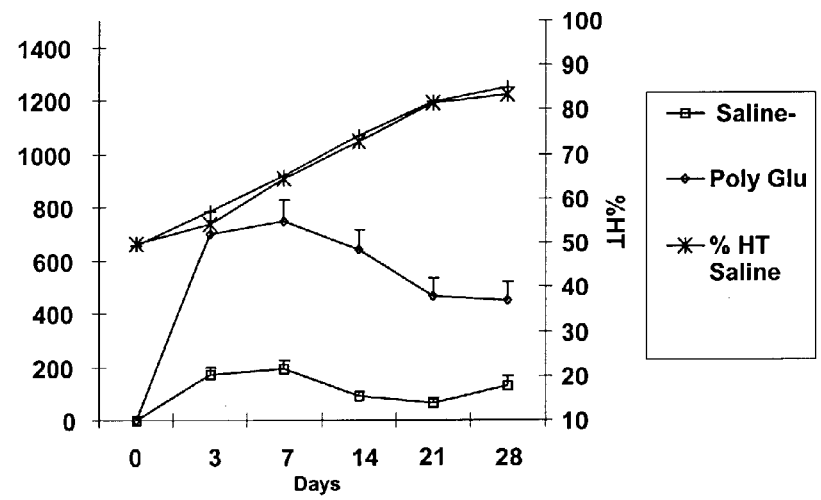
FIG. 20 depicts EPO expression and hematocrit levels in mice following delivery of the mouse EPO gene by electroporation using saline and poly-L-glutamate formulations.
Figure 21:
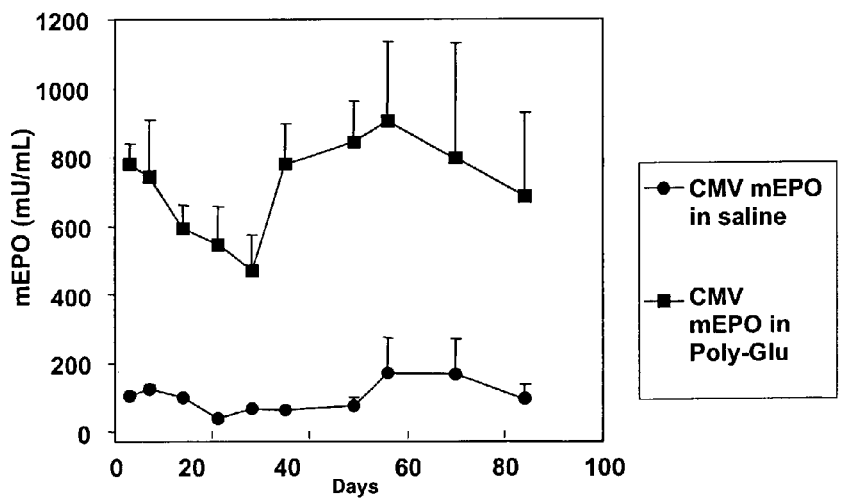
FIG. 21 depicts EPO expression in mice following delivery of the mouse EPO gene by electroporation using saline and poly-L-glutamate formulations over a three-month time frame.

For mEPO expression determination, 75 mg CMV-mEPO plasmid DNA in 150 ml was delivered to C57BL/6 mice, 25 microliters per tibialis, 50 microliters per gastrocnemius. Plasmid was formulated in saline or 6 mg/mL poly-L-glutamate. FIGS. 20 and 21 depict mEPO expression and FIG. 20 also depicts the hematocrit level in mice following delivery of the mouse EPO gene by electroporation using saline and sodium poly-L-glutamate formulations.

As shown in FIGS. 20 and 21, delivery in a poly-glutamate formulation results in considerably higher levels of expressed protein than when the plasmid DNA is delivered in saline. Because a very small amount of erythropoietin is required to give a maximal increase in hematocrit, the induced hematocrit levels shown on FIG. 20 do not differ between saline and polyglutamate formulations. However, because polyglutamate results in more efficient transfection, lower amounts of DNA can be administered using polyglutamate formulations.

EXAMPLE 15

Increased Duration of Human Factor IX Protein Expression Following Pulsatile Expression Using the GENESWITCH® System Experiments were also performed to extend the improved tightly regulated transgene expression system to other therapeutic gene aside from EPO. Plasmids encoding human factor IX (hF.IX) and an improved muscle-specific GENESWITCH® plasmid, according to the present invention were mixed together in a 1:1 ratio and formulated with a polymer formulation (poly-L-glutamate, 6 mg/ml). The plasmids at a concentration of 1 mg/ml were injected into the tibialis of the hind legs of female CD-1 mice (25 microliters each muscle for a total of 50 microliters per animal). Following the injection the muscles were electroporated using caliper electrodes and applying 2×375 V/cm square pulses for 25 msec each.

Figure 22:
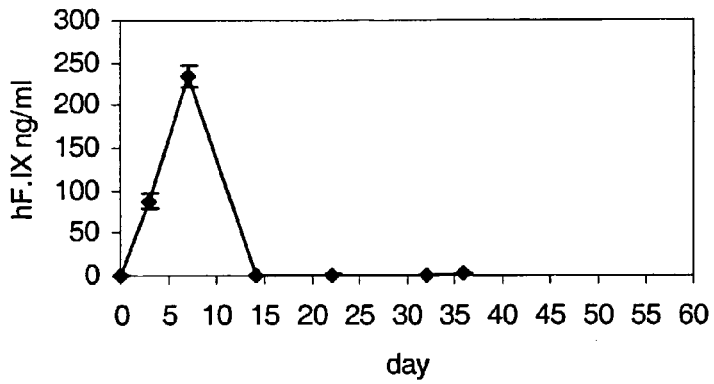
FIG. 22 depicts the constitutive expression of hF.IX driven by a CMV enhancer promoter in CD-1 mice.

In the constitutive expression group, plasmid encoding for hF.IX under control of the CMV promoter was injected in a manner similar to first group of animals. FIG. 22 shows expression of hF.IX driven by the CMV enhancer promoter in CD-1 mice. Expression peaked 7 days after injection. Similar to data obtained by constitutively expressing EPO in mice, by 12-15 days after injection hF.IX levels are back to baseline due to an immune response against hF.IX.

Figure 23:
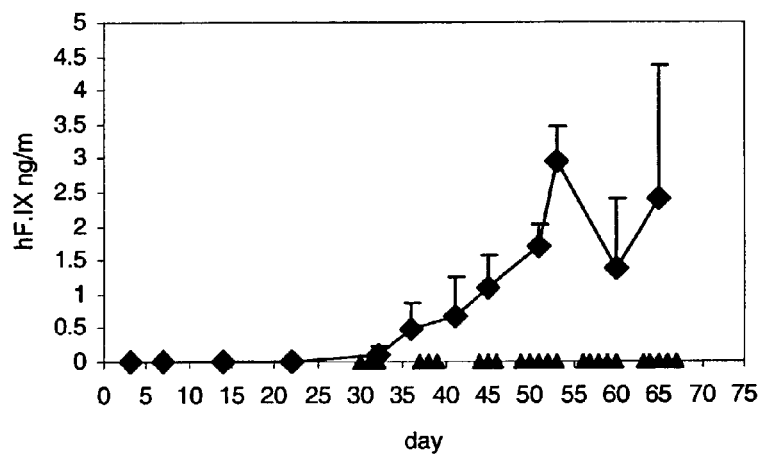
FIG. 23 depicts the regulated expression of hF.IX in CD-1 mice using an expression-regulated system according to one embodiment of the present invention. The first administration of mifepristone (filled triangles) was 28 days after injection.

In contrast, FIG. 23 shows the regulated expression of hF.IX in CD-1 mice according to one embodiment of the present invention. Initially, hF.IX levels were undetectable for four weeks prior to MFP activation of the GENESWITCH® system. The first administration of mifepristone (filled triangles) was 28 days after injection of the plasmids. After MFP treatment, the plasma levels of hF.IX increased over time. Even after 20 days from the start of MFP administration, the levels of hF.IX were still increasing. This was in contrast to the results using the CMV-hF.IX construct where expression was undetectable by 12 days after injection and electroporation. Furthermore, in the GENESWITCH® group, hF.IX levels were undetectable prior to activation of the system. After 4 weeks, hF.IX expression was activated by administration of mifepristone leading to detectable levels of hF.IX (FIG. 23).

In this particular example, removal of the drug for 4 days did not lead to a return to undetectable levels of hF.IX. Following two rounds of a pulsatile administration of mifepristone (3 days on and 4 days off) a more chronic administration protocol was adopted (5 days on and 2 days off). This led to increasing levels of hF.IX expression that reached a plateau level approximately 20 days after the initial mifepristone administration. Thus, FIG. 23 shows hF.IX expression that has been maintained for approximately 35 days which is clearly much longer than the duration of expression achieved in the constitutively active CMV group.

The development of a neutralizing immune response was also dramatically reduced by the GENESWITCH® regulated hF.IX expression and was further reduced by lengthening the lag period between plasmid delivery and the first induction of foreign transgene expression. The lag time necessary may be different with different delivery modalities. Delivery of plasmids with electroporation is associated with transient inflammation and cell infiltration. Inflammation may contribute to anti-hF.IX antibody production. The transient inflammation period following electroporation may last for approximately one month. Hence, it is preferred that foreign transgene expression be induced after inflammation at the muscle site has subsided. In addition, a pulsatile program of transgene expression may also reduce the neutralizing response by depriving the immune system of a source of antigen at certain critical times.

EXAMPLE 16

Regulated IFN-Alpha Gene Therapy Using the Plasmid-Based GENESWITCH® System

For the GENESWITCH® regulated IFN system two plasmids were utilized. The GENESWITCH® regulator protein used was a chimera of a truncated yeast GAL4 DNA binding domain (GAL4), the truncated human progesterone receptor ligand-binding domain and activation domain from the p65 subunit of human NF-kappaB (p65). The plasmid contains a muscle-specific promoter (avian skeletal a-actin promoter). The inducible plasmid pIF1681 encoding for human IFN-alpha2b (hIFN-alpha2b) contains the coding sequence for hIFN-alpha2b (NM_000605) inserted into a plasmid backbone that is essentially the same as that of pEP1666.

To induce expression, mifepristone in sesame oil was administered to mice (100 ml) orally by gavage at a 0.3 mg/kg dose. To prepare plasmid for injection, the plasmids were made in saline or formulated with 6 mg/ml poly-L-glutamate. In mice the injected volume of plasmid was 25 microliters into the tibialis and 50 microliters in the gastrocnemius muscle of the hindlimb. Following injection, caliper electrodes were positioned around the leg and compressed until snug (3-4 mm diameter between plates). Two 25 millisecond pulses at a voltage of 375 V/cm were then administered with a 700 millisecond delay between pulses using a T-830 Electro Square Porator (Genetronics, Inc., San Diego, Calif.). Colorimetric sandwich ELISAs where used for detection of interferon alpha protein and are commercially available.

Figure 24:
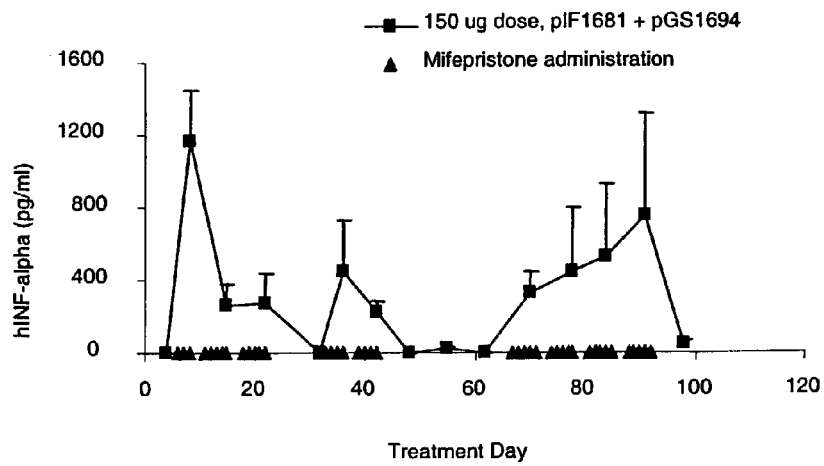
FIG. 24 depicts the regulated expression of hIFN-alpha2B in a mouse model.

FIG. 24 depicts the results of mifepristone-dependent regulation of hIFN-alpha expression in C57BL/6 mice. Plasmids for the hINF-alpha/GENESWITCH® system (1:1 mixtures of pIF1681 and pGS1694) were formulated with 6 mg/ml poly-L-glutamate in a total volume of 25 microliters and injected into the tibialis of mice followed by electroporation (375 V/cm, 2 pulses 25 ms each pulse). Total plasmid dose was 150 micrograms. Mifepristone dosing (0.33 mg/kg in 100 microliters given orally by gavage) was initiated 6 days after plasmids were delivered. Mean levels of hINF-alpha protein (±sem) are shown.

Prior to MFP dosing, hIFN-alpha levels were undetectable. In response to the first week of MFP dosing, hIFN-alpha protein was induced to a mean level of ~1.2 ng/ml. During the second and third weeks of MFP dosing, the induced level of hIFN was lower, reaching a mean value of ~200 pg/ml. During the second and third months, mean induced levels of hIFN protein were 200-700 pg/ml.

All patents and publications are hereby incorporated herein by reference as if they are fully set forth herein to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. Transformed cells, vectors, compositions, molecular switches and receptors, along with the methods, procedures, treatments and molecules described herein are exemplary and representative of preferred embodiments. They are not intended as limitations on the scope of the invention. Hence, changes to and combinations of the examples describe herein are encompassed within the spirit of the invention as defined by the scope of the claims.

SEQUENCE LISTING

```
<160> NUMBER OF SEQ ID NOS: 25

<210> SEQ ID NO 1
<211> LENGTH: 9
<212> TYPE: RNA
<213> ORGANISM: artificial
<220> FEATURE:
<223> OTHER INFORMATION: 5' splice site sequence of a synthetic intron

<400> SEQUENCE: 1 cagguaagu                                                                 9

<210> SEQ ID NO 2
<211> LENGTH: 9
<212> TYPE: RNA
<213> ORGANISM: Homo sapiens

<400> SEQUENCE: 2 guccauuca                                                                 9

<210> SEQ ID NO 3
<211> LENGTH: 7
```

```
<212> TYPE: RNA
<213> ORGANISM: artificial
<220> FEATURE:
<223> OTHER INFORMATION: branch point sequence for a synthetic intron

<400> SEQUENCE: 3 uacuaac                                                               7

<210> SEQ ID NO 4
<211> LENGTH: 6
<212> TYPE: RNA
<213> ORGANISM: Homo sapiens

<400> SEQUENCE: 4 augaug                                                                6

<210> SEQ ID NO 5
<211> LENGTH: 86
<212> TYPE: DNA
<213> ORGANISM: artificial
<220> FEATURE:
<223> OTHER INFORMATION: A general synthetic intron seqeuence where
      intronic sequences are represented by N, and  N can be any base
      and can be longer or shorter than depicted
<220> FEATURE:
<221> NAME/KEY: Intron
<222> LOCATION: (10)..(57)
<220> FEATURE:
<221> NAME/KEY: misc_feature
<222> LOCATION: (10)..(56)
<223> OTHER INFORMATION: n is a, c, g, or t
<220> FEATURE:
<221> NAME/KEY: misc_feature
<222> LOCATION: (64)..(65)
<223> OTHER INFORMATION: n is a, c, g, or t

<400> SEQUENCE: 5
caggtaagtn nnnnnnnnnn nnnnnnnnnn nnnnnnnnnn nnnnnnnnnn nnnnnntact    60
aacnnttctt tttttctctt cacagg                                         86

<210> SEQ ID NO 6
<211> LENGTH: 85
<212> TYPE: DNA
<213> ORGANISM: artificial
<220> FEATURE:
<223> OTHER INFORMATION: Consensus intron sequence wherein intronic
      sequencs are represented by N, and N can be any base and can be
      longer or shorter than depicted; M = C or A, R = A or G, Y = C or
      T
<220> FEATURE:
<221> NAME/KEY: variation
<222> LOCATION: (1)..(1)
<223> OTHER INFORMATION: m = C or A
<220> FEATURE:
<221> NAME/KEY: variation
<222> LOCATION: (6)..(6)
<223> OTHER INFORMATION: r = A or G
<220> FEATURE:
<221> NAME/KEY: Intron
<222> LOCATION: (10)..(58)
<220> FEATURE:
<221> NAME/KEY: misc_feature
<222> LOCATION: (10)..(57)
<223> OTHER INFORMATION: n is a, c, g, or t
<220> FEATURE:
<221> NAME/KEY: variation
<222> LOCATION: (58)..(82)
<223> OTHER INFORMATION: y = C or T
<220> FEATURE:
<221> NAME/KEY: misc_feature
<222> LOCATION: (59)..(59)
<223> OTHER INFORMATION: n is a, c, g, or t
```

```
<220> FEATURE:
<221> NAME/KEY: variation
<222> LOCATION: (62)..(62)
<223> OTHER INFORMATION: r = A or G
<220> FEATURE:
<221> NAME/KEY: misc_feature
<222> LOCATION: (81)..(81)
<223> OTHER INFORMATION: n is a, c, g, or t

<400> SEQUENCE: 6
maggtragtn nnnnnnnnnn nnnnnnnnnn nnnnnnnnnn nnnnnnnyny        60
trayyyyyyy yyyyyyyyyy nyagg                                   85

<210> SEQ ID NO 7
<211> LENGTH: 160
<212> TYPE: DNA
<213> ORGANISM: artificial
<220> FEATURE:
<223> OTHER INFORMATION: A synthetic intron termed IVS8 where exonic
      sequences are represented by N, N can be any base and can be
      longer or shorter
<220> FEATURE:
<221> NAME/KEY: misc_feature
<222> LOCATION: (1)..(10)
<223> OTHER INFORMATION: n is a, c, g, or t
<220> FEATURE:
<221> NAME/KEY: misc_feature
<222> LOCATION: (151)..(160)
<223> OTHER INFORMATION: n is a, c, g, or t

<400> SEQUENCE: 7
nnnnnnnnnn ttaattaaca ggtaagtgtc ttcctcctgt ttccttcccc ctgctattct   60
gctcaacctt cctatcagaa actgcagtat ctgtattttt gctagcagtt atactaacgg  120 ttctttttt ctcttcacag gccaccatgg nnnnnnnnnn                        160

<210> SEQ ID NO 8
<211> LENGTH: 110
<212> TYPE: DNA
<213> ORGANISM: artificial
<220> FEATURE:
<223> OTHER INFORMATION: 5' Untranslated region derived from CMV

<400> SEQUENCE: 8
tcagatcgcc tggagacgcc atccacgctg ttttgacctc catagaagac accgggaccg   60
atccagcctc cgcggccggg aacggtgcat tggaacgcgg attccccgtg             110

<210> SEQ ID NO 9
<211> LENGTH: 17
<212> TYPE: DNA
<213> ORGANISM: Saccharomyces cerevisiae

<400> SEQUENCE: 9
cggaagactc tcctccg                                                 17

<210> SEQ ID NO 10
<211> LENGTH: 93
<212> TYPE: PRT
<213> ORGANISM: Saccharomyces cerevisiae

<400> SEQUENCE: 10

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30
```

```
Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
     50                  55                  60

Glu Gln Leu Phe Leu Leu Ile Phe Pro Arg Glu Asp Leu Asp Met Ile
 65                  70                  75                  80

Leu Lys Met Asp Ser Leu Gln Asp Ile Lys Ala Leu Leu
             85                  90
```

<210> SEQ ID NO 11
<211> LENGTH: 28
<212> TYPE: PRT
<213> ORGANISM: artificial
<220> FEATURE:
<223> OTHER INFORMATION: General sequence for GAL4 DNA recognition unit
      having cysteine-rich amino acid sequence forming two alpha helices
      that bind to two Zn ions
<220> FEATURE:
<221> NAME/KEY: helix
<222> LOCATION: (1)..(28)
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(10)
<223> OTHER INFORMATION: Xaa can be any naturally occurring amino acid
<220> FEATURE:
<221> NAME/KEY: misc_feature
<222> LOCATION: (12)..(17)
<223> OTHER INFORMATION: Xaa can be any naturally occurring amino acid
<220> FEATURE:
<221> NAME/KEY: misc_feature
<222> LOCATION: (19)..(20)
<223> OTHER INFORMATION: Xaa can be any naturally occurring amino acid
<220> FEATURE:
<221> NAME/KEY: misc_feature
<222> LOCATION: (22)..(27)
<223> OTHER INFORMATION: Xaa can be any naturally occurring amino acid

<400> SEQUENCE: 11

```
Cys Xaa Xaa Cys Xaa Xaa Xaa Xaa Xaa Cys Xaa Xaa Xaa Xaa Xaa
 1               5                  10                  15

Xaa Cys Xaa Xaa Cys Xaa Xaa Xaa Xaa Xaa Xaa Cys
            20                  25
```

<210> SEQ ID NO 12
<211> LENGTH: 1965
<212> TYPE: DNA
<213> ORGANISM: artificial
<220> FEATURE:
<223> OTHER INFORMATION: Coding Sequence for the GeneSwitch regulator
      protein v.3.1comprising a GAL-4 DBD, a NFkBp65 transactivation
      domain and a mutated hPR LBD

<400> SEQUENCE: 12

| | | |
|---|---|---|
| atggactccc agcagccaga tctgaagcta ctgtcttcta tcgaacaagc atgcgatatt | 60 |
| tgccgactta aaaagctcaa gtgctccaaa gaaaaaccga gtgcgccaa gtgtctgaag | 120 |
| aacaactggg agtgtcgcta ctctcccaaa accaaaaggt ctccgctgac tagggcacat | 180 |
| ctgacagaag tggaatcaag gctagaaaga ctggaacagc tatttctact gattttccct | 240 |
| cgagaagacc ttgacatgat tttgaaaatg gattctttac aggatataaa agcattgtta | 300 |
| gaattcccgg gtgtcgacca gaaaaagttc aataaagtca gagttgtgag agcactggat | 360 |
| gctgttgctc tcccacagcc agtgggcgtt ccaaatgaaa gccaagccct aagccagaga | 420 |

-continued

```
ttcactttt  caccaggtca  agacatacag  ttgattccac  cactgatcaa  cctgttaatg    480
agcattgaac  cagatgtgat  ctatgcagga  catgacaaca  caaaacctga  cacctccagt    540
tctttgctga  caagtcttaa  tcaactaggc  gagaggcaac  ttctttcagt  agtcaagtgg    600
tctaaatcat  tgccaggttt  tcgaaactta  catattgatg  accagataac  tctcattcag    660
tattcttgga  tgagcttaat  ggtgtttggt  ctaggatgga  gatcctacaa  acacgtcagt    720
gggcagatgc  tgtattttgc  acctgatcta  atactaaatg  aacagcggat  gaaagaatca    780
tcattctatt  cattatgcct  taccatgtgg  cagatcccac  aggagtttgt  caagcttcaa    840
gttagccaag  aagagttcct  ctgtatgaaa  gtattgttac  ttcttaatac  aattcctttg    900
gaagggctac  gaagtcaaac  ccagtttgag  gagatgaggt  caagctacat  tagagagctc    960
atcaaggcaa  ttggtttgag  gcaaaaagga  gttgtgtcga  gctcacagcg  tttctatcaa   1020
cttacaaaac  ttcttgataa  cttgcatgat  cttgtcaaac  aacttcatct  gtactgcttg   1080
aatacattta  tccagtcccg  ggcactgagt  gttgaatttc  cagaaatgat  gtctgaagtt   1140
attgctgggt  cgacgcccat  ggaattccag  tacctgccag  atacagacga  tcgtcaccgg   1200
attgaggaga  aacgtaaaag  gacatatgag  accttcaaga  gcatcatgaa  gaagagtcct   1260
ttcagcggac  ccaccgaccc  ccggcctcca  cctcgacgca  ttgctgtgcc  ttcccgcagc   1320
tcagcttctg  tccccaagcc  agcacccag  ccctatccct  ttacgtcatc  cctgagcacc   1380
atcaactatg  atgagtttcc  caccatggtg  tttccttctg  ggcagatcag  ccaggcctcg   1440
gccttggccc  cggcccctcc  ccaagtcctg  ccccaggctc  cagcccctgc  ccctgctcca   1500
gccatggtat  cagctctggc  ccaggcccca  gcccctgtcc  cagtcctagc  cccaggccct   1560
cctcaggctg  tgggccccacc  tgcccccaag  cccacccagg  ctggggaagg  aacgctgtca   1620
gaggccctgc  tgcagctgca  gtttgatgat  gaagacctgg  gggccttgct  tggcaacagc   1680
acagacccag  ctgtgttcac  agacctggca  tccgtcgaca  actccgagtt  tcagcagctg   1740
ctgaaccagg  gcatacctgt  gggccccccac  acaactgagc  ccatgctgat  ggagtaccct   1800
gaggctataa  ctcgcctagt  gacaggggcc  cagaggcccc  ccgacccagc  tcctgctcca   1860
ctgggggccc  cggggctccc  caatggcctc  cttttcaggag  atgaagactt  ctcctccatt   1920
gcggacatgg  acttctcagc  cctgctgagt  cagatcagct  cctaa                    1965
```

<210> SEQ ID NO 13
<211> LENGTH: 1893
<212> TYPE: DNA
<213> ORGANISM: artificial
<220> FEATURE:
<223> OTHER INFORMATION: Coding Sequence for GeneSwitch Regulator protein v.4.0 comprising
a truncated GAL4 DBD, p65 transactivation domain and mutated hPR
LBD

<400> SEQUENCE: 13

```
atggactccc  agcagccaga  tctgaagcta  ctgtcttcta  tcgaacaagc  atgcgatatt     60
tgccgactta  aaaagctcaa  gtgctccaaa  gaaaaaccga  agtgcgccaa  gtgtctgaag    120
aacaactggg  agtgtcgcta  ctctcccaaa  accaaaaggt  ctccgctgac  tagggcacat    180
ctgacagaag  tggaatcaag  gctagaaaga  ctggaacagc  tatttctact  gattttcct     240
cgagaccaga  aaaagttcaa  taaagtcaga  gttgtgagag  cactgattgc  tgttgctctc    300
ccacagccag  tgggcgttcc  aaatgaaagc  caagccctaa  gccagagatt  cactttttca    360
ccaggtcaag  acatacagtt  gattccacca  ctgatcaacc  tgttaatgag  cattgaacca    420
gatgtgatct  atgcaggaca  tgacaacaca  aaacctgaca  cctccagttc  tttgctgaca    480
agtcttaatc  aactaggcga  gaggcaactt  ctttcagtag  tcaagtggtc  taaatcattg    540
ccaggtttc  gaaacttaca  tattgatgac  cagataactc  tcattcagta  ttcttggatg    600
agcttaatgg  tgtttggtct  aggatggaga  tcctacaaac  acgtcagtgg  gcagatgctg    660
tattttgcac  ctgatctaat  actaaatgaa  cagcggatga  agaatcatc  attctattca    720
ttatgcctta  ccatgtggca  gatcccacag  gagtttgtca  agcttcaagt  tagccaagaa    780
```

-continued

```
gagttcctct gtatgaaagt attgttactt cttaatacaa ttccttggga agggctacga    840
agtcaaaccc agtttgagga gatgaggtca agctacatta gagagctcat caaggcaatt    900
ggtttgaggc aaaaaggagt tgtgtcgagc tcacagcgtt tctatcaact tacaaaactt    960
cttgataact tgcatgatct tgtcaaacaa cttcatctgt actgcttgaa tacatttatc   1020
cagtcccggg cactgagtgt tgaatttcca gaaatgatgt ctgaagttat tgctgggtcg   1080
acgcccatgg aattccagta cctgccagat acagacgatc gtcaccggat tgaggagaaa   1140
cgtaaaagga catatgagac cttcaagagc atcatgaaga agagtccttt cagcggaccc   1200
accgacccc ggcctccacc tcgacgcatt gctgtgcctt cccgcagctc agcttctgtc    1260
cccaagccag caccccagcc ctatcccttt acgtcatccc tgagcaccat caactatgat   1320
gagtttccca ccatggtgtt tccttctggg cagatcagcc aggcctcggc cttggccccg   1380
gcccctcccc aagtcctgcc ccaggctcca gcccctgccc ctgctccagc catggtatca   1440
gctctggccc aggcccagc ccctgtccca gtcctagccc caggccctcc tcaggctgtg    1500
gccccacctg ccccaagcc cacccaggct ggggaaggaa cgctgtcaga ggccctgctg   1560
cagctgcagt ttgatgatga agacctgggg gccttgcttg caacagcac agacccagct    1620
gtgttcacag acctggcatc cgtcgacaac tccgagtttc agcagctgct gaaccagggc   1680
atacctgtgg cccccacac aactgagccc atgctgatgg agtaccctga ggggccccg    1740
cgcctagtga caggggccca gaggcccccc gacccagctc ctgctccact ggggccccg    1800
gggctcccca atggcctcct tcaggagat gaagactcc cctccattgc ggacatggac    1860
ttctcagccc tgctgagtca gatcagctcc taa                                1893
```

<210> SEQ ID NO 14
<211> LENGTH: 654
<212> TYPE: PRT
<213> ORGANISM: artificial
<220> FEATURE:
<223> OTHER INFORMATION: Amino acid sequence of GeneSwitch regulator protein v. 3.1comprising GAL4 BD, p65 transactivation domain and mutated hPR LBD

<400> SEQUENCE: 14

```
Met Asp Ser Gln Gln Pro Asp Leu Lys Leu Leu Ser Ser Ile Glu Gln
1               5                   10                  15
Ala Cys Asp Ile Cys Arg Leu Lys Lys Leu Lys Cys Ser Lys Glu Lys
                20                  25                  30
Pro Lys Cys Ala Lys Cys Leu Lys Asn Asn Trp Glu Cys Arg Tyr Ser
            35                  40                  45
Pro Lys Thr Lys Arg Ser Pro Leu Thr Arg Ala His Leu Thr Glu Val
        50                  55                  60
Glu Ser Arg Leu Glu Arg Leu Glu Gln Leu Phe Leu Leu Ile Phe Pro
65                  70                  75                  80
Arg Glu Asp Leu Asp Met Ile Leu Lys Met Asp Ser Leu Gln Asp Ile
                85                  90                  95
Lys Ala Leu Leu Glu Phe Pro Gly Val Asp Gln Lys Leu Phe Asn Lys
                100                 105                 110
Val Arg Val Val Arg Ala Leu Asp Ala Val Ala Leu Pro Gln Pro Val
            115                 120                 125
Gly Val Pro Asn Glu Ser Gln Ala Leu Ser Gln Arg Phe Thr Phe Ser
        130                 135                 140
Pro Gly Gln Asp Ile Gln Leu Ile Pro Pro Leu Ile Asn Leu Leu Met
145                 150                 155                 160
Ser Ile Glu Pro Asp Val Ile Tyr Ala Gly His Asp Asn Thr Lys Pro
                165                 170                 175
Asp Thr Ser Ser Ser Leu Leu Thr Ser Leu Asn Gln Leu Gly Glu Arg
                180                 185                 190
Gln Leu Leu Ser Val Val Lys Trp Ser Lys Ser Leu Pro Gly Phe Arg
            195                 200                 205
Asn Leu His Ile Asp Asp Gln Ile Thr Leu Ile Gln Tyr Ser Trp Met
        210                 215                 220
Ser Leu Met Val Phe Gly Leu Gly Trp Arg Ser Tyr Lys His Val Ser
225                 230                 235                 240
Gly Gln Met Leu Tyr Phe Ala Pro Asp Leu Ile Leu Asn Glu Gln Arg
                245                 250                 255
Met Lys Glu Ser Ser Phe Tyr Ser Leu Cys Leu Thr Met Trp Gln Ile
                260                 265                 270
Pro Gln Glu Phe Val Lys Leu Gln Val Ser Gln Glu Glu Phe Leu Cys
            275                 280                 285
Met Lys Val Leu Leu Leu Leu Asn Thr Ile Pro Leu Glu Gly Leu Arg
        290                 295                 300
Ser Gln Thr Gln Phe Glu Glu Met Arg Ser Ser Tyr Ile Arg Glu Leu
305                 310                 315                 320
Ile Lys Ala Ile Gly Leu Arg Gln Lys Gly Val Val Ser Ser Ser Gln
                325                 330                 335
Arg Phe Tyr Gln Leu Thr Lys Leu Leu Asp Asn Leu His Asp Leu Val
                340                 345                 350
Lys Gln Leu His Leu Tyr Cys Leu Asn Thr Phe Ile Gln Ser Arg Ala
            355                 360                 365
Leu Ser Val Glu Phe Pro Glu Met Met Ser Glu Val Ile Ala Gly Ser
```

-continued

```
            370                 375                 380
Thr Pro Met Glu Phe Gln Tyr Leu Pro Asp Thr Asp Asp Arg His Arg
385                 390                 395                 400
Ile Glu Glu Lys Arg Lys Arg Thr Tyr Glu Thr Phe Lys Ser Ile Met
                405                 410                 415
Lys Lys Ser Pro Phe Ser Gly Pro Thr Asp Pro Arg Pro Pro Pro Arg
            420                 425                 430
Arg Ile Ala Val Pro Ser Arg Ser Ser Ala Ser Val Pro Lys Pro Ala
        435                 440                 445
Pro Gln Pro Tyr Pro Phe Thr Ser Ser Leu Ser Thr Ile Asn Tyr Asp
    450                 455                 460
Glu Phe Pro Thr Met Val Phe Pro Ser Gly Gln Ile Ser Gln Ala Ser
465                 470                 475                 480
Ala Leu Ala Pro Ala Pro Pro Gln Val Leu Pro Gln Ala Pro Ala Pro
                485                 490                 495
Ala Pro Ala Pro Ala Met Val Ser Ala Leu Ala Gln Ala Pro Ala Pro
                500                 505                 510
Val Pro Val Leu Ala Pro Gly Pro Pro Gln Ala Val Ala Pro Pro Ala
            515                 520                 525
Pro Lys Pro Thr Gln Ala Gly Glu Gly Thr Leu Ser Glu Ala Leu Leu
        530                 535                 540
Gln Leu Gln Phe Asp Asp Glu Asp Leu Gly Ala Leu Leu Gly Asn Ser
545                 550                 555                 560
Thr Asp Pro Ala Val Phe Thr Asp Leu Ala Ser Val Asp Asn Ser Glu
                565                 570                 575
Phe Gln Gln Leu Leu Asn Gln Gly Ile Pro Val Ala Pro His Thr Thr
            580                 585                 590
Glu Pro Met Leu Met Glu Tyr Pro Glu Ala Ile Thr Arg Leu Val Thr
        595                 600                 605
Gly Ala Gln Arg Pro Pro Asp Pro Ala Pro Ala Pro Leu Gly Ala Pro
    610                 615                 620
Gly Leu Pro Asn Gly Leu Leu Ser Gly Asp Glu Asp Phe Ser Ser Ile
625                 630                 635                 640
Ala Asp Met Asp Phe Ser Ala Leu Leu Ser Gln Ile Ser Ser
                645                 650
```

<210> SEQ ID NO 15
<211> LENGTH: 630
<212> TYPE: PRT
<213> ORGANISM: artificial
<220> FEATURE:
<223> OTHER INFORMATION: Amino acid sequence for GeneSwitch regulator protein v.4.0 comprising truncated GAL4 DBD, p65 transactivation domain and mutated hPR LBD.

<400> SEQUENCE: 15

```
Met Asp Ser Gln Gln Pro Asp Leu Lys Leu Leu Ser Ser Ile Glu Gln
1               5                   10                  15
Ala Cys Asp Ile Cys Arg Leu Lys Lys Leu Lys Cys Ser Lys Glu Lys
                20                  25                  30
Pro Lys Cys Ala Lys Cys Leu Lys Asn Asn Trp Glu Cys Arg Tyr Ser
            35                  40                  45
Pro Lys Thr Lys Arg Ser Pro Leu Thr Arg Ala His Leu Thr Glu Val
        50                  55                  60
Glu Ser Arg Leu Glu Arg Leu Glu Gln Leu Phe Leu Leu Ile Phe Pro
65                  70                  75                  80
Arg Asp Gln Lys Lys Phe Asn Lys Val Arg Val Val Arg Ala Leu Asp
                85                  90                  95
Ala Val Ala Leu Pro Gln Pro Val Gly Val Pro Asn Glu Ser Gln Ala
                100                 105                 110
Leu Ser Gln Arg Phe Thr Phe Ser Pro Gly Gln Asp Ile Gln Leu Ile
            115                 120                 125
Pro Pro Leu Ile Asn Leu Leu Met Ser Ile Glu Pro Asp Val Ile Tyr
        130                 135                 140
Ala Gly His Asp Asn Thr Lys Pro Asp Thr Ser Ser Ser Leu Leu Thr
145                 150                 155                 160
Ser Leu Asn Gln Leu Gly Glu Arg Gln Leu Leu Ser Val Val Lys Trp
                165                 170                 175
Ser Lys Ser Leu Pro Gly Phe Arg Asn Leu His Ile Asp Asp Gln Ile
            180                 185                 190
Thr Leu Ile Gln Tyr Ser Trp Met Ser Leu Met Val Phe Gly Leu Gly
        195                 200                 205
Trp Arg Ser Tyr Lys His Val Ser Gly Gln Met Leu Tyr Phe Ala Pro
    210                 215                 220
Asp Leu Ile Leu Asn Glu Gln Arg Met Lys Glu Ser Ser Phe Tyr Ser
225                 230                 235                 240
Leu Cys Leu Thr Met Trp Gln Ile Pro Gln Glu Phe Val Lys Leu Gln
```

|     |     |     |     | 245 |     |     |     |     | 250 |     |     |     |     | 255 |     |
Val | Ser | Gln | Glu | Glu | Phe | Leu | Cys | Met | Lys | Val | Leu | Leu | Leu | Leu | Asn
Thr | Ile | Pro | Leu | Glu | Gly | Leu | Arg | Ser | Gln | Thr | Gln | Phe | Glu | Glu | Met
        260                           265                           270
Arg | Ser | Ser | Tyr | Ile | Arg | Glu | Leu | Ile | Lys | Ala | Ile | Gly | Leu | Arg | Gln
        275                           280                           285
Lys | Gly | Val | Val | Ser | Ser | Gln | Arg | Phe | Tyr | Gln | Leu | Thr | Lys | Leu
290                           295                           300
305                           310                           315                           320
Leu | Asp | Asn | Leu | His | Asp | Leu | Val | Lys | Gln | Leu | His | Leu | Tyr | Cys | Leu
                    325                           330                           335
Asn | Thr | Phe | Ile | Gln | Ser | Arg | Ala | Leu | Ser | Val | Glu | Phe | Pro | Glu | Met
              340                           345                           350
Met | Ser | Glu | Val | Ile | Ala | Gly | Ser | Thr | Pro | Met | Glu | Phe | Gln | Tyr | Leu
        355                           360                           365
Pro | Asp | Thr | Asp | Asp | Arg | His | Arg | Ile | Glu | Glu | Lys | Arg | Lys | Arg | Thr
370                           375                           380
Tyr | Glu | Thr | Phe | Lys | Ser | Ile | Met | Lys | Lys | Ser | Pro | Phe | Ser | Gly | Pro
385                           390                           395                           400
Thr | Asp | Pro | Arg | Pro | Pro | Arg | Arg | Ile | Ala | Val | Pro | Ser | Arg | Ser
                    405                           410                           415
Ser | Ala | Ser | Val | Pro | Lys | Pro | Ala | Pro | Gln | Pro | Tyr | Pro | Phe | Thr | Ser
              420                           425                           430
Ser | Leu | Ser | Thr | Ile | Asn | Tyr | Asp | Glu | Phe | Pro | Thr | Met | Val | Phe | Pro
        435                           440                           445
Ser | Gly | Gln | Ile | Ser | Gln | Ala | Ser | Ala | Leu | Ala | Pro | Ala | Pro | Pro | Gln
    450                           455                           460
Val | Leu | Pro | Gln | Ala | Pro | Ala | Pro | Ala | Pro | Ala | Pro | Ala | Met | Val | Ser
465                           470                           475                           480
Ala | Leu | Ala | Gln | Ala | Pro | Ala | Pro | Val | Pro | Val | Leu | Ala | Pro | Gly | Pro
                    485                           490                           495
Pro | Gln | Ala | Val | Ala | Pro | Pro | Ala | Pro | Lys | Pro | Thr | Gln | Ala | Gly | Glu
              500                           505                           510
Gly | Thr | Leu | Ser | Glu | Ala | Leu | Leu | Gln | Leu | Gln | Phe | Asp | Asp | Glu | Asp
        515                           520                           525
Leu | Gly | Ala | Leu | Leu | Gly | Asn | Ser | Thr | Asp | Pro | Ala | Val | Phe | Thr | Asp
    530                           535                           540
Leu | Ala | Ser | Val | Asp | Asn | Ser | Glu | Phe | Gln | Gln | Leu | Leu | Asn | Gln | Gly
545                           550                           555                           560
Ile | Pro | Val | Ala | Pro | His | Thr | Thr | Glu | Pro | Met | Leu | Met | Glu | Tyr | Pro
                    565                           570                           575
Glu | Ala | Ile | Thr | Arg | Leu | Val | Thr | Gly | Ala | Gln | Arg | Pro | Pro | Asp | Pro
              580                           585                           590
Ala | Pro | Ala | Pro | Leu | Gly | Ala | Pro | Gly | Leu | Pro | Asn | Gly | Leu | Leu | Ser
        595                           600                           605
Gly | Asp | Glu | Asp | Phe | Ser | Ser | Ile | Ala | Asp | Met | Asp | Phe | Ser | Ala | Leu
    610                           615                           620
Leu | Ser | Gln | Ile | Ser | Ser
625                           630

<210> SEQ ID NO 16
<211> LENGTH: 439
<212> TYPE: DNA
<213> ORGANISM: Gallus gallus

<400> SEQUENCE: 16

```
gggccgctct agctagagtc tgcctgcccc ctgcctggca cagcccgtac ctggccgcac     60
gctccctcac aggtgaagct cgaaaactcc gtccccgtaa ggagcccgc tgcccccga     120
ggcctcctcc ctcacgcctc gctgcgctcc cggctcccgc acggccctgg gagaggcccc    180
caccgcttcg tccttaacgg gcccggcggt gccggggat tatttcggcc ccggcccgg     240
gggggcccgg cagacgctcc ttatacggcc cggcctcgct cacctgggcc gcggccagga    300
gcgccttctt tgggcagcgc cggccggggg ccgcgccggg cccgacaccc aaatatggcg    360
acggccgggg ccgcattcct ggggccgggg cggtgctccc gcccgcctcg ataaaaggct    420
ccggggccgg cgggcgact                                                 439
```

<210> SEQ ID NO 17
<211> LENGTH: 176
<212> TYPE: DNA
<213> ORGANISM: artificial
<220> FEATURE:
<223> OTHER INFORMATION: Core promoter region comprising a TATA box, (16) to (23), a putative initiation region (inr), (35) to (64), from the CMV promoter, and a 5'UTR, (59) to (175), from CMV.

<400> SEQUENCE: 17

```
            gtcgactcta gagggtatat aatggatctc gagatatcgg agctcgttta gtgaaccgtc        60
            agatcgcctg gagacgccat ccacgctgtt ttgacctcca tagaagacac cggaccgat         120
            ccagcctccg cggcgggaa cggtgcattg aacgcggat tccccgtgtt aattaa              176
```

<210> SEQ ID NO 18
<211> LENGTH: 184
<212> TYPE: DNA
<213> ORGANISM: artificial
<220> FEATURE:
<223> OTHER INFORMATION: pEP1556 -intact inducible promoter region comprising a TATA box,
      initiation region (inr) and a UT12 Transcription factor binding
      site (TFBS)

<400> SEQUENCE: 18

```
            ccgagtcgac tctagagggt atataatgga tctcgagata tcggagctcg tttagtgaac         60
            cgtcagatcg cctggagacg ccatccacgc tgttttgacc tccatagaag acaccgggac        120
            cgatccagcc tccgcggccg ggaacggtgc attggaacgc ggattccccg tgttaattaa        180
            cagg                                                                    184
```

<210> SEQ ID NO 19
<211> LENGTH: 154
<212> TYPE: DNA
<213> ORGANISM: artificial
<220> FEATURE:
<223> OTHER INFORMATION: pEP 1595 core promoter having a Sal 1/EcoRV deletion of the TATA
      box leaving only the inr and theUT-12  TFBS regions

<400> SEQUENCE: 19

```
            ccgagtcgaa tcggagctcg tttagtgaac cgtcagatcg cctggagacg ccatccacgc         60
            tgttttgacc tccatagaag acaccgggac cgatccagcc tccgcggccg ggaacggtgc        120
            attggaacgc ggattccccg tgttaattaa cagg                                    154
```

<210> SEQ ID NO 20
<211> LENGTH: 154
<212> TYPE: DNA
<213> ORGANISM: artificial
<220> FEATURE:
<223> OTHER INFORMATION: pEP1596 core promoter having a EcoR/ BsmBI deletion of the inr
      region leaving only the TATA box and the UT12-TFBS

<400> SEQUENCE: 20

```
            ccgagtcgac tctagagggt atataatgga tctcgagatg cctggagacg ccatccacgc         60
            tgttttgacc tccatagaag acaccgggac cgatccagcc tccgcggccg ggaacggtgc        120
            attggaacgc ggattccccg tgttaattaa cagg                                    154
```

<210> SEQ ID NO 21
<211> LENGTH: 140
<212> TYPE: DNA
<213> ORGANISM: artificial
<220> FEATURE:
<223> OTHER INFORMATION: pEP1597 core promoter having a SacII/PacI deletion of UT12 TFBS
      leaving only the TATA box and the inr region

<400> SEQUENCE: 21

```
            ccgagtcgac tctagagggt atataatgga tctcgagata tcggagctcg tttagtgaac         60
            cgtcagatcg cctggagacg ccatccacgc tgttttgacc tccatagaag acaccgggac        120
            cgatccagcc tcctaacagg                                                    140
```

<210> SEQ ID NO 22
<211> LENGTH: 5566
<212> TYPE: DNA
<213> ORGANISM: artificial
<220> FEATURE:
<223> OTHER INFORMATION: Complete nucleic acid sequence of pGS 1694 plasmid

<400> SEQUENCE: 22

```
            ggggccgctc tagctagagt ctgcctgccc cctgcctggc acagccgta cctggccgca          60
            cgctccctca caggtgaagc tcgaaaactc cgtccccgta aggagccccg ctgcccccg         120
            aggcctcctc cctcacgcct cgctgcgctc ccggctcccg cacgccctg ggagagggcc         180
```

```
ccaccgcttc gtccttaacg ggcccggcgg tgccggggga ttatttcggc cccggccccg    240
gggggggccg gcagacgctc cttatacggc ccggcctcgc tcacctgggc cgcggccagg    300
agcgccttct ttgggcagcg ccgggccggg gccgcgccgg gcccgacacc caaatatggc    360
gacggccggg gccgcattcc tgggggccgg gcggtgctcc cgcccgcctc gataaaaggc    420
tccggggccg gcgggcgact cagatcgcct ggagacgcca tccacgctgt tttgacctcc    480
atagaagaca ccgggaccga tccagcctcc gcggccggga acggtgcatt ggaacgcgga    540
ttccccgtgt taattaacag gtaagtgtct cctcctgtt tccttcccct gctattctgc     600
tcaaccttcc tatcagaaac tgcagtatct gtattttgc tagcagtaat actaacggtt     660
cttttttct cttcacaggc caccaagcta ccgtccacc atggactccc agcagccaga      720
tctgaagcta ctgtcttcta tcgaacaagc atgcgatatt tgccgactta aaaagctcaa    780
gtgctccaaa gaaaaccga agtgcgccaa gtgtctgaag aacaactggg agtgtcgcta     840
ctctcccaaa accaaaaggt ctccgctgac tagggcacat ctgacagaag tggaatcaag    900
gctagaaaga ctggaacagc tatttctact gattttcct cgagaccaga aaaagttcaa     960
taaagtcaga gttgtgagag cactggatgc tgttgctctc ccacagccag tgggcgttcc   1020
aaatgaaagc caagccctaa gccagagatt cacttttca ccaggtcaag acatacagtt    1080
gattccacca ctgatcaacc tgttaatgaa cattgaacca gatgtgatct atgcaggaca   1140
tgacaacaca aaacctgaca cctccagttc tttgctgaca agtcttaatc aactaggcga   1200
gaggcaactt ctttcagtag tcaagtggtc taaatcattg ccaggttttc gaaacttaca   1260
tattgatgac cagataactc tcattcagta ttcttggatg agcttaatgg tgtttggtct   1320
aggatggaga tcctacaaac acgtcagtgg gcagatgctg tattttgcac ctgatctaat   1380
actaaatgaa cagcggatga aagaatcatc attctattca ttatgcctta ccatgtggca   1440
gatcccacag gagtttgtca agcttcaagt tagccaagaa gagttcctct gtatgaaagt   1500
attgttactt cttaatacaa ttcctttgga agggctacga agtcaaaccc agtttgagga   1560
gatgaggtca agctacatta gagagctcat caaggcaatt ggtttgaggc aaaaaggagt   1620
tgtgtcgagc tcacagcgtt tctatcaact tacaaaactt cttgataact tgcatgatct   1680
tgtcaaacaa cttcatctgt actgcttgaa tacatttatc cagtcccggg cactgagtgt   1740
tgaatttcca gaaatgatgt ctgaagttat tgctgggtcg acgcccatgg aattccagta   1800
cctgccagat acagacgatc gtcaccggat tgaggagaaa cgtaaaagga catatgagac   1860
cttcaagagc atcatgaaga agagtccttt cagcggaccc accgaccccc ggcctccacc   1920
tcgacgcatt gctgtgcctt cccgcagctc agcttctgtc cccaagccag caccccagcc   1980
ctatcccttt acgtcatccc tgagcaccat caactatgat gagttttcca ccatggtgtt   2040
tccttctggg cagatcagcc aggcctcggc cttggcccg gcccctccc aagtcctgcc     2100
ccaggctcca gccccctgcc ctgctccagc catggtatca gctctggccc aggccccagc   2160
ccctgtccca gtccctagccc caggccctcc tcaggctgtg gcccacctg cccccaagcc    2220
cacccaggct ggggaaggaa cgctgtcaga ggccctgctg cagctgcagt tgatgatga    2280
agacctgggg gccttgcttg gcaacagcac agacccagct gtgttcacag acctggcatc   2340
cgtcgacaac tccgagtttc agcagctgct gaaccagggc ataccgtgg cccccacac    2400
aactgagccc atgctgatgg agtaccctga ggctataact cgcctagtga caggggccca   2460
gaggccccccc gacccagctc ctgctccact gggggcccccg gggctcccca atggcctcct   2520
ttcaggagat gaagacttct cctccattgc ggacatggac ttctcagccc tgctgagtca   2580
gatcagctcc taaggatcct ccggactaga aaagccgagc tctgcaggaa ttgggtggca   2640
tccctgtgac ccctcccccag tgcctctcct ggcctgaa gttgccactc cagtgccac    2700
cagccttgtc ctaataaaat taagttgcat cattttgtct gactaggtgt ccttctataa   2760
tattatgggg tggaggggggg tggtatggag caaggggcaa gttgggaaga caacctgtag   2820
ggctcgaggg ggggcccggt acgatctgcc ggtctcccta tagtgagtcg tattaatttc   2880
gataagccag gttaacctgc attaatgaat cggccaacgc gcggggagag gcggtttgcg   2940
tattgggcgc tcttccgctt cctcgctcac tgactcgctg cgctcggtcg ttcggctgcg   3000
gcgagcggta tcagctcact caaaggcggt aatacggtta ccacagaat caggggataa    3060
cgcaggaaag aacatgtgag caaaaggcca gcaaaggcc aggaaccgta aaaaggccgc     3120
gttgctggcg ttttccata ggctccgccc cctgacgag catcacaaaa atcgacgctc     3180
aagtcagagg tggcgaaacc cgacaggact ataaagatac caggcgtttc ccctggaag    3240
ctccctcgtg cgctctcctg ttccgaccct gccgcttacc ggatacctgt ccgcctttct    3300
cccttcggga agcgtggcgc tttctcatag ctcacgctgt aggtatctca gttcggtgta   3360
ggtcgttcgc tccaagctgg gctgtgtgca cgaaccccc gttccgcccg accgctgcgc    3420
cttatccggt aactatcgtc ttgagtccaa cccggtaaga cacgacttat cgccactggc   3480
agcagccact ggtaacagga ttagcagagc gaggtatgta ggcggtgcta cagagttctt    3540
gaagtggtgg cctaactacg gctacactag aagaacagta tttggtatct gcgctctgct   3600
gaagccagtt accttcggaa aaagagttgg tagctcttga tccggcaaac aaaccaccgc   3660
tggtagcggt ggtttttttg tttgcaagca gcagattacg cgcagaaaaa aaggatctca   3720
agaagatcct ttgatctttt ctacggggtc tgacgctcag tggaacgaaa actcacgtta   3780
agggattttg gtcatgagcg cgcctaggct tttgcaaaga tcgatcaaga gacaggatga   3840
ggatcgtttc gcatgattga acaagatgga ttgcacgcag gttctccggc cgcttgggtg   3900
gagaggctat tcggctatga ctgggcacaa cagacaatcg gctgctctga tgccgccgtg   3960
ttccgctgt cagcgcaggg gcgcccggtt cttttttgtca agaccgacct gtccggtgcc    4020
ctgaatgaac tgcaagacga ggcagcgcgg ctatcgtggc tggccacgac gggcgttcct   4080
tgcgcagctg tgctcgacgt tgtcactgaa gcgggaaggg actggctgct attgggcgaa   4140
gtgccggggc aggatctcct gtcatctcac cttgctcctg ccgagaaagt atccatcatg   4200
gctgatgcaa tgcggcggct gcatacgctt gatccggcta cctgcccatt cgaccaccaa   4260
gcgaaacatc gcatcgagcg agcacgtact cggatggaag ccggtcttgt cgatcaggat   4320
gatctggacg aagagcatca ggggctcgcg ccagccgaac tgttcgccag gctcaaggcg   4380
agcatgcccg acggcgagga tctcgtcgtg acccatggcg atgcctgctt gccgaatatc   4440
atggtggaaa atggccgctt ttctggattc atcgactgtg gccggctggg tgtggcggac   4500
cgctatcagg acatagcgtt ggctacccgt gatattgctg aagagcttgg cggcgaatgg   4560
gctgaccgct tcctcgtgct ttacggtatc gccgctcccg attcgcagcg catcgccttc   4620
tatcgccttc ttgacgagtt cttctgagcg ggactctggg gttcgaaatg accgaccaag   4680
cgacgcccaa cctgccatca cgagatttcg attccaccgc cgccttctat gaaaggttgg   4740
gcttcggaat cgttttccgg gacgccggct ggatgatcct ccagcgcggg gatctcatgc   4800
tggagttctt cgcccaccct aggcgcgctc atgagcggat acatatttga atgtatttag   4860
aaaaataaac aaataggggt tccgcgcaca tttccccgaa aagtgccacc taaattgtaa   4920
```

```
                gcgttaatat tttgttaaaa ttcgcgttaa attttttgtta aatcagctca ttttttaacc    4980
                aataggccga aatcggcaaa atcccttata aatcaaaaga atagaccgag atagggttga    5040
                gtgttgttcc agtttggaac aagagtccac tattaaagaa cgtggactcc aacgtcaaag    5100
                ggcgaaaaac cgtctatcag ggcgatggcc cactacgtga accatcaccc taatcaagtt    5160
                ttttggggtc gaggtgccgt aaagcactaa atcggaaccc taaagggagc ccccgattta    5220
                gagcttgacg gggaaagccg gcgaacgtgg cgagaaagga agggaagaaa gcgaaaggag    5280
                cgggcgctag ggcgctggca agtgtagcgg tcacgctgcg cgtaaccacc acacccgccg    5340
                cgcttaatgc gccgctacag ggcgcgtccc attcgccatt caggctgcgc aactgttggg    5400
                aagggcgatc ggtgcgggcc tcttcgctat tacgccagct ggcgaaaggg ggatgtgctg    5460
                caaggcgatt aagttgggta acgccaggt tttcccagtc acgacgttgt aaaacgacgg    5520
                ccagtgagcg cgcgtaatac gactcactat agggcgaatt gggtac                     5566

<210> SEQ ID NO 23
<211> LENGTH: 3100
<212> TYPE: DNA
<213> ORGANISM: artificial
<220> FEATURE:
<223> OTHER INFORMATION: Complete nucleic acid sequence of pEP1666 plasmid.

<400> SEQUENCE: 23
gggtcgaagc ggagtactgt cctccgagtg gagtactgtc ctccgagcgg agtactgtcc      60
                tccgagtcga gggtcgaagc ggagtactgt cctccgagtg gagtactgtc ctccgagcgg     120
                agtactgtcc tccgagtcga ctctagaggg tatataatgg atctcgagat gcctggagac     180
                gccatccacg ctgtttttgac ctccatagaa gacaccggga ccgatccagc ctccgcggcc     240
                gggaacggtg cattggaacg cggattcccc gtgttaatta acaggtaagt gtcttcctcc     300
                tgtttccttc ccctgctatt ctgctcaacc ttcctatcag aaactgcagt atctgtattt     360
                ttgctagcag taatactaac ggttcttttt ttctcttcac aggccaccaa gcttccatgg     420
                gggtgcacga atgtcctgcc tggctgtggc tgctcctgtc cctgctgtcc ctccctctgg     480
                gcctcccagt cctgggcgcc ccaccacgcc tcatctgtga cagccgcgtc ctggagaggt     540
                atctcctgga ggccaaggag gccgagaata tcacgacggg ctgtgctgaa cactgcagcc     600
                tgaatgagaa tatcactgtc ccagacacca aagtgaattt ctatgcctgg aagaggatgg     660
                aggtcgggca gcaggccgtg gaagtctggc agggcctggc cctgctgtcc gaagctgtcc     720
                tgcggggcca ggccctgctg tcaactcttt cccagccgtg ggagcccctg cagctgcatg     780
                tggataaagc cgtcagtggc ctgcgcagcc tcaccactct gctgcgggct ctgggagccc     840
                agaaggaagc catctcccct ccagatgcgg cctccgctgg tccactccgc acaatcactg     900
                ctgacacttt ccgcaaactc ttccgagtct actccaattt cctccggggga aagctgaagc     960
                tgtacacagg ggaggcctgc aggacagggg acagatgagt ctagaaaagc cgaattctgc    1020
                aggaattggg tggcatccct gtgacccctc cccagtgcct ctcctggccc tggaagttgc    1080
                cactccagtg cccaccagcc ttgtcctaat aaaattaagt tgcatcattt tgtctgacta    1140
                ggtgtccttc tataatatta tggggtggag ggggggtta tggagcaagg ggcaagttgg    1200
                gaagacaacc tgtagggctc gaggggggggc ccgtaccag cttttgttcc ctttagtgag    1260
                ggttaatttc gagcttggtc ttccgcttcc tcgctcactg actcgctgcg ctcggtcgtt    1320
                cggctgcggc gagcggtatc agctcactca aaggcggtaa tacggttatc cacagaatca    1380
                ggggataacg caggaaagaa catgtgagca aaaggccagc aaaaggccag gaaccgtaaa    1440
                aaggccgcgt tgctggcgtt tttccatagg ctccgccccc ctgacgagca tcacaaaaat    1500
                cgacgctcaa gtcagaggtg gcgaaacccg acaggactat aaagatacca ggcgtttccc    1560
                cctggaagct ccctcgtgcg ctctcctgtt ccgaccctgc cgcttaccgg atacctgtcc    1620
                gcctttctcc cttcgggaag cgtggcgctt tctcatagct cacgctgtag gtatctcagt    1680
                tcggtgtagg tcgttcgctc caagctgggc tgtgtgcacg aaccccccgt tcagcccgac    1740
                cgctgcgcct tatccggtaa ctatcgtctt gagtccaacc cggtaagaca cgacttatcg    1800
                ccactggcag cagccactgg taacaggatt agcagagcga ggtatgtagg cggtgctaca    1860
                gagttcttga agtggtggcc taactacggc tacactagaa ggacagtatt tggtatctgc    1920
                gctctgctga agccagttac cttcggaaaa agagttggta gctcttgatc cggcaaacaa    1980
                accaccgctg gtagcggtgg tttttttgtt tgcaagcagc agattacgcg cagaaaaaaa    2040
                ggatctcaag aagatccttt gatcttttct acggggtctg acgctcagaa gaactcgtca    2100
                agaaggcgat agaaggcgat gcgctgcgaa tcgggagcgg cgataccgta aagcacgagg    2160
                aagcggtcag cccattcgcc gccaagctct tcagcaatat cacgggtagc caacgctatg    2220
                tcctgatagc ggtccgccac acccagccgg ccacagtcga tgaatccaga aaagcggcca    2280
                ttttccacca tgatattcgg caagcaggca tcgccatgcg tcacgacgag atcctcgccg    2340
                tcgggcatgc gcgccttgag cctggcgaac agttcggctg gcgcgagccc ctgatgctct    2400
                tcgtccagat catcctgatc gacaagaccg gcttccatcc gagtacgtgc tcgctcgatg    2460
                cgatgtttcg cttggtggtc gaatgggcag gtagccggat caagcgtatg cagccgccgc    2520
                attgcatcag ccatgatgga ctttctcg gcaggagcaa ggtgagatga caggagatcc    2580
                tgccccggca cttcgcccaa tagcagccag tcccttcccg cttcagtgac aacgtcgagc    2640
                acagctgcgc aaggaacgcc cgtcgtggcc agccacgata gccgcgctgc ctcgtcctg    2700
                agttcattca gggcaccgga caggtcggtc ttgacaaaaa gaaccgggcg cccctgcgct    2760
                gacagccgga acacggcggc atcagagcag ccgattgtct gttgtgccca gtcatagccg    2820
                aatagcctct ccacccaagc ggccggagaa cctgcgtgca atccatcttg ttcaatcatg    2880
                cgaaacgatc ctcatcctgt ctcttgatca gatcttgatc cctgcgcca tcagatcctt    2940
                ggcggcaaga aagccatcca gtttactttg cagggcttcc caaccttacc agagggcgcc    3000
                ccagctggca attccggttc gcttgctgtc cataaaaccg cccagtctag caactgttgg    3060
                gaagggcggg gctgcaggaa ttcgagcttg catgcctgca                            3100

<210> SEQ ID NO 24
<211> LENGTH: 630
<212> TYPE: PRT
```

```
<213> ORGANISM: artificial
<220> FEATURE:
<223> OTHER INFORMATION: General amino acid sequence of a truncated GAL4 DBD, hPR LBD
      separated by X and X can be shorter/ longer than depicted
<220> FEATURE:
<221> NAME/KEY: misc_feature
<222> LOCATION: (2)..(8)
<223> OTHER INFORMATION: Xaa can be any naturally occurring amino acid
<220> FEATURE:
<221> NAME/KEY: DOMAIN
<222> LOCATION: (9)..(81)
<220> FEATURE:
<221> NAME/KEY: misc_feature
<222> LOCATION: (82)..(83)
<223> OTHER INFORMATION: Xaa can be any naturally occurring amino acid
<220> FEATURE:
<221> NAME/KEY: misc_feature
<222> LOCATION: (359)..(361)
<223> OTHER INFORMATION: Xaa can be any naturally occurring amino acid

<400> SEQUENCE: 24

Met Xaa Xaa Xaa Xaa Xaa Xaa Lys Leu Leu Ser Ser Ile Glu Gln
 1               5                  10                  15
Ala Cys Asp Ile Cys Arg Leu Lys Lys Leu Lys Cys Ser Lys Glu Lys
             20                  25                  30
Pro Lys Cys Ala Lys Cys Leu Lys Asn Asn Trp Glu Cys Arg Tyr Ser
         35                  40                  45
Pro Lys Thr Lys Arg Ser Pro Leu Thr Arg Ala His Leu Thr Glu Val
     50                  55                  60
Glu Ser Arg Leu Glu Arg Leu Glu Gln Leu Phe Leu Leu Ile Phe Pro
65                  70                  75                  80
Arg Xaa Xaa Lys Lys Phe Asn Lys Val Arg Val Val Arg Ala Leu Asp
                 85                  90                  95
Ala Val Ala Leu Pro Gln Pro Val Gly Val Pro Asn Glu Ser Gln Ala
            100                 105                 110
Leu Ser Gln Arg Phe Thr Phe Ser Pro Gly Gln Asp Ile Gln Leu Ile
        115                 120                 125
Pro Pro Leu Ile Asn Leu Leu Met Ser Ile Glu Pro Asp Val Ile Tyr
    130                 135                 140
Ala Gly His Asp Asn Thr Lys Pro Asp Thr Ser Ser Ser Leu Leu Thr
145                 150                 155                 160
Ser Leu Asn Gln Leu Gly Glu Arg Gln Leu Leu Ser Val Val Lys Trp
                165                 170                 175
Ser Lys Ser Leu Pro Gly Phe Arg Asn Leu His Ile Asp Asp Gln Ile
            180                 185                 190
Thr Leu Ile Gln Tyr Ser Trp Met Ser Leu Met Val Phe Gly Leu Gly
        195                 200                 205
Trp Arg Ser Tyr Lys His Val Ser Gly Gln Met Leu Tyr Phe Ala Pro
    210                 215                 220
Asp Leu Ile Leu Asn Glu Gln Arg Met Lys Glu Ser Ser Phe Tyr Ser
225                 230                 235                 240
Leu Cys Leu Thr Met Trp Gln Ile Pro Gln Glu Phe Val Lys Leu Gln
                245                 250                 255
Val Ser Gln Glu Glu Phe Leu Cys Met Lys Val Leu Leu Leu Leu Asn
            260                 265                 270
Thr Ile Pro Leu Glu Gly Leu Arg Ser Gln Thr Gln Phe Glu Glu Met
        275                 280                 285
Arg Ser Ser Tyr Ile Arg Glu Leu Ile Lys Ala Ile Gly Leu Arg Gln
    290                 295                 300
Lys Gly Val Val Ser Ser Gln Arg Phe Tyr Gln Leu Thr Lys Leu
305                 310                 315                 320
Leu Asp Asn Leu His Asp Leu Val Lys Gln Leu His Leu Tyr Cys Leu
                325                 330                 335
Asn Thr Phe Ile Gln Ser Arg Ala Leu Ser Val Glu Phe Pro Glu Met
            340                 345                 350
Met Ser Glu Val Ile Ala Xaa Xaa Xaa Pro Met Glu Phe Gln Tyr Leu
        355                 360                 365
Pro Asp Thr Asp Asp Arg His Arg Ile Glu Glu Lys Arg Lys Arg Thr
    370                 375                 380
Tyr Glu Thr Phe Lys Ser Ile Met Lys Lys Ser Pro Phe Ser Gly Pro
385                 390                 395                 400
Thr Asp Pro Arg Pro Pro Arg Arg Ile Ala Val Pro Ser Arg Ser
                405                 410                 415
Ser Ala Ser Val Pro Lys Pro Ala Pro Gln Pro Tyr Pro Phe Thr Ser
            420                 425                 430
Ser Leu Ser Thr Ile Asn Tyr Asp Glu Phe Pro Thr Met Val Phe Pro
        435                 440                 445
Ser Gly Gln Ile Ser Gln Ala Ser Ala Leu Ala Pro Ala Pro Pro Gln
```

-continued

```
            450                 455                 460
    Val Leu Pro Gln Ala Pro Ala Pro Ala Pro Ala Met Val Ser
465                     470                 475                 480
    Ala Leu Ala Gln Ala Pro Ala Pro Val Pro Val Leu Ala Pro Gly Pro
                    485                 490                 495
    Pro Gln Ala Val Ala Pro Pro Ala Pro Lys Pro Thr Gln Ala Gly Glu
                500                 505                 510
    Gly Thr Leu Ser Glu Ala Leu Leu Gln Leu Gln Phe Asp Asp Glu Asp
                515                 520                 525
    Leu Gly Ala Leu Leu Gly Asn Ser Thr Asp Pro Ala Val Phe Thr Asp
                530                 535                 540
    Leu Ala Ser Val Asp Asn Ser Glu Phe Gln Gln Leu Leu Asn Gln Gly
545                     550                 555                 560
    Ile Pro Val Ala Pro His Thr Thr Glu Pro Met Leu Met Glu Tyr Pro
                    565                 570                 575
    Glu Ala Ile Thr Arg Leu Val Thr Gly Ala Gln Arg Pro Pro Asp Pro
                580                 585                 590
    Ala Pro Ala Pro Leu Gly Ala Pro Gly Leu Pro Asn Gly Leu Leu Ser
                595                 600                 605
    Gly Asp Glu Asp Phe Ser Ser Ile Ala Asp Met Asp Phe Ser Ala Leu
    610                     615                 620
    Leu Ser Gln Ile Ser Ser
625                     630

<210> SEQ ID NO 25
<211> LENGTH: 189
<212> TYPE: DNA
<213> ORGANISM: artificial
<220> FEATURE:
<223> OTHER INFORMATION: six repeating GAL-4 DNA binding site and a TATA box

<400> SEQUENCE: 25
aagcggagta ctgtcctccg agtggagtac tgtcctccga gcggagtact gtcctccgag      60
    tcgagggtcg aagcggagta ctgtcctccg agtggagtac tgtcctccga gcggagtact     120
    gtcctccgag tcgactctag agggtatata atggatctcg agatatcgga gctcgtttag     180
    tgaaccgtc                                                             189
```

The invevtion claimed is:

1. An inducible expression system comprising:
   (a) a first expression cassette including a promoter operably linked to a first nucleic acid sequence encoding a regulator protein, wherein the regulator protein comprises:
   a mutated GAL-4 DNA-binding domain that carries a mutation in a helical domain located in a region from amino acid 54-93 of SEQ ID NO: 10, wherein the mutation in the helical domain decreases dimerization of the regulator protein occurring in the absence of a anti-progestin ligand,
   a transregulatory domain selected from the group consisting of NFkappaBp65, VP-16, TAF-1, TAF-2, TAU-1, TAU-2, TEF-1 and ORF-10 transregulatory domains, and
   a ligand-binding domain of a progesterone receptor, wherein the ligand binding domain has a deletion in naturally occurring amino acids in a region encompassing from about 1 to about 60 carboxyl terminal amino acids of the ligand binding domain, said deletion conferring an ability to be activated by an anti-progestin ligand; and
   (b) a second expression cassette having a second nucleic acid sequence encoding a desired product, operably linked to a promoter comprising a GAL-4 binding site, wherein the regulator protein is activated in the presence of the anti-progestin and the expression of the second nucleic acid sequence is controlled by binding of the activated regulator protein to Gal-4 binding sites in the promoter region of the second expression cassette.

2. The inducible expression system of claim 1, wherein the mutation to the GAL-4 DNA binding domain and the ligand binding domain is selected from the group consisting of deletion, substitution, or addition.

3. The inducible expression system of claim 2 wherein the mutation is a deletion of amino acids 54-74 of SEQ ID NO: 10.

4. The inducible expression system of claim 2 wherein the mutation is a deletion of amino acids 54-64 of SEQ ID NO: 10.

5. The inducible expression system of claim 2 wherein the mutation is a deletion of amino acids 65-74 of SEQ ID NO: 10.

6. The inducible expression system of claim 2 wherein the mutation is a deletion of amino acids 86-93 of SEQ ID NO: 10.

7. The inducible expression system of claim 1 wherein the mutation in the mutated GAL-4 DNA binding domain is a deletion of the amino acids 75-93 of SEQ ID NO: 10.

8. The inducible expression system of claim 7 wherein the mutated GAL-4 DNA binding domain comprises amino acid sequence 2-74 of SEQ ID NO: 10.

9. The inducible expression system of claim 1 wherein the first expression cassette further comprises a tissue-specific promoter.

10. The inducible expression system of claim 9 wherein the tissue-specific promoter is a muscle-specific promoter.

11. The inducible expression system of claim 10 wherein the muscle-specific promoter is an α-actin promoter.

12. The inducible expression system of claim 1 wherein one or both of the first and the second expression cassette further comprises a 5' untranslated region that includes a synthetic intron.

13. The inducible expression system of claim 12 wherein the 5' untranslated region comprises SEQ ID NO: 8.

14. The inducible expression system of claim 12 wherein the synthetic intron comprises a sequence selected from the group consisting of SEQ ID NO: 5, SEQ ID NO: 6, and SEQ ID NO: 7.

15. The inducible expression system of claim 1 wherein the first and second expression cassettes further comprise a poly (A) signal derived from the poly (A) signal of human growth hormone.

16. The inducible expression system of claim 1 wherein the deletion is in naturally occurring amino acids 873-933 of the hPR, amino acids 891-933 of the hPR, or amino acids 914-933 of the hPR.

17. The inducible expression system of claim 1 wherein the regulator protein comprises an amino acid sequence selected from the group consisting of SEQ ID NO: 15 and SEQ ID NO: 24.

18. The inducible expression system of claim 1 wherein the anti-progestin is selected from the group consisting of 11β-(4-dimethylaminophenyl)-17β-hydroxy-17α-propynyl-4,9-estradiene-3-one (RU38486 or mifepristone); 11β-(4-dimethylaminophenyl)-17α-hydroxy-17β-(3-hydroxypropyl)-13α methyl-4,9-gonadiene-3-one (ZK98299 or Onapristone); 11β-(4-acetylphenyl)-17β-hydroxy-17α-(1-propynyl)-4,9-estradiene-3-one (ZK112993); 11β-(4-dimethylaminophenyl)-17β-hydroxy-17α-(3-hydroxy-1(Z)-propenyl-estra-4,9-diene-3-one (ZK98734); (7β,11β,17β)-11-(4-dimethylaminophenyl)-7-methyl-4',5'-dihydrospiro [ester-4,9-diene-17,2'(3'H)-furan]-3-one (Org31806); (11β, 14β,17α)-4',5'-dihydro-11-(4-dimethylaminophenyl)-[spiroestra-4,9-diene-17,2'(3'H)-furan]-3-one (Org31376); 5-α-pregnane-3,2-dione, Org 33628, and Org 33245.

19. The inducible expression system of claim 1 wherein the GAL-4 binding site comprises SEQ ID NO: 9.

20. The inducible expression system of claim 1 wherein the promoter region of the second expression cassette comprises a sequence selected from the group consisting of SEQ ID NOS: 18, 19, 20, and 21.

21. The inducible expression system of claim 1 wherein the promoter region of the second expression cassette comprises three to six repeating GAL-4 binding sites.

22. The inducible expression system of claim 1 wherein the transregulatory domain is a human transregulatory domain.

23. The inducible expression system of claim 1 wherein the desired product encoded by the second nucleic acid sequence is selected from the group consisting of erythropoeitin, a clotting factor and an interferon.

24. The inducible expression system of claim 23 wherein the clotting factor is a Factor IX.

25. The inducible expression system of claim 23 wherein the interferon is an interferon alpha.

26. The inducible expression system of claim 1 wherein the second expression cassette manifests an uninduced level of basal expression that does not result in a biological effect from a pharmacological dose of the second expression cassette.

27. The inducible expression system of claim 1 wherein the first and second expression cassette are part of a single nucleic acid vector.

28. The inducible expression system of claim 1 wherein the first expression cassette is part of a first nucleic acid vector and the second expression cassette is part of a second nucleic acid vector.

29. A method of regulating expression of a transgene in vivo comprising:
introducing the inducible expression system of claim 1 into a tissue in vivo; administering the anti-progestin to activate the regulator protein and induce expression of the nucleic acid sequence encoding the desired product.

30. The method of claim 29 wherein the amino acid sequence of the regulator protein is selected from the group consisting of SEQ ID NOS: 15 and 24.

31. The method of claim 29 wherein the anti-progestin is administered after inflammation associated with administration of the first and second expression cassettes has subsided.

32. A composition comprising:
a polymer selected from the group consisting of non-ionic polymers and anionic polymers, and
a pharmacological dose of the inducible expression system of claim 1.

33. The composition of claim 32 wherein the anionic polymer is poly-L-glutamate.

34. The composition of claim 32 wherein the non-ionic polymer is selected from a group consisting of PVP, PVA, and poloxamer.

35. The composition of claim 32 wherein the polymer, the first expression cassette, and the second expression cassette are co-lyophilized.

36. A method of inducing the expression of a transgene, the method comprising:
(a) introducing the inducible expression system of claim 1 into a cell; and
(b) inducing the expression of the transgene by administering an anti-progestin at least 12 days after the introduction of the inducible expression system into the cell.

37. The method of claim 36 wherein the inducible expression system is delivered by injection followed by electroporation.

38. The method of claim 37 wherein the delivery of the inducible expression system is by injection into muscle, followed by electroporation of the muscle.

39. The method in claim 36 wherein the expression of the transgene is induced at least 18 days after the introduction of the inducible expression system into the cell.

40. The method of claim 36 wherein the expression of the transgene is induced at least 20 days after the introduction of the inducible expression system into the cell.

41. The method in claim 36 wherein the expression of the transgene is induced at least 50 days after the introduction of the inducible expression system into the cell.

42. The method of claim 36 wherein the expression of the transgene is induced at least 54 days after the introduction of the inducible expression system into the cell.

43. The method in claim 36 wherein expression of the transgene is induced using a pulsatile program of induction.

44. The method in claim 36 further comprising the step of formulating the first expression cassette and the second expression cassette with a polymer selected from the group consisting of anionic and non-ionic polymers.

45. The method of claim 44 wherein the anionic polymer is poly-L-glutamate.

46. The method of claim 45 wherein the delivery of the inducible expression system is by intra-muscular injection together with electroporation, wherein the electroporation is conducted following the injection.

47. The method of claim 46 wherein the desired product encoded by the second nucleic acid is selected from the group consisting of erythropoeitin, a clotting factor and an interferon.

48. The method of claim 44 wherein the polymer is selected from a group consisting of PVP, PVA, and poloxamer.

49. A inducible expression system comprising:
- a first expression cassette having a first nucleic acid sequence encoding a fusion protein comprising
  - a GAL-4 DNA binding domain (SEQ ID NO: 10), wherein amino acids 75-93 are deleted;
  - a NFkappaBp65 transregulatory domain, and
  - a ligand-binding domain of a progesterone receptor having a deletion of about 19 naturally occurring amino acids C-terminal amino acids; and
- a second expression cassette having a second nucleic acid sequence encoding a desired product, operably linked to a promoter comprising Gal-4 binding sites,
- wherein the fusion protein is activated in the presence of an anti-progestin and the expression of the second nucleic acid sequence is controlled by binding of the activated fusion protein to the Gal-4 binding sites of the second expression cassette.

50. The inducible system of claim 49 wherein one or both of the first and the second expression cassette further comprises a 5' untranslated region that includes a synthetic intron.

* * * * *

UNITED STATES PATENT AND TRADEMARK OFFICE
CERTIFICATE OF CORRECTION

PATENT NO.       : 7,579,326 B2  
APPLICATION NO.  : 10/400053  
DATED            : August 25, 2009  
INVENTOR(S)      : Abruzzese et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 338 days.

Signed and Sealed this

Fourteenth Day of September, 2010

David J. Kappos  
*Director of the United States Patent and Trademark Office*